United States Patent
Chellaiah

(10) Patent No.: US 11,485,762 B2
(45) Date of Patent: Nov. 1, 2022

(54) COMPOSITIONS AND METHODS FOR INHIBITION OF L-PLASTIN ACTIVITY IN OSTEOCLASTS TO REDUCE BONE LOSS

(71) Applicant: Meenakshi Chellaiah, Columbia, MD (US)

(72) Inventor: Meenakshi Chellaiah, Columbia, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 16/639,925

(22) PCT Filed: Aug. 16, 2018

(86) PCT No.: PCT/US2018/000188
§ 371 (c)(1),
(2) Date: Feb. 18, 2020

(87) PCT Pub. No.: WO2019/035919
PCT Pub. Date: Feb. 21, 2019

(65) Prior Publication Data
US 2020/0255486 A1    Aug. 13, 2020

Related U.S. Application Data

(60) Provisional application No. 62/546,288, filed on Aug. 16, 2017.

(51) Int. Cl.
*C07K 14/47* (2006.01)
*A61P 19/08* (2006.01)
*A61K 9/51* (2006.01)
*A61K 38/00* (2006.01)

(52) U.S. Cl.
CPC ............ *C07K 14/47* (2013.01); *A61K 9/5153* (2013.01); *A61P 19/08* (2018.01); *A61K 38/00* (2013.01)

(58) Field of Classification Search
None
See application file for complete search history.

(56) References Cited

U.S. PATENT DOCUMENTS

| | | |
|---|---|---|
| 5,002,870 A | 3/1991 | Leavitt |
| 2006/0276389 A1 | 12/2006 | Poznansky |
| 2011/0027277 A1 | 2/2011 | Bharti |

FOREIGN PATENT DOCUMENTS

| | | |
|---|---|---|
| EP | 1669084 | 6/2006 |
| JP | H08119991 A  * | 5/1996 |
| WO | 0248377 | 6/2002 |
| WO | 2010108824 | 9/2010 |

OTHER PUBLICATIONS

Morley (Int J Cell Biol. 2012; 2012: 935173) (Year: 2012).*
Campbell et al. (Retrovirology 2009, 6:50) (Year: 2009).*
Tautzenberger et al. (Biomaterials 32 (2011) 1706e1714) (Year: 2011).*
Jones et al. (PNAS. vol. 95, pp. 9331-9336, Aug. 1998) (Year: 1998).*
Al Tanoury, Ziad, et al. "Quantitative kinetic study of the actin-bundling protein L-plastin and of its impact on actin turn-over." PloS one 5.2 (2010): e9210.
Babb, Sherry G., et al. "Fimbrin in podosomes of monocyte□derived osteoclasts." Cell motility and the cytoskeleton 37.4 (1997): 308-325.
Batsir, Sarit, Benjamin Geiger, and Zvi Kam. "Dynamics of the sealing zone in cultured osteoclasts." Cytoskeleton 74.2 (2017): 72-81.
Biswas, Rajat S., et al. "Polyphosphoinositides-dependent regulation of the osteoclast actin cytoskeleton and bone resorption." BMC cell biology 5.1 (2004): 1-21.
Blavier, L., and J. M. Delaisse. "Matrix metalloproteinases are obligatory for the migration of preosteoclasts to the developing marrow cavity of primitive long bones." Journal of Cell Science 108.12 (1995): 3649-3659.
Chellaiah et al., "Peptidomimetic inhibitors of L-plastin reduce the resorptive activity of osteoclast but not the bone forming activity of osteoblasts in vitro", PLoS One, (Sep. 24, 2018), vol. 13, No. 9, p. e0204209, XP055576507.
Chellaiah, M. A., and K. A. Hruska. "The Integrin {alpha} v{beta} 3 and CD44 Regulate the Actions of Osteopontin on Osteoclast Motility." Calcified Tissue International 72.3 (2003): 197-205.
Chellaiah, Meenakshi A. "Regulation of podosomes by integrin αvβ3 and Rho GTPase-facilitated phosphoinositide signaling." European journal of cell biology 85.3-4 (2006): 311-317.
Chellaiah, Meenakshi A., and Michael D. Schaller. "Activation of Src kinase by protein-tyrosine phosphatase—PEST in osteoclasts: Comparative analysis of the effects of bisphosphonate and protein-tyrosine phosphatase inhibitor on Src activation in vitro." Journal of cellular physiology 220.2 (2009): 382-393.
Chellaiah, Meenakshi A., et al. "Osteopontin deficiency produces osteoclast dysfunction due to reduced CD44 surface expression." Molecular biology of the cell 14.1 (2003): 173-189.
Chellaiah, Meenakshi A., et al. "Phosphorylation of a Wiscott-Aldrich syndrome protein-associated signal complex is critical in osteoclast bone resorption." Journal of Biological Chemistry 282.13 (2007): 10104-10116.
Chellaiah, Meenakshi A., et al. "Rho-A is critical for osteoclast podosome organization, motility, and bone resorption." Journal of Biological Chemistry 275.16 (2000): 11993-12002.
Chellaiah, Meenakshi A., et al. "Rho-dependent Rho kinase activation increases CD44 surface expression and bone resorption in osteoclasts." Journal of Biological Chemistry 278.31 (2003): 29086-29097.

(Continued)

*Primary Examiner* — Sergio Coffa
(74) *Attorney, Agent, or Firm* — Riverside Law LLP

(57) ABSTRACT

The present disclosure relates to compositions and methods for inhibiting L-plastin activity for inhibiting bone resorption activity of osteoclasts. In certain instances, the compositions and methods are used to treat or prevent a disease or disorder associated with bone resorption. In one aspect, the compositions and methods relate to peptide inhibitors comprising an N-terminal fragment of L-plastin.

4 Claims, 23 Drawing Sheets
Specification includes a Sequence Listing.

(56) References Cited

OTHER PUBLICATIONS

Chellaiah, Meenakshi A., Tao Ma, and Sunipa Majumdar. "L-plastin phosphorylation regulates the early phase of sealing ring formation by actin bundling process in mouse osteoclasts." Experimental cell research 372.1 (2018): 73-82.

Chellaiah, Meenakshi, and Keith Hruska. "Osteopontin stimulates gelsolin-associated phosphoinositide levels and phosphatidylinositol triphosphate-hydroxyl kinase." Molecular biology of the cell 7.5 (1996): 743-753.

Chellaiah, Meenakshi, et al. "c-Src is required for stimulation of gelsolin-associated phosphatidylinositol 3-kinase." Journal of Biological Chemistry 273.19 (1998): 11908-11916.

Chellaiah, Meenakshi, et al. "Gelsolin deficiency blocks podosome assembly and produces increased bone mass and strength." The Journal of cell biology 148.4 (2000): 665-678.

Chen, Hua, et al. "Role for plastin in host defense distinguishes integrin signaling from cell adhesion and spreading." Immunity 19.1 (2003): 95-104.

De Arruda, Monika V., et al. "Fimbrin is a homologue of the cytoplasmic phosphoprotein plastin and has domains homologous with calmodulin and actin gelation proteins." The Journal of cell biology 111.3 (1990): 1069-1079.

De Clercq, Sarah, et al. "L-plastin nanobodies perturb matrix degradation, podosome formation, stability and lifetime in THP-1 macrophages." PloS one 8.11 (2013): e78108.

Delanote, Veerle, Joel Vandekerckhove, and Jan Gettemans. "Plastins: versatile modulators of actin organization in (patho) physiological cellular processes." Acta pharmacologica Sinica 26.7 (2005): 769-779.

Desai, Bhavik, Tao Ma, and Meenakshi A. Chellaiah. "Invadopodia and matrix degradation, a new property of prostate cancer cells during migration and invasion." Journal of Biological Chemistry 283.20 (2008): 13856-13866.

Duong, Le T., and Gideon A. Rodan. "The role of integrins in osteoclast function." Journal of bone and mineral metabolism 17.1 (1999): 1-6.

Duong, Le T., et al. "PYK2 in osteoclasts is an adhesion kinase, localized in the sealing zone, activated by ligation of alpha (v) beta3 integrin, and phosphorylated by src kinase." The Journal of clinical investigation 102.5 (1998): 881-892.

Faccio, Roberta, et al. "Localization and possible role of two different alpha v beta 3 integrin conformations in resting and resorbing osteoclasts." Journal of cell science 115.14 (2002): 2919-2929.

Fahiminiya, Somayyeh, et al. "Osteoporosis caused by mutations in PLS3: clinical and bone tissue characteristics." Journal of Bone and Mineral Research 29.8 (2014): 1805-1814.

Feng, Xu, et al. "A Glanzmann's mutation in β3 integrin specifically impairs osteoclast function." The Journal of clinical investigation 107.9 (2001): 1137-1144.

Foran, Eilis, et al. "The leukocyte protein L☐plastin induces proliferation, invasion and loss of E☐ cadherin expression in colon cancer cells." International journal of cancer 118.8 (2006): 2098-2104.

Frederick, Mitchell J., et al. "Characterization of the Mr 65,000 lymphokine-activated killer proteins phosphorylated after tumor target binding: evidence that pp65a and pp65b are phosphorylated forms of L-plastin." Cancer research 56.1 (1996): 138-144.

Freeley, Michael, et al. "L-plastin regulates polarization and migration in chemokine-stimulated human T lymphocytes." The Journal of Immunology 188.12 (2012): 6357-6370.

Georgess, Dan, et al. "Podosome organization drives osteoclast-mediated bone resorption." Cell adhesion & migration 8.3 (2014): 192-204.

Gupta, Anandarup, et al. "Leupaxin is a critical adaptor protein in the adhesion zone of the osteoclast." Journal of Bone and Mineral Research 18.4 (2003): 669-685.

Hanein, Dorit, et al. "An atomic model of fimbrin binding to F-actin and its implications for filament crosslinking and regulation." Nature structural biology 5.9 (1998): 787-792.

Hartman, George D., and Mark E. Duggan. "αvβ3 integrin antagonists as inhibitors of bone resorption." Expert opinion on investigational drugs 9.6 (2000): 1281-1291.

Izawa, Takashi, et al. "c-Src links a RANK/αvβ3 integrin complex to the osteoclast cytoskeleton." Molecular and cellular biology 32.14 (2012): 2943-2953.

Janji, Bassam, et al. "Phosphorylation on Ser5 increases the F-actin-binding activity of L-plastin and promotes its targeting to sites of actin assembly in cells." Journal of cell science 119.9 (2006): 1947-1960.

Jones, Samuel L., and Eric J. Brown. "FcγRll-mediated adhesion and phagocytosis induce L-plastin phosphorylation in human neutrophils." Journal of Biological Chemistry 271.24 (1996): 14623-14630.

Jones, Samuel L., et al. "A role for the actin-bundling protein L-plastin in the regulation of leukocyte integrin function." Proceedings of the National Academy of Sciences 95.16 (1998): 9331-9336.

Jurdic, Pierre, et al. "Podosome and sealing zone: specificity of the osteoclast model." European journal of cell biology 85.3-4 (2006): 195-202.

Kanehisa, J., et al. "A band of F-actin containing podosomes is involved in bone resorption by osteoclasts." Bone 11.4 (1990): 287-293.

Klemke et al., "Phosphorylation of ectopically expressed L-plastin enhances invasiveness of human melanoma cells", International Journal of Cancer, (Apr. 10, 2007), vol. 120, No. 12, pp. 2500-2599, XP055576503.

Lakkakorpi, Päivi T., and H. Kalervo Väänänen. "Cytoskeletal changes in osteoclasts during the resorption cycle." Microscopy research and technique 33.2 (1996): 171-181.

Lakkakorpi, Paivi T., and Kalervo H. Väänänen. "Kinetics of the osteoclast cytoskeleton during the resorption cycle in vitro." Journal of Bone and Mineral Research 6.8 (1991): 817-826.

Lebart, M-C., et al. "Biochemical Characterization of the L-Plastin-Actin Interaction Shows a Resemblance with That of α-Actinin and Allows a Distinction to Be Made between the Two Actin-Binding Domains of the Molecule." Biochemistry 43.9 (2004): 2428-2437.

Lee, Eun-Jung, et al. "Inhibition of osteoclast activation by phloretin through disturbing αvβ3 integrin-c-Src pathway." BioMed research international 2015 (2015).

Li, Nan, Chris KC Wong, and C. Yan Cheng. "Plastins regulate ectoplasmic specialization via its actin bundling activity on microfilaments in the rat testis." Asian journal of andrology 18.5 (2016): 716.

Lin, Ching-Shwun, Angie Lau, and Tom F. Lue. "Analysis and mapping of plastin phosphorylation." DNA and cell biology 17.12 (1998): 1041-1046.

Luxenburg, Chen, et al. "The architecture of the adhesive apparatus of cultured osteoclasts: from podosome formation to sealing zone assembly." PloS one 2.1 (2007): e179.

Luxenburg, Chen, Lia Addadi, and Benjamin Geiger. "The molecular dynamics of osteoclast adhesions." European journal of cell biology 85.3-4 (2006): 203-211.

Ma, Tao, Kavitha Sadashivaiah, and Meenakshi A. Chellaiah. "Regulation of sealing ring formation by L-plastin and cortactin in osteoclasts." Journal of Biological Chemistry 285.39 (2010): 29911-29924.

Ma, Tao, Venkatesababa Samanna, and Meenakshi A. Chellaiah. "Dramatic inhibition of osteoclast sealing ring formation and bone resorption in vitro by a WASP-peptide containing pTyr294 amino acid." Journal of Molecular Signaling 3.1 (2008): 1-12.

Marchisio, Pier Carlo, et al. "Rous sarcoma virus-transformed fibroblasts and cells of monocytic origin display a peculiar dot-like organization of cytoskeletal proteins involved in microfilament-membrane interactions." Experimental cell research 169.1 (1987): 202-214.

McHugh, Kevin P., et al. "Mice lacking β3 integrins are osteosclerotic because of dysfunctional osteoclasts." The Journal of clinical investigation 105.4 (2000): 433-440.

(56) References Cited

OTHER PUBLICATIONS

Miyauchi, Akimitsu, et al. "Recognition of osteopontin and related peptides by an alpha v beta 3 integrin stimulates immediate cell signals in osteoclasts." Journal of Biological Chemistry 266.30 (1991): 20369-20374.
Miyazaki, Tsuyoshi, et al. "Src kinase activity is essential for osteoclast function." Journal of Biological Chemistry 279.17 (2004): 17660-17666.
Morley, Sharon Celeste, et al. "The actin-bundling protein L-plastin dissociates CCR7 proximal signaling from CCR7-induced motility." The Journal of Immunology 184.7 (2010): 3628-3638.
Morley, Sharon Celeste. "The actin-bundling protein L-plastin: a critical regulator of immune cell function." International journal of cell biology 2012 (2012).
Morley, Sharon Celeste. "The actin☐bundling protein L☐plastin supports T☐cell motility and activation." Immunological reviews 256.1 (2013): 48-62.
Nagahara, Hikaru, et al. "Transduction of full-length TAT fusion proteins into mammalian cells: TAT-p27 Kip1 induces cell migration." Nature medicine 4.12 (1998): 1449-1452.
Nakamura, Ichiro, et al. "Role of alpha (v) beta (3) integrin in osteoclast migration and formation of the sealing zone." Journal of cell science 112.22 (1999): 3985-3993.
Namba, Yuziro, et al. "Human T cell L-plastin bundles actin filaments in a calcium dependent manner." The Journal of Biochemistry 112.4 (1992): 503-507.
Neto et al., "Antibodies to T- and L-isoforms of the cytoskeletal protein, fimbrin, in patients with systemic lupus erythematosus", The Journal of Clinical Investigation, (Sep. 1, 1992), vol. 90, No. 3, pp. 1037-1042, XP055576502.
Novack, Deborah V., and Roberta Faccio. "Osteoclast motility: putting the brakes on bone resorption." Ageing research reviews 10.1 (2011): 54-61.
Otsuka, Motoyuki, et al. "Differential expression of the L-plastin gene in human colorectal cancer progression and metastasis." Biochemical and biophysical research communications 289.4 (2001): 876-881.
Rao, Jian Yu, et al. "Cellular F-actin levels as a marker for cellular transformation: relationship to cell division and differentiation." Cancer Research 50.8 (1990): 2215-2220.
Saltel, Frédéric, et al. "Actin cytoskeletal organisation in osteoclasts: a model to decipher transmigration and matrix degradation." European journal of cell biology 87.8-9 (2008): 459-468.
Saltel, Frédéric, et al. "Apatite-mediated actin dynamics in resorbing osteoclasts." Molecular biology of the cell 15.12 (2004): 5231-5241.
Samanna, V., et al. "Actin polymerization modulates CD44 surface expression, MMP☐9 activation, and osteoclast function." Journal of cellular physiology 213.3 (2007): 710-720.
Sato, Takuya, et al. "Identification of the membrane-type matrix metalloproteinase MT1-MMP in osteoclasts." Journal of cell science 110.5 (1997): 589-596.
Soysa, Niroshani Surangika, and Neil Alles. "Osteoclast function and bone-resorbing activity: An overview." Biochemical and biophysical research communications 476.3 (2016): 115-120.
Teitelbaum, Steven L. "The osteoclast and its unique cytoskeleton." Annals of the New York Academy of Sciences 1240.1 (2011): 14-17.
Teti, A. N. N. A., Pier Carlo Marchisio, and A. Zambonin Zallone. "Clear zone in osteoclast function: role of podosomes in regulation of bone-resorbing activity." American Journal of Physiology—Cell Physiology 261.1 (1991): C1-C7.
Vocero-Akbani, Adamina, et al. "Protein transduction: delivery of Tat-GTPase fusion proteins into mammalian cells." Methods in enzymology 332 (2001): 36-49.
Volkmann, Niels, et al. "An atomic model of actin filaments cross-linked by fimbrin and its implications for bundle assembly and function." The Journal of cell biology 153.5 (2001): 947-956.
Wang, Chen, et al. "Actin-bundling protein L-plastin regulates T cell activation." The Journal of immunology 185.12 (2010): 7487-7497.
Wang, Jun, and Eric J. Brown. "Immune complex-induced integrin activation and L-plastin phosphorylation require protein kinase A." Journal of Biological Chemistry 274.34 (1999): 24349-24356.
Wang, Jun, Hua Chen, and Eric J. Brown. "L-plastin peptide activation of αvβ3-mediated adhesion requires integrin conformational change and actin filament disassembly." Journal of Biological Chemistry 276.17 (2001): 14474-14481.
Winder, Steven J., and Kathryn R. Ayscough. "Actin-binding proteins." Journal of cell science 118.4 (2005): 651-654.

\* cited by examiner

| Nanoparticle | Size (nm)[a] | PDI[b] | Zeta Potential (mV)[c] | Peptide loading (%) |
|---|---|---|---|---|
| PLGA-PEG_P1 | 157 ± 4 | 0.058 ± 0.02 | -3.6 ± 0.8 | 5 |
| PLGA-PEG_P5 | 136 ± 5 | 0.062 ± 0.03 | -3.1 ± 0.2 | 5 |

Physicochemical characterization data represents the average of 3 independent experiments +/- SD.
[a] Hydrodynamic diameter (number mean) measured by dynamic light scattering.
[b] Polydispersity index indicates the distribution of individual molecular masses in a batch of nanoparticles, measured by dynamic light scattering.
[c] Surface charge measured at 25 °C in 15x diluted PBS with ~9 mM NaCl, pH 7.4.

Figure 19

SEQUENCE LISTING

```
<160> NUMBER OF SEQ ID NOS: 35

<210> SEQ ID NO 1
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1

Met Ala Arg Gly Ser Val Ser Asp Glu Glu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 2

Met Ala Arg Gly Ala Val Ala Asp Glu Glu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 3

Met Ala Arg Gly Ala Val Ser Asp Glu Glu
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 4

Met Ala Arg Gly Ser Val Ala Asp Glu Glu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 5

Arg Lys Lys Arg Arg Gln Arg Arg Arg Pro Pro
1               5                   10

<210> SEQ ID NO 6
<211> LENGTH: 11
<212> TYPE: PRT
```

```
<213> ORGANISM: Artificial Sequence
<220> FEATURE:
<223> OTHER INFORMATION: Chemically Synthesized

<400> SEQUENCE: 6

Tyr Gly Arg Lys Lys Arg Arg Gln Arg Arg
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 7

Arg Arg Arg Gln Arg Arg Lys Lys Arg Gly Tyr
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 8

Arg Lys Lys Arg Arg Gln Arg Arg Arg
1               5

<210> SEQ ID NO 9
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 9

Thr His Arg Leu Pro Arg Arg Arg Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 10

Gly Gly Arg Arg Ala Arg Arg Arg Arg Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 11

Arg Arg Gln Arg Arg Thr Ser Lys Leu Met Lys Arg
1               5                   10

<210> SEQ ID NO 12
<211> LENGTH: 27
<212> TYPE: PRT
<213> ORGANISM: Artificial Sequence
```

```
<220> FEATURE:
<223> OTHER INFORMATION: Chemically Synthesized

<400> SEQUENCE: 12

Gly Trp Thr Leu Asn Ser Ala Gly Tyr Leu Leu Gly Lys Ile Asn Leu
1               5                   10                  15
Lys Ala Leu Ala Ala Leu Ala Lys Lys Ile Leu
            20                  25

<210> SEQ ID NO 13
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 13

Lys Ala Leu Ala Trp Glu Ala Lys Leu Ala Lys Ala Leu Ala Lys Ala
1               5                   10                  15
Leu Ala Lys His Leu Ala Lys Ala Leu Ala Lys Ala Leu Lys Cys Glu
            20                  25                  30
Ala

<210> SEQ ID NO 14
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 14

Arg Gln Ile Lys Ile Trp Phe Gln Asn Arg Arg Met Lys Trp Lys Lys
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 15

Cys Met His Ile Glu Ser Leu Asp Ser Tyr Thr Cys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 16

Cys Met Tyr Ile Glu Ala Leu Asp Lys Tyr Ala Cys
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 17

Arg Arg Arg Arg Arg Arg Arg Arg Arg
```

```
1               5

<210> SEQ ID NO 18
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 18

Gly Arg Lys Lys Arg Arg Gln Arg Arg Arg Pro Pro Gln
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 19

Arg Gln Ile Lys Ile Trp Phe Gln Asn Arg Arg Met Lys Trp Lys Lys
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 20

Arg Gln Ile Arg Ile Trp Phe Gln Asn Arg Arg Met Arg Trp Arg Arg
1               5                   10                  15

<210> SEQ ID NO 21
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 21

Leu Leu Ile Ile Leu Arg Arg Arg Ile Arg Lys Gln Ala His Ala His
1               5                   10                  15

Ser Lys

<210> SEQ ID NO 22
<211> LENGTH: 22
<212> TYPE: PRT
<213> ORGANISM: Artificial Sequence
<220> FEATURE:
<223> OTHER INFORMATION: Chemically Synthesized

<400> SEQUENCE: 22

Met Val Thr Val Leu Phe Arg Arg Leu Arg Ile Arg Arg Ala Cys Gly
1               5                   10                  15

Pro Pro Arg Val Arg Val
                20

<210> SEQ ID NO 23
<211> LENGTH: 21
<212> TYPE: PRT
<213> ORGANISM: Artificial Sequence
<220> FEATURE:
<223> OTHER INFORMATION: Chemically Synthesized
```

<400> SEQUENCE: 23

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 24
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 24
acatgaccgg tatggccaga ggatccgtg                                    29

<210> SEQ ID NO 25
<211> LENGTH: 35
<212> TYPE: DNA
<213> ORGANISM: Artificial Sequence
<220> FEATURE:
<223> OTHER INFORMATION: Chemically Synthesized

<400> SEQUENCE: 25
cacatgaatt cacttacacc ctcttcatcc ctttc                             35

<210> SEQ ID NO 26
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 26
acatgaccgg tatggccaga ggatccgtg                                    29

<210> SEQ ID NO 27
<211> LENGTH: 38
<212> TYPE: DNA
<213> ORGANISM: Artificial Sequence
<220> FEATURE:
<223> OTHER INFORMATION: Chemically Synthesized

<400> SEQUENCE: 27
cacatgaatt cacttagtac ccaggcagag gcaggcag                          38

<210> SEQ ID NO 28
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 28
acatgaccgg tacctctgag cagtccagcg ttg                               33

<210> SEQ ID NO 29
<211> LENGTH: 37
<212> TYPE: DNA
<213> ORGANISM: Artificial Sequence
<220> FEATURE:
<223> OTHER INFORMATION: Chemically Synthesized

<400> SEQUENCE: 29
cacatgaatt cacttacttc tgtccacctc cgatatc                              37

<210> SEQ ID NO 30
<211> LENGTH: 49
<212> TYPE: DNA
<213> ORGANISM: Artificial Sequence
<220> FEATURE:
<223> OTHER INFORMATION: Chemically Synthesized

<400> SEQUENCE: 30
acgcgtcgac atggccagag gagcagtggc cgatgaggaa atgatggag              49

<210> SEQ ID NO 31
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 31
tgctgcagca tgcattctgc cctc                                          24

<210> SEQ ID NO 32
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 32
cggggtacca tggccagagg agcagtggcc                                    30

<210> SEQ ID NO 33
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 33
ggaatgaaga gggtgtgaga attccgg                                       27

<210> SEQ ID NO 34
<211> LENGTH: 45
<212> TYPE: PRT
<213> ORGANISM: Artificial Sequence
<220> FEATURE:
<223> OTHER INFORMATION: Chemically Synthesized

<400> SEQUENCE: 34

Met Ala Arg Gly Ser Val Ser Asp Glu Glu Met Met Glu Leu Arg Glu
1               5                   10                  15

Ala Phe Ala Lys Val Asp Thr Asp Gly Asn Gly Tyr Ile Ser Phe Asn
            20                  25                  30

Glu Leu Asn Asp Leu Phe Lys Ala Ala Cys Leu Pro Leu
        35                  40                  45

```
<210> SEQ ID NO 35
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 35

Ser Arg Ser Gly Met Val Glu Glu Ala Asp
1               5                   10
```

COMPOSITIONS AND METHODS FOR INHIBITION OF L-PLASTIN ACTIVITY IN OSTEOCLASTS TO REDUCE BONE LOSS

CROSS REFERENCE TO RELATED APPLICATIONS

This application is a U.S. national phase application filed under 35 U.S.C. § 371 claiming benefit to International Patent Application No. PCT/US2018/000188, filed Aug. 16, 2018, which is entitled to priority under 35 U.S.C. § 119(e) to U.S. Provisional Application No. 62/546,288, filed Aug. 16, 2017, each of which is hereby incorporated by reference herein in its entirety.

STATEMENT REGARDING FEDERALLY SPONSORED RESEARCH OR DEVELOPMENT

This invention was made with government support under the Grant Number AR066044 awarded by the National institutes of Health. The government has certain rights in the invention.

BACKGROUND OF THE INVENTION

In normal, healthy bone, which undergoes constant remodeling activity, the activity of osteoclasts (cells responsible for bone resorption) is balanced with the activity of osteoblasts (cells responsible for bone formation by differentiating into mature bone cells known as osteocytes).

Osteoporosis, a loss in bone mass associated with estrogen deficiency and aging, is a major public health concern worldwide. Bone loss results from an imbalance between bone resorption and bone formation. Osteoporosis is caused by increased bone removal due to increased osteoclast activity and decreased bone formation due to insufficient osteoclast activity. An ideal therapeutic approach for osteoporosis would decrease osteoclast activity without interfering with osteoblast-driven bone formation. Although targeted therapies such as bisphosphonates currently are available to treat and/or prevent osteoporosis by blocking osteoclast activity, evidence shows that long-term treatment causes a reduction in osteoblast-mediated bone formation, resulting in atypical skeletal fractures.

Several actin-binding proteins are involved in the cytoskeletal organization during cell migration, invasion, adhesion, and bone resorption. Previous observations in gelsolin null (Gsn−/−) osteoclasts demonstrated that gelsolin deficiency blocks podosome assembly and motility. However, these cells still exhibit sealing ring and matrix resorption (Chellaiah et al., 2000, J. Cell Biol., 148: 665-678). Therefore, Gsn−/− osteoclasts are capable of resorbing bone, but the resorbed areas are small due to the absence of podosomes and the resulting hypo-motile nature of osteoclasts (Chellaiah et al., 2000, J. Cell Biol., 148: 665-678). Observations in Gsn−/− osteoclasts also suggest that the organization of sealing ring presumably reflects changes in the role of actin-binding proteins. Sealing ring formation in osteoclasts is a requirement for bone resorption. Due to the architectural nature of sealing rings, the major reorganization of actin filaments is required during their formation. Knowledge of the formation of mature sealing ring development remains limited. Sealing rings consisting of stable actin filaments generate tight sealing zones on the bone surface during bone resorption by osteoclasts. Thus, elucidating the role of actin-binding proteins on actin dynamics and stability in the formation of actin filaments, an area that has remained unexplored, will provide novel information regarding the kinetics of sealing ring formation.

How spatial and temporal localization of actin-modulating protein(s) and actin control the formation of sealing rings still needs further elucidation. While many of the proteins that compose the sealing ring have been identified, their function is still poorly understood. The knowledge of the formation of nascent sealing zones (NSZs) before mature sealing ring development is very limited.

Thus, there is a need in the an for improved compositions and methods for inhibiting sealing ring formation and bone resorption. The present invention satisfies this unmet need.

SUMMARY OF THE INVENTION

In one aspect, the present invention provides a composition for inhibiting bone resorption comprising an inhibitor of L-plastin (LPL). In one embodiment, the inhibitor inhibits serine phosphorylation of LPL in one embodiment, the inhibitor is selected from the group consisting of nucleic acid molecule, a peptide, a small molecule, a siRNA, a ribozyme, an antisense nucleic acid, an antagonist, an aptamer, and a peptidomimetic.

In one embodiment, the inhibitor comprises a peptide comprising an N-terminal fragment, or a variant thereof, of LPL. In one embodiment, the N-terminal fragment, or a variant thereof, of LPL comprises an amino acid sequence selected from the group consisting of SEQ ID NO: 1, SEQ ID NO: 2, SEQ ID NO: 3, SEQ ID NO: 4 and SEQ ID NO: 34.

In one embodiment, the peptide is a fusion peptide comprising a transduction domain and an inhibitor domain, wherein the inhibitor domain comprises an N-terminal fragment of LPL, or a variant thereof. In one embodiment, the transduction domain comprises an amino acid sequence derived from HIV-I TAT. In one embodiment, the transduction domain comprises the amino acid sequence of SEQ ID NO: 5. In one embodiment, the transduction domain comprises the amino acid sequence of SEQ ID NO: 5 and wherein the inhibitor domain comprises an amino acid sequence selected from the group consisting of SEQ ID NO: 1, SEQ ID NO: 2, SEQ ID NO: 3, SEQ ID NO: 4 and SEQ ID NO: 34.

In one embodiment, the composition comprises a nanoparticle encapsulating the inhibitor.

In one aspect, the present invention provides a method of treating or preventing a disease or disorder associated with bone resorption in a subject in need thereof, comprising administering to the subject an effective amount of a composition comprising an inhibitor of L-plastin (LPL). In one embodiment, the disease or disorder is selected from the group consisting of osteoporosis, idiopathic primary osteoporosis, age-related osteoporosis, glucocorticoid-induced osteoporosis, Hajdu-Cheney syndrome, osteolysis post-transplant bone disease, Paget's disease of bone, bone loss associated with cancer, periodontal disease, and periodontitis.

In one embodiment, the inhibitor inhibits serine phosphorylation of LPL. In one embodiment, the inhibitor is selected from the group consisting of nucleic acid molecule, a peptide, a small molecule, a siRNA, a ribozyme, an antisense nucleic acid, an antagonist, an aptamer, and a peptidomimetic.

In one embodiment, the inhibitor comprises a peptide comprising an N-terminal fragment, or a variant thereof, of LPL. In one embodiment, the N-terminal fragment, or a variant thereof, of LPL comprises an amino acid sequence selected from the group consisting of SEQ ID NO: 1, SEQ ID NO: 2, SEQ ID NO: 3, SEQ ID NO: 4 and SEQ ID NO: 34.

In one embodiment, the peptide is a fusion peptide comprising a transduction domain and an inhibitor domain, wherein the inhibitor domain comprises an N-terminal fragment of LPL, or a variant thereof. In one embodiment, the transduction domain comprises an amino acid sequence derived from HIV-1 TAT. In one embodiment, the transduction domain comprises the amino acid sequence of SEQ ID NO: 5. In one embodiment, the transduction domain comprises the amino acid sequence of SEQ ID NO: 5 and wherein the inhibitor domain comprises an amino acid sequence selected from the group consisting of SEQ ID NO: 1, SEQ ID NO: 2, SEQ ID NO: 3, SEQ ID NO: 4 and SEQ ID NO: 34.

In one embodiment, the composition comprises a nanoparticle encapsulating the inhibitor.

In one aspect, the present invention provides a method of inhibiting bone resorption activity of an osteoclast comprising contacting the osteoclast with an inhibitor of L-plastin (LPL).

In one embodiment, the inhibitor inhibits serine phosphorylation of LPL. In one embodiment, the inhibitor is selected from the group consisting of nucleic acid molecule, a peptide, a small molecule, a siRNA, a ribozyme, an antisense nucleic acid, an antagonist, an aptamer, and a peptidomimetic.

In one embodiment, the inhibitor comprises a peptide comprising an N-terminal fragment, or a variant thereof, of LPL. In one embodiment, the N-terminal fragment, or a variant thereof, of LPL comprises an amino acid sequence selected from the group consisting of SEQ ID NO: 1, SEQ ID NO: 2, SEQ ID NO: 3, SEQ ID NO: 4 and SEQ ID NO: 34.

In one embodiment, the peptide is a fusion peptide comprising a transduction domain and an inhibitor domain, wherein the inhibitor domain comprises an N-terminal fragment of LPL, or a variant thereof. In one embodiment, the transduction domain comprises an amino acid sequence derived from HIV-I TAT. In one embodiment, the transduction domain comprises the amino acid sequence of SEQ ID NO: 5. In one embodiment, the transduction domain comprises the amino acid sequence of SEQ ID NO: 5 and wherein the inhibitor domain comprises an amino acid sequence selected from the group consisting of SEQ ID NO: 1, SEQ ID NO: 2, SEQ ID NO: 3, SEQ ID NO: 4 and SEQ ID NO: 34.

In one embodiment, the composition comprises a nanoparticle encapsulating the inhibitor.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1A through FIG. 1D, depicts the results of example experiments demonstrating the purification and analysis of dose and time-dependent uptake of TAT-fused LPL peptides. FIG. 1A depicts a schematic diagram demonstrating various LPL constructs generated in a pTAT-HA expression vector. The domain organization of LPL is shown in full-length LPL (FL-LPL). The following are cloned separately into the pTAT-HA expression vector: FL-LPL, mutated FL-LPL (S5S7-A5A7), amino-terminal LPL containing S5 and S7 (NT-LPL), and actin-binding domains of LPL (ABD-LPL). The number within the parentheses indicates the first and last amino acid of the corresponding LPL peptide. The expression vector contains TAT protein transduction domain (10aa) and an HA-tag (20aa). FIG. 1B shows the SDS-PAGE analysis of purified TAT-fused LPL peptides. TAT-fused peptides were subjected to 8% (lanes 1 and 2) and 15% (lanes 3-5) SDS-PAGE and stained with Coomassie blue. The purified proteins and their approximate molecular mass (kDa) are indicated below each lane. The standard molecular weight markers (kDa) are also indicated for 8% (left) and 15% (right) polyacrylamide gels (FIG. 1B). Demonstration of a dose- and time-dependent uptake of TAT-fused FL-LPL in osteoclasts (FIG. 1C and FIG. 1D). Immunoblotting analysis with an HA antibody was done to detect the transduced protein levels in osteoclast lysates. The blot was stripped and blotted with a GAPDH antibody for normalization (bottom panels of FIG. 1C and FIG. 1D). The results shown in FIG. 1B-FIG. 1D are representative of two different experiments from two different osteoclasts and TAT-protein preparations.

FIG. 2A through FIG. 2D, depicts the results from example experiments demonstrating the immunoblotting analysis of phosphorylation of transduced and endogenous LPL protein in lysates made from osteoclasts. Osteoclasts treated with bone particles and TNF-α were also transduced with the following TAT-fused LPL and control (HSV-TK) peptides (150 nM) for 3 hours as described elsewhere herein: FL-LPL (FIG. 2A; lanes 2 and 5); mutated FL-LPL (lane 6); NT-LPL (lane 3), ABD-LPL (lane 4), and HSV-TK (lane 7). Lysates were immunoprecipitated with an antibody to LPL (lanes 1-7), HA (FIG. 2D) or non-immune serum (NI; FIG. 2A and FIG. 2D). The immunoprecipitates were subjected to 10% (FIG. 2A) or 15% (FIG. 2D) SDS-PAGE and immunoblotted with an antibody to phosphoserine (p-Serine; FIG. 2A and FIG. 2D—lanes 1 and 2). Phosphorylated transduced LPL peptides and endogenous LPL protein are indicated in FIG. 2A and FIG. 2D. Stripping and reblotting of blot A with an antibody to LPL showed endogenous LPL and transduced FL-LPL (FIG. 2B). Stripping and reblotting of blot D (left) with an antibody to HA shows the immunoprecipitated levels of transduced NT-LPL peptides (lane 4). Equal amount of total protein (Input) used for immunoprecipitation was assessed by direct immunoblotting of the lysates with a GAPDH antibody (FIG. 2C and FIG. 2D—lanes 5 and 6). The results shown are representative of three different experiments from three different osteoclast preparations.

FIG. 3A through FIG. 3H, depicts the results of example experiments demonstrating the effect of transduction of indicated TAT-LPL peptides on the formation of NSZs and total cellular F-actin content. Osteoclasts transduced with indicated LPL peptides were plated on dentine slices and incubated for 3-4 hours with TNF-α. Staining was performed with rhodamine-phalloidin for actin. Confocal images of osteoclasts are shown (FIG. 3A-FIG. 3F). Arrows and arrowheads point to big and small NSZs, respectively. Wavy arrows point to podosome-like structures. Scale bar-25 µm. The number of small (blue bar) and big (orange bar) NSZs were counted in approximately 100 osteoclasts and provided as NSZs/OC in a graph (FIG. 3G). The data shown are the mean±SD of one of the three experiments performed with the same results. *p<0.05 versus HSV-TK transduced cells. F-actin content levels were determined by rhodamine phalloidin binding to osteoclasts treated with anti-TNFR1 antibody as well as transduced or untransduced with indicated TAT-LPL peptides (FIG. 3). F-actin content of the 0-min cells was assigned a value of 1.0 and all other values were expressed relative to the 0-mins values. Values plotted are mean±SD from three experiments *p<0.05 untreated (−) or HSV-TK transduced cells.

FIG. 4A through FIG. 4G, depicts the results of example experiments demonstrating the analysis of the formation of seating rings and resorption in osteoclasts. Osteoclasts transduced with indicated TAT-fused HSV-TK (FIG. 4A) and LPL (FIG. 4B-FIG. 4E) peptides were plated on dentine slices and incubated for 10-12 hours with TNF-α. Some cultures were treated with a neutralizing antibody to TNFR-1 (FIG. 4FE). Confocal microscopy images of osteoclasts stained for actin (red) is shown. The reflected light in green is dentine. Overlay images show the distribution of actin protein (red) in osteoclasts plated on dentine slices (green). Resorption pits were found underneath where sealing rings were found in osteoclasts (indicated by arrows in red panels; FIG. 4A-FIG. 4C). Resorption pits were outlined with white lines in green panels (FIG. 4A-FIG. 4C). Asterisks indicate punctuate podosome-like structures in osteoclasts transduced with NT-LPL (FIG. 4E) or treated with a neutralizing antibody to TNFR-1 (FIG. 4F). Scale bar-25 µm. These results represent one of the three experiments performed with the similar results. The number of sealing rings formed in response to indicated treatments is provided as a graph in FIG. 40. Sealing rings were counted in >100 osteoclasts and are provided as N sealing rings/OC; mean±SD. *p<0.05 versus HSV-TK transduced cells. Data provided are the representative of at least three independent experiments with comparable results.

FIG. 5A through FIG. 5G, depicts the results of example experiments demonstrating the effects of transduced TAT-LPL peptides on resorption by osteoclasts. Osteoclasts transduced with indicated TAT-fused peptides (FIG. 5A through FIG. 5E) or treated with a neutralizing antibody to TNFR-1 (FIG. 5F) were cultured on dentine slices for 10-12 hours in the presence of TNF-α. Pits were scanned in a Bio-Rad confocal microscopy. Scale bar-25 µm. Resorbed area is seen as dark areas. Statistic measurements for the pit area are provided as a graph in FIG. 5G. **p<0.01; *p<0.05 versus HSV-TK transduced cells. The resorbed pit areas (20-25 pits/slice) were quantified and data were compiled from four slices per treatment. The data showed (FIG. 5i) are the mean±SD) of one experiment performed. Experiments were repeated three times with three different osteoclast preparations.

FIG. 6B depicts the results of experiments demonstrating the effect of TAT-fused LPL peptides on actin distribution in podosomes and migration. FIG. 6A depicts actin staining with rhodamine phalloidin. Confocal microscopy analysis of the actin stained cells is shown. Scale bar-25 µm. FIG. 6B depicts the results of a transwell migration assay. Data are presented as the number of cells per migrated field (mean±SD) from one experiment of the three experiments performed with three different osteoclast preparations.

FIG. 7A through FIG. 7D, depicts the results of example experiments demonstrating the significance of LPL phosphorylation on NSZs formation using different TAT-fused proteins. Osteoclasts transduced with indicated LPL peptides were plated on dentine slices and incubated fox 3-4 hours with TNF-α. Distributions of transduced proteins and actin were determined by staining with an antibody to HA (green) and rhodamine phalloidin (red), respectively. Images shown were obtained using confocal microscopy. Localization of LPL peptides and their effects on the formation of NSZs formation are shown in multiple osteoclasts at a lower magnification. Arrows indicate NSZs. Scale bar-50 µm FIG. 8, comprising FIG. 8A: Amino acid sequences of TAT-fused sNT-LPL (10aa) and control TAT alone (11aa) peptides are shown: P1) unsubstituted ($S5S7$); P2) double substituted (S5S7 to A5A7); P3) Ser-5 substituted with Ala (A5S7); P4) Ser-7 substituted with Ala (S5A7); P5) scrambled; P6) control TAT alone peptide. FIG. 8B and FIG. 8C: Immunoprecipitation and immunoblotting analyses: Equal amount of osteoclast lysates were immunoprecipitated with an antibody to LPL and subjected to immunoblotting (IB) with a p-Serine antibody (top). This blot was stripped and blotted with an LPL antibody (FIG. 88; middle). An equal amount of total protein (Input) used for immunoprecipitation was assessed by direct immunoblotting of lysates with a GAPDH antibody. These results represent one of the three experiments performed with the similar results. Percent inhibition of phosphorylation of cellular LPL with indicated peptides is provided as a graph. *p<0.01; *p<0.05 versus double substituted (A5A7), scrambled, or TAT alone-peptide transduced cells. The data shown are the mean±SD of three different immunoblots. FIG. 8D: The effect of sNT-LPL peptides on F-actin content: The F-actin content was determined in osteoclasts transduced with indicated peptides by rhodamine-phalloidin binding. Fold change in F-actin levels are provided. The F-actin content of the 0-min cells was assigned a value of 1.0 and all other values were expressed relative to the 0-mins values. Values plotted are mean±SD from three experiments **p<0.01; *p<0.05 versus P2, P5, or P6 peptide transduced cells.

FIG. 9A and FIG. 9B, depict the result of example experiments demonstrating that peptide P1 reduces the formation of NSZs considerably as compared with P2, P5, and P6 peptides. Confocal microscopy analysis (FIG. 9A) was done in osteoclasts stained for actin with rhodamine phalloidin (red). Arrows point to NSZs and Asterisks indicate podosome-like structures. Scale bar-25 µm. The number of NSZs were counted in >100 osteoclasts and presented as #/OC in the graph (FIG. 9B). Data provided are mean±k SD from one experiment. **p<0.01 versus mutated (P2), scrambled (P5), or TAT peptide (P6) transduced cells. Resorption assay was repeated several times with different osteoclast preparations and obtained similar results.

FIG. 10A and FIG. 10B, depicts the results of example experiments demonstrating that peptide P1 reduces the resorption of dentine matrix considerably as compared with P2, P5, and P6 peptides. All treatments were done in triplicates or quadruplicates for 12-16 hours and pits were viewed under 40× objective in a phase contrast microscope and photographed (FIG. 10A). Arrowheads in FIG. 10A point to superficial pits. The resorbed pit areas (20-25 pits/slice) were quantified and data were compiled from four slices per treatment. The data shown are the mean±SD of one experiment performed (FIG. 10B). Experiments were repeated three times with three different osteoclast preparations. *p<0.01 versus mutated (P2), scrambled (P5), or TAT peptide (P6) transduced cells.

FIG. 11A through FIG. 11F, depicts the results of example experiments demonstrated that peptide P1 diminishes not only the formation of NSZs but also the sealing ring in osteoclasts cultured on dentine matrix. Immunostaining was done with an antibody to LPL (green) and integrin αv (red). LPL staining was observed in patches at 3 hours in osteoclasts treated with P5 (FIG. 11D). Colocaliation of integrin and LPL (yellow; indicated by arrows) was observed at 6 h (FIG. 11E) and 10 hours (FIG. 11F) in the aggregates (presumably NSZs) in osteoclasts transduced with the P5 peptide. The mature sealing ring was observed from 10 hours onwards and only integrin αv (red) is present in the sealing ring (FIG. 11F; indicated by a wavy arrow). Colocalization is significantly reduced in mature sealing rings. Neither NSZs nor sealing rings were observed in osteoclasts transduced with P1 peptide (FIG. 11A-FIG. 11C). Red shows the distribution of integrin αv. Diffuse and plasma membrane distribution of integrin was observed (FIG. 11A-FIG. 11C, red panels) in P1 transduced osteoclasts.

FIG. 12A through FIG. 12D, depicts the results of example experiments demonstrating that migration and podosome organization are unaffected by sNT-LPL peptides in mouse osteoclasts: Motility (FIG. 12A-FIG. 12C) and podosome organization (FIG. 12D) was assessed in osteoclasts treated with peptides (P1, P2, P5, and P6). FIG. 12A-FIG. 12C: Phagokinesis (FIG. 12A and FIG. 12B) and transwell migration (FIG. 12C) assays. The data in FIG. 12B are mean±SD of 20-30 cell tracks (clear areas) represented as area migrated in mm. The data in FIG. 12C are mean±SD of migrated cells and provided as cells/filed, FIG. 12D; Confocal microscopy analysis of rhodamine-phalloidin stained cells. None of the indicated peptides has any effect on osteoclast migration (FIG. 12A-FIG. 12C) or podosome organization (FIG. 12D). Podosome organization is seen at the periphery of osteoclasts. These results represent one of the three experiments performed with the similar results.

FIG. 13A through FIG. 13M, depicts the results of example experiments demonstrating that analyses in osteoclasts derived from RAW macrophage cell line corroborates the observations in mouse BM cells, FIG. 13A: Immunoblotting (IB) with an LPL antibody: Osteoclasts derived from RAW cells were incubated with bone particles (+) and TNF-α for different time periods (hours) as indicated at the bottom of the figure immunoblotting analyses with an LPL antibody is shown (FIG. 13; top). This blot was stripped and blotted with a GAPDH antibody (bottom). Osteoclasts untreated with bone particles but treated with TNF-α were used as controls (−; lane 1). Osteoclasts treated with bone particles (+) and TNF-α for an indicated time-period (hours) are shown in lanes 2-5. FIG. 13B: Immunoprecipitation and immunoblotting analyses: Equal amount of osteoclast lysates were immunoprecipitated with an antibody to LPL and subjected to IB with a p-Serine antibody (FIG. 13B; top). This blot was stripped and blotted with an LPL antibody (FIG. 13B; middle). An equal amount of protein used for immunoprecipitation was assessed by direct immunoblotting of total lysates (input) with a GAPDH antibody (bottom). These results represent one of the three experiments performed with the similar results. FIG. 13C-FIG. 13H: Confocal microscopy analyses in osteoclasts treated with peptides P1 (FIG. 13C-FIG. 13E) and P5 (FIG. 13F-FIG. 13H) and stained for actin with rhodamine phalloidin (red): Arrows point to NSZs (FIG. 13F) and wavy arrows point to sealing rings (FIG. 13G) in P5 peptide treated osteoclasts plated on dentine slices. These features are significantly reduced or not observed in P peptide treated osteoclasts (FIG. 13C and FIG. 13D). An arrowhead in FIG. 13C points to a small actin aggregate. Open arrows in FIG. 13E and FIG. 13H point to podosomes in P1 and P5 treated osteoclasts plated on glass coverslips. Scale bar-25 μm.

FIG. 14A through FIG. 14F, depicts the results of example experiments demonstrating the mineralization and expression of osteogenic markers (Collagen. RUNX2, and Osterix) by osteoblasts is unaffected by sNT-LPL peptides (P1-P6). FIG. 14A-FIG. 14D: Mineralization was assessed by Alizarin Red Staining (ARS) in cells fixed at day 7 of culture. ARS of MC3T-E1 (FIG. 14A and FIG. 14B) and UMR-106 (FIG. 14C and FIG. 14D) cells cultured for seven days is shown. Each peptide treatment was done in duplicates for MC3T3 (FIG. 14A) and triplicates for UMR-106 (FIG. 14C) cells. The plates were scanned in an EPSON Perfection V200 Photo scanner (FIG. 14A and FIG. 14C). Representative magnified images of mineralized nodules are shown (FIG. 14B and FIG. 14D). Magnified images were taken in a phase contrast microscopy with a 10× and 20× objective for FIG. 14B and FIG. 14D, respectively. Cells grown in osteogenic medium (OM) and basal medium (BM) without peptides (−) were used as controls. FIG. 14E: Analysis of ALP activity in UMR 106 cells. Data shown are mean±SD (n=3). Minus (−) indicates cells grew in OM but untreated with the peptide. There is no significant statistical difference between the groups FIG. 14F: Western blot analysis for the expression of osteogenic biomarkers such as Collagen 1. RUNX2 and osterix. Lysates made from osteoblasts treated with indicated peptides for 7 days were used for the analysis. Immunoblotting with a GAPDH antibody was used as loading control. Results in FIG. 14A-FIG. 14D and FIG. 14F represent one of the two experiments performed with the similar results.

FIG. 17A through FIG. 17D, depicts the analysis of nanoparticle size, distribution and morphology. A narrow size distribution of PLGA-PEG_P1 (FIG. 17A) PLGA-PEG_P5 (FIG. 17B) nanoparticles is observed, measured by dynamic light scattering. TEM images show well dispersed round shaped PLGA-PEG_P1 (FIG. 17C) and PLGA-PEG_P5 (FIG. 17D) nanoparticles. Scale bars=200 nm.

FIG. 19 depicts a table displaying the physiochemical characterization of nanoparticles.

FIG. 8B and FIG. 13B demonstrate that transduction of TAT-fused sNT-LPL-P1 peptide has the potential to reduce the phosphorylation of endogenous LPL; however, did not change the cellular levels of LPL. Similarly, uptake of PLGA-PEG_P1 (NP1) peptide significantly decreased the phosphorylation of endogenous LPL as compared with PLGA-PEG_P5 (NP5) peptide. The decrease was maximum at 4 hours. The effect of the P1 peptide on the inhibition of endogenous LPL is shown in lane 2. Although PLGA-PEG_P1 (NP1) displays a decrease in endogenous LPL at 6 hours, the decrease was more at 4 hours at which time an increase in the level of LPL was observed in the time-course study (FIG. 20).

DETAILED DESCRIPTION

Figure 1:
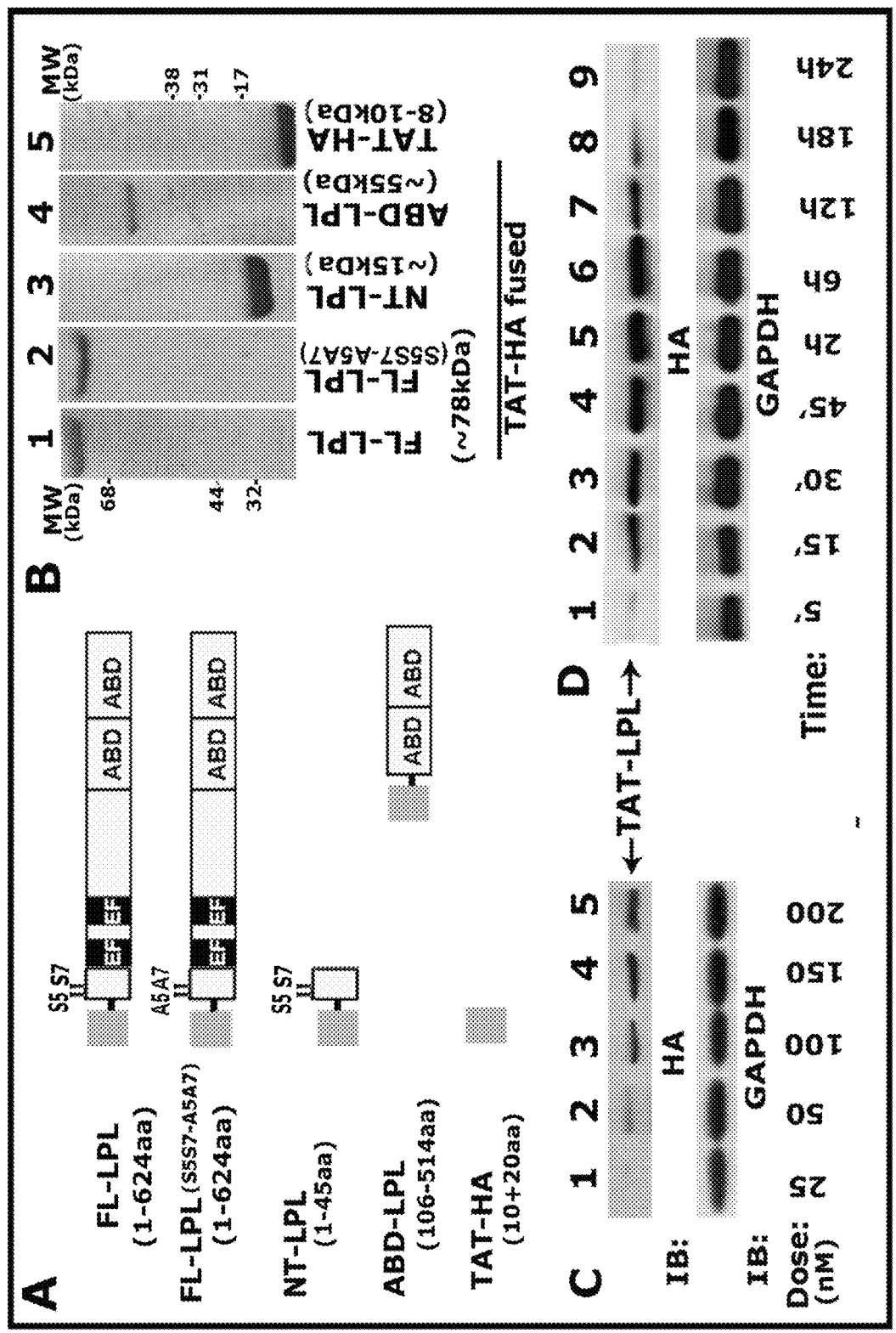
FIG. 1, comprising

The present invention provides compositions and methods for inhibiting L-plastin (LPL) activity. In some aspects, the inhibition of LPL activity is used to inhibit, prevent, or reduce bone resorption activity of osteoclasts. For example, it is demonstrated herein that LPL plays a role in actin bundling and bone resorption in osteoclasts, and that inhibiting LPL activity or LPL phosphorylation inhibits bone resorption. The present invention can be used to treat or prevent diseases or disorders related to bone resorption, including, but not limited to osteoporosis and periodontal disease.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" of the severity of a sign or symptom of the disease or disorder, the frequency with which such a sign or symptom is experienced by a patient, or both, is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "effective amount" of a compound is that amount of compound which is sufficient to provide an effect to the subject or system to which the compound is administered.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "patient," "subject." "individual," and the like are used interchangeably herein, and refer to any animal, or cells thereof whether in vitro or in situ, amenable to the methods described herein. In some embodiments, the patient, subject or individual is a human.

"Parenteral" administration of a composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the an as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "therapeutic" treatment is a treatment administered to a subject who exhibits signs or symptoms of a disease or disorder, for the purpose of diminishing or eliminating the frequency or severity of those signs or symptoms.

As used herein, "treating a disease or disorder" means reducing the frequency or severity, or both, of at least one sign or symptom of the disease or disorder experienced by a patient.

The phrase "therapeutically effective amount," as used herein, refers to an amount that is sufficient or effective to prevent or treat (delay or prevent the onset of, prevent the progression of, inhibit, decrease or reverse) a disease or disorder, including alleviating signs and/or symptoms of such diseases and disorders.

To "treat" a disease or disorder as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the at including, but not limited to, linear polynucleotides, polynucleotides associated with ionic or amphiphilic compounds, plasmids, and viruses.

Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In one embodiment, the invention provides compositions comprising an inhibitor of LPL expression or activity. In some embodiments, the compositions inhibit, reduces, or prevents LPL phosphorylation, for example LPL phosphorylation at Ser 5, Ser 7, or both. In some embodiments, the inhibitor comprises any compound, molecule, or agent that reduces, inhibits, or prevents LPL expression or activity. In some embodiments, the inhibitor comprises any compound, molecule, or agent that reduces, inhibits, or prevents LPL phosphorylation. In some embodiments, the inhibitor comprises nucleic acid molecule, a peptide, a small molecule, a siRNA, a ribozyme, an antisense nucleic acid, an antagonist, an aptamer, a peptidomimetic, or any combination thereof.

In some embodiments, the inhibitor comprises a peptide comprising an N-terminal fragment of LPL, or a variant thereof, which competes with endogenous LPL and thereby inhibits LPL activity. In some embodiments, the inhibitor comprises a fusion peptide comprising a transduction domain and an inhibitor domain, wherein the inhibitor domain comprises an N-terminal fragment of LPL, or a variant thereof, which competes with endogenous LPL and thereby inhibits LPL activity. In some embodiments, the inhibitor comprises an amino acid sequence selected from the group consisting of SEQ ID NO: 1, SEQ ID NO: 2, SEQ ID NO: 3, SEQ ID NO: 4 or SEQ ID NO: 34. In some embodiments, the composition comprises a delivery vehicle, including but not limited to, a nanoparticle, microparticle, polymerosomes, micelle, or the like, which encapsulates the inhibitor and is capable of releasing the inhibitor.

In one aspect, the present invention provides a method for inhibiting LPL expression or activity in a cell, such as an osteoclast. In one embodiment, the present invention provides methods for reducing, inhibiting, or preventing bone resorption. In some embodiments, the methods are used to treat or prevent a disease or disorder associated with bone resorption or bone loss. Exemplary diseases and disorders include, but are not limited to, osteoporosis, idiopathic primary osteoporosis, age-related osteoporosis, glucocorticoid-induced osteoporosis, Hajdu-Chency syndrome, osteolysis, post-transplant bone disease, Paget's disease of bone, bone loss associated with cancer, periodontal disease, and periodontitis.

Compositions

In one embodiment, the present invention provides compositions for inhibiting LPL. In some embodiments, the composition reduces, inhibits, or prevents LPL expression, activity, or both. In some embodiments, the composition reduces, inhibits or prevents LPL phosphorylation.

In various embodiments, the composition comprises an inhibitor of LPL. In some embodiments, the inhibitor of LPL is any compound, molecule, or agent that reduces, inhibits, or prevents the expression, activity, or function of LPL. Thus, an inhibitor of LPL is any compound, molecule, or agent that reduces LPL expression, activity, or both. In various embodiments, the inhibitor of LPL is a nucleic acid molecule, a peptide, a small molecule, a siRNA, a ribozyme, an antisense nucleic acid, an antagonist, an aptamer, a peptidomimetic, or any combination thereof.

In some embodiments, the inhibitor comprises a peptide comprising an N-terminal fragment of LPL, or a variant thereof, which competes with endogenous LPL and thereby inhibits LPL activity. In some embodiments, the inhibitor comprises a fusion peptide comprising a transduction domain and an inhibitor domain, wherein the inhibitor domain comprises an N-terminal fragment of LPL, or a variant thereof, which competes with endogenous LPL and thereby inhibits LPL activity. In some embodiments, the inhibitor comprises an amino acid sequence selected from the group consisting of SEQ ID NO: 1, SEQ ID NO: 2, SEQ ID NO: 3, SEQ ID NO: 4 or SEQ ID NO: 34.

Small Molecule Inhibitors

In some embodiments, the inhibitor is a small molecule. When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule inhibitor of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecule inhibitor of the invention comprises an analog or derivative of an inhibitor described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used to treat an autoimmune disease or disorder.

In one embodiment, the small molecule inhibitors described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Polypeptide Inhibitors

In one embodiment, the inhibitor comprises a peptide that reduces, inhibits, or prevents LPL expression, activity or both. For example, in some embodiments, the inhibitor comprises a peptide that reduces, inhibits, or prevents LPL phosphorylation, for example at Ser 5S, Ser 7, or both Ser 5 and Ser 7.

In one embodiment, the peptide inhibitor comprises an N-terminal fragment, or variant thereof, of LPL. For example, in certain embodiments, the peptide inhibitor comprises an N-terminal fragment, or variant thereof, comprising the at least first 5, the at least first 10, the at least first 15, the at least first 20, the at least first 25, the at least first 30, the at least first 35, the at least first 40, the at least first 45, the at least first 50, the at least first 75, the at least first 100, the at least first 125, or the at least first 150 residues of LPL. For example, in certain embodiments, the peptide inhibitor comprises an N-terminal fragment, or variant thereof, comprising no more than the first 5, no more than the first 10, no more than the first 15, no more than the first 20, no more than the first 25, no more than the first 30, no more than the first 35, no more than the first 40, no more than the first 45, no more than the first 50, no more than the first 75, no more than the first 100, or no more than the first 125, or no more than the first 150 residues of LPL. In certain aspects, the N-terminal fragment of LPL can be derived from any species, isoform or source of LPL. In one embodiment, the N-terminal fragment is derived from the amino acid sequence of full-length LPL as provided in GenBank Accession No. BC010271.

In one embodiment, the peptide inhibitor comprises the N-terminal fragment of LPL comprising the amino acid sequence of MARGSVSDEE (SEQ ID NO: 1), which is the first 10 residues of LPL.

In one embodiment, the peptide inhibitor comprises a variant of an N-terminal fragment of LPL, comprising the amino acid sequence of MARGAVADEE (SEQ ID NO: 2), which is the first 10 residues of LPL and comprising serine to alanine mutations at positions 5 and 7.

In one embodiment, the peptide inhibitor comprises a variant of an N-terminal fragment of LPL, comprising the amino acid sequence of MARGAVSDEE (SEQ ID NO: 3), which is the first 10 residues of LPL and comprising a serine to alanine mutation at position 5.

In one embodiment, the peptide inhibitor comprises a variant of an N-terminal fragment of LPL, comprising the amino acid sequence of MARGSVADEE (SEQ ID NO: 4), which is the first 10 residues of LPL and comprising a serine to alanine mutation at position 7.

In one embodiment, the peptide inhibitor comprises the N-terminal fragment of LPL comprising the first 45 residues of LPL. For example, in one embodiment, the N-terminal fragment of LPL comprises the amino acid sequence of:

(SEQ ID NO: 34)
MARGSVSDEEMMELREAFAKVDTDGNGYISFNELNDLFKAACLPL.

In certain embodiment, the peptide inhibitor is a fusion peptide. For example, in one embodiment, the fusion peptide comprises a transduction domain and an inhibitor domain, wherein the inhibitor domain comprises an N-terminal fragment, or variant thereof, of LPL, as described above. In one embodiment, the inhibitor domain of the fusion peptide comprises at least one of SEQ ID NO: 1, SEQ ID NO: 2, SEQ ID NO: 3, SEQ ID NO: 4 or SEQ ID NO: 34.

The transduction domain comprises any compound or agent that facilitates the entry of the peptide inhibitor into a cell. In one embodiment, the transduction domain comprises a cell penetrating peptide. Exemplary transduction domains or cell penetrating peptides include, but are not limited to, a protein transduction domain corresponding to residues 47-57 of human immunodeficiency virus-1 (HIV-1) TAT; or variations thereof including RKKRRQRRRPP (SEQ ID NO: 5), YGRKKRRQRRR (SEQ ID NO: 6), QRRQRRKKRGY (SEQ ID NO: 7), RKKRRQRRR (SEQ ID NO: 8), THRL-PRRRRRR (SEQ ID NO: 9); and GGRRARRRRRR (SEQ ID NO: 10); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an *Drosophila* Antennapedia protein transduction domain (Noguchi et al. (2003) Diabetes 52(7): 1732.1737); a mastoparan transduction domain (T. Higashijima et al., (1990) J. Biol. Chem. 265:14176); a tuncated human calcitonin peptide (Trehin et al. (2004) Pharm, Research 21:1248-1256); polylysine (Wender et al. (2000) Proc. Nat, Acad. Sci. USA 97:13003-13008); RRQRRTSKLMKR (SEQ ID NO: 1); Transportan GWTLNSAGYLLGKINLKALAALAKKIL (SEQ ID NO: 12); KALAWEAKLAKAKALAKALAKHLAKALAKA-LKCEA (SEQ ID NO: 13); and RQIKIWFQNRRMKWKK (SEQ ID NO: 14). In certain embodiments, the transduction domain comprises a peptide capable of crossing the cell membrane by receptor-mediated transcytosis. Exemplary peptides that can direct entry of the fusion peptide via receptor-mediated transcytosis include, but are not limited to, EGF (epidermal growth factor)-derived peptides, such as CMHIESLDSYTC (SEQ ID NO: 15) and CMYIEALDKYAC (SEQ ID NO: 16); TGF-beta (transforming growth factor beta)-derived peptides; peptides derived from PDGF (platelet-derived growth factor) or PDGF-2; peptides derived from IGF-I (insulin-like growth factor) or IGF-II; and FGF (fibroblast growth factor)-derived peptides, and all or a portion of, e.g., a histone, insulin, transferrin, basic albumin, prolactin and insulin-like growth factor I (IGF-I), insulin-like growth factor II (IGF-II) or other growth factors. Additional transduction domains include the cell-penetrating peptides described in Madani et al., 2011, J Biophys, Article ID 414729; including but not limited to R9 (RRRRRRRRR (SEQ ID NO: 17)), TAT(48-60) (GRKKRRQRRRPPQ (SEQ ID NO: 18)), Penetratin (RQIKIWFQNRRMKWKK (SEQ ID NO. 19)), Pen-Arg (RQIRIWFQNRRMRWRR (SEQ ID NO: 20)); pVEC (LLIILRRRIRKQAHAHSK (SEQ ID NO: 21)); M918 (MVTVLFRRLRIRRACGPPRVRV (SEQ ID NO: 22)); and TP10 (AGYLLGKINLKALAALAKKIL (SEQ ID NO: 23)).

In some embodiments, the peptide inhibitor comprises a fusion peptide comprising a TAT transduction domain linked to an inhibitor domain, wherein the inhibitor domain is at least one of SEQ ID NO: 1, SEQ ID NO: 2. SEQ ID NO: 3, SEQ ID NO: 4 or SEQ ID NO: 34. In one embodiment, the peptide inhibitor comprises a fusion peptide comprising a TAT transduction domain comprising SEQ ID NO: 5, linked to an inhibitor domain, wherein the inhibitor domain is at least one of SEQ ID NO: 1, SEQ ID NO: 2, SEQ ID NO: 3, SEQ ID NO: 4 or SEQ ID NO: 34.

The invention should also be construed to include any form of a peptide variant having substantial homology to an amino acid sequence disclosed herein. In one embodiment, a protein variant is at least about 50% homologous, at least about 70% homologous, at least about 80% homologous, at least about 90% homologous, at least about 95% homologous, or at least about 99% homologous to an amino acid sequence disclosed herein.

The invention should also be construed to include any form of a fragment having a substantial length of an amino acid sequence disclosed herein. In one embodiment, a fragment is at least about 50% of the length, at least about 70% of the length, at least about 80% of the length, at least about 90% of the length, at least about 95% of the length, or at least about 99% of the length of an amino acid sequence disclosed herein.

The invention should also be construed to include any form of a fragment of a protein variant, having both substantial homology to and a substantial length of an amino acid sequence disclosed herein. In one embodiment, a fragment of a protein variant is between 50% and 99% homologous to an amino acid sequence disclosed herein, and is between 50% and 99% of the length of an amino acid sequence disclosed herein.

The peptide may alternatively be made by recombinant means or by cleavage from a longer protein or peptide. The peptide may be confirmed by amino acid analysis or sequencing.

The variants of the proteins according to the present invention may be (i) one in which one or more of the amino acid residues are substituted with a conserved or non-conserved amino acid residue (e.g., a conserved amino acid residue) and such substituted amino acid residue may or may not be one encoded by the genetic code, (ii) one in which there are one or more modified amino acid residues, e.g., residues that are modified by the attachment of substituent groups, (iii) one in which the protein comprises an alternative splice variant of the proteins or domains described herein, (iv) fragments of the proteins or domains described herein and/or (v) one in which the protein is fused with another protein or peptide, such as a leader or secretory sequence or a sequence which is employed for purification (for example, His-tag) or for detection (for example, Sv5 epitope tag). The fragments include proteins or peptides generated via proteolytic cleavage (including multi-site proteolysis) of an original sequence. Variants may be post-translationally, or chemically modified. Such variants are deemed to be within the scope of those skilled in the at from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, e.g., different from the original sequence in less than 40% of residues per segment of interest, different from the original sequence in less than 25% of residues per segment of interest, different by less than 10% of residues per segment of interest, or different from the original protein sequence in just a few residues per segment of interest and at the same time sufficiently homologous to the original sequence to preserve the functionality of the original sequence. The present invention includes amino acid sequences that are at least 60%, 65%, 70%, 72%, 74%, 76%, 78%, 80%, 90%, or 95% similar or identical to the original amino acid sequence. The degree of identity between two polypeptides may be determined using computer algorithms and methods that are widely known for the persons skilled in the art. The identity between two amino acid sequences may be determined by using the BLASTP algorithm (BLAST Manual, Altschul, S., et al., NCBI NLM NIH Bethesda, Md. 20894, Altschul, S., et al., J. Mol. Biol. 215: 403-410 (1990)).

The protein of the invention may or may not be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction. A polypeptide or protein of the invention may be phosphorylated using conventional methods such as the method described in Reedijk et al. (The EMBO Journal 1(4):1365, 1992).

The protein of the invention may include unnatural amino acids formed by post-translational modification or by introducing unnatural amino acids during translation. A variety of approaches are available for introducing unnatural amino acids during polypeptide translation.

A protein of the invention may be conjugated with other molecules, such as polyethylene glycol (PEG). This may be accomplished by inserting cysteine mutations or unnatural amino acids that can be modified with a chemically reactive PEG derivative. In one embodiment, the protein is conjugated to other proteins, to prepare fusion proteins. This may be accomplished, for example, by the synthesis of N-terminal or C-terminal fusion proteins provided that the resulting fusion protein retains the functionality of the protein inhibitor described herein.

Cyclic derivatives of the proteins of the invention are also part of the present invention. Cyclization may allow the protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position, it may be desirable to produce a cyclic protein which is more flexible than the cyclic proteins containing peptide bond linkages as described above. A more flexible protein may be prepared by introducing cysteines at the right and left position of the polypeptide and forming a disulfide bridge between the two cysteines. The two cysteines are arranged so as not to deform the beta-sheet and turn. The protein is more flexible as a result of the length of the disulfide linkage and the smaller number of hydrogen bonds in the beta-sheet portion. The relative flexibility of a cyclic protein can be determined by molecular dynamics simulations.

In some embodiments, the peptide inhibitor comprises a targeting domain capable of directing the resulting peptide to a desired cellular component or cell type or tissue. In certain embodiments, the peptide inhibitor comprises additional amino acid sequences or domains. The chimeric or fusion proteins are recombinant in the sense that the various components are from different sources, and as such are not found together in nature (i.e., are heterologous).

In one embodiment, the targeting domain can be a membrane spanning domain, a membrane binding domain, or a sequence directing the peptide inhibitor to associate, for example, with vesicles or with the cell surface. In one embodiment, the targeting domain can target a protein to a particular cell type or tissue. For example, the targeting domain can be a cell surface ligand or an antibody against cell surface antigens of a target tissue. A targeting domain may target a peptide inhibitor of the invention to a cellular component.

A protein of the invention may be synthesized by conventional techniques. For example, the proteins may be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford ill. (1984) and G. Barany and R. B. Merrifield. The Peptides: Analysis Synthesis, Biology editors E. Gross and J. Meienhofer Vol. 2 Academic Press, New York, 1980, pp. 3.254 for solid phase synthesis techniques; and M Bodansky, Principles of Peptide Synthesis, Springer-Verlag, Berlin 1984, and E. Gross and J. Meienhofer, Eds., The Peptides: Analysis. Synthesis, Biology, suprs, Vol 1, for classical solution synthesis). By way of example, a polypeptide of the invention may be synthesized using 9-fluorenyl methoxycarbonyl (Fmoc) solid phase chemistry with direct incorporation of phosphothreonine as the N-fluorenylmethoxy-cabonyl-O-benzyl-L-phospho-threonine derivative.

N-terminal or C-terminal fusion proteins comprising a peptide or protein of the invention, conjugated with at least one other molecule, may be prepared by fusing, through recombinant techniques, the N-terminal or C-terminal end of the peptide or protein, and the sequence of a selected protein or selectable marker with a desired biological function. The resultant fusion proteins contain the peptide of the invention fused to the selected protein or marker protein as described herein. Examples of proteins which may be used to prepare fusion proteins include immunoglobulins and regions thereof, glutathione-S-transferase (GST), hemagglutinin (HA), and truncated myc.

A protein of the invention may be developed using a biological expression system. The use of these systems allows the production of large libraries of random sequences and the screening of these libraries for sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et at 1990, Proc. Natl. Acad. Sci. USA, 87:6378). Libraries may also be constructed by concurrent synthesis of overlapping peptides (see U.S. Pat. No. 4,708,871).

The protein of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

The present invention further encompasses fusion proteins in which the protein of the invention or fragments thereof, are recombinantly fused or chemically conjugated (including both covalent and non-covalent conjugations) to heterologous proteins (i.e., an unrelated protein or portion thereof, e.g., at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences.

In one example, a fusion protein in which a protein of the invention or a fragment thereof can be fused to sequences derived from various types of immunoglobulins. For example, a polypeptide of the invention can be fused to a constant region (e.g., hinge, CH2, and CH3 domains) of human IgG or IgM molecule, for example, as described herein, so as to make the fused protein or fragments thereof more soluble and stable in vivo. In another embodiment, such fusion proteins can be administered to a subject so as to inhibit interactions between a ligand and its receptors in vivo. Such inhibition of the interaction will block or suppress signal transduction which triggers certain cellular responses.

In one embodiment, the peptide inhibitor comprises a domain that enhances stability or half-life of the fusion protein. For example, in one embodiment, the domain comprises at least one region of an immunoglobulin, human serum albumin (HSA), or a peptide or antibody fragment that binds to immunoglobulin, HSA, the erythrocyte cell surface, or the neonatal Fc receptor. In one embodiment, the domain comprises a fragment or variant of at least one region of an immunoglobulin. For example, in one embodiment, the domain comprises an Fc region of an immunoglobulin. Exemplary immunoglobulins include, but is not limited to, IgG1, IgG2, IgG3, IgG4, IgM, IgA, IgE, and IgD.

In one aspect, the fusion protein comprises a polypeptide of the invention which is fused to a heterologous signal sequence at its N-terminus. For example, the signal sequence naturally found in the protein of the invention can be replaced by a signal sequence which is derived from a heterologous origin. Various signal sequences are commercially available. For example, the secretory sequences of melittin and human placental alkaline phosphatase (Stratagene; La Jolla, Calif.) are available as eukaryotic heterologous signal sequences. As examples of prokaryotic heterologous signal sequences, the phoA secretory signal (Sambrook, et al., supra; and Current Protocols in Molecular Biology, 1992, Ausubel, et al., eds., John Wiley & Sons) and the protein A secretory signal (Pharmacia Biotech; Piscataway, N.J.) can be listed. Another example is the gp67 secretory sequence of the baculovirus envelope protein (Current Protocols in Molecular Biology, 1992, Ausubel, et al., eds., John Wiley & Sons).

In another embodiment, a protein of the invention can be fused to tag sequences, e.g., a hexa-histidine peptide, such as the tag provided in a pQE vector (QIAGEN, Inc., 9259 Eton Avenue, Chatsworth, Calif., 91311), among others, many of which are commercially available. As described in Gentz, et al., 1989, Proc. Natl. Acad. Sci. USA 86:821-824, for instance, hexa-histidine provides for convenient purification of the fusion protein. Other examples of peptide tags are the hemagglutinin "HA" tag, which corresponds to an epitope derived from the influenza hemagglutinin protein (Wilson, et al., 1984, Cell 37:767) and the "flag" tag (Knappik, et al., 1994, Biotechniques 17(4):754-761). These tags are especially useful for purification of recombinantly produced proteins of the invention.

Nucleic Acid Molecules

In one embodiment, the present invention provides a composition comprising an isolated nucleic acid sequence encoding a peptide inhibitor described herein. For example, in one embodiment, the composition comprises an isolated nucleic acid molecule encoding a peptide or fusion peptide that reduces, inhibits, or prevents LPL expression, activity or both.

In one embodiment, the composition comprises an isolated nucleic acid sequence encoding a biologically functional fragment of a peptide inhibitor described herein. As would be understood in the art, a biologically functional fragment is a portion or portions of a full-length sequence that retains a biological function of the full-length sequence.

In various embodiments, the isolated nucleic acid sequence encodes a peptide inhibitor comprising an amino acid sequence selected from the group consisting of SEQ ID NO: 1, SEQ ID NO: 2, SEQ ID NO: 3, SEQ ID NO: 4 and SEQ ID NO: 34.

Further, the invention encompasses an isolated nucleic acid encoding a polypeptide having substantial homology to a protein inhibitor disclosed herein. In some embodiments, the isolated nucleic acid sequence encodes protein inhibitor having at least 75%, 80%, 85%, 90%, 95%, 96%, 97%, 98%, or 99% sequence homology with an amino acid sequence selected from SEQ ID NO: 1, SEQ ID NO: 2, SEQ ID NO: 3, SEQ ID NO: 4 and SEQ ID NO: 34.

The isolated nucleic acid sequence encoding a peptide inhibitor can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA, cDNA, and RNA. For example, in one embodiment, the composition comprises an isolated DNA molecule, including for example, an isolated cDNA molecule, encoding a protein inhibitor or functional fragment thereof. In one embodiment, the composition comprises an isolated RNA molecule encoding a protein inhibitor or a functional fragment thereof.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleoides the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, NH2, NHR, NR2 or ON, wherein R is C1-C6 alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; 0- and N-alkylated nucleotides, e.g., N6-methyl adenosine are suitable. The above modifications may be combined.

In some instances, the nucleic acid molecule comprises at least one of the following chemical modifications: 2'-H, 2'-O-methyl, or 2'-OH modification of one or more nucleotides. In some embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxthyethyl (2-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. The an has referred to rare or unusual, but naturally occurring, RNAs as modified RNAs, see, e.g., Limbach et at (Nucleic Acids Res., 1994, 22-2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, for example different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the invention may be present at one or more of, a phosphate group, a sugar group, backbone, N-terminus, C-terminus, or nucleobase.

In some embodiments, the inhibitor is nucleic acid. In various embodiments, the inhibitor is an siRNA, miRNA, shRNA, or an antisense molecule, which inhibits LPL. In one embodiment, the nucleic acid comprises a promoter/regulatory sequence such that the nucleic acid is capable of directing expression of the inhibitor nucleic acid. Thus, the invention encompasses expression vectors and methods for the introduction of exogenous DNA into cells with concomitant expression of the exogenous DNA in the cells such as those described, for example, in Sambrook et al., (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In another aspect of the invention, LPL, can be inhibited by way of inactivating and/or sequestering LPL. As such, inhibiting the activity of LPL can be accomplished by using a transdominant negative mutant.

In one embodiment, siRNA is used to decrease the level of LPL protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in, the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306311; Timmons et al, 1998, Nature 395; 854; Montgomery et at, 1998, TIG 14 (7):255-258; David R. Engelke, Ed., RNA Interference (RNAi) Nuts & Bolts of RNAi Technology, DNA Press, Eagleville, P A (2003); and Gregory J. Hannon, Ed., RNAi A Guide to Gene Silencing, Cold Spring Harbor Laboratory Press, Cold Spring Harbor, N.Y. (2003). Soutschek et al., (2004, Nature 432:173-178) describe a chemical modification to siRNAs that aids in intravenous systemic delivery. Optimizing siRNAs involves consideration of overall GI/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of LPL using RNAi technology.

In another aspect, the invention includes a vector comprising an siRNA or antisense nucleic acid. In one embodiment, the siRNA or antisense polynucleotide is capable of inhibiting the expression of a target polypeptide, wherein the target polypeptide is LPL. The incorporation of a desired, polynucleotide into a vector and the choice of vectors is well-known in the an as described in, for example, Sambrook et al. (2012), and, in Ausubel et al. (1997), and elsewhere herein.

In some embodiments, the expression vectors described herein encode a short hairpin RNA (shRNA) inhibitor, shRNA inhibitors are well known in the art and are directed against the mRNA of a target, thereby decreasing the expression of the target. In some embodiments, the encoded shRNA is expressed by a cell, and is then processed into siRNA. For example, in certain instances, the cell possesses native enzymes (e.g., dicer) that cleaves the shRNA to form siRNA.

The siRNA, shRNA, or antisense nucleic acid can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense nucleic, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector, Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

By way of illustration, the vector in which the nucleic acid sequence is introduced can be a plasmid, which is or is not integrated in the genome of a host cell when it is introduced in the cell, illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook t al., 2012). In a particular embodiment, the vector is a vector useful for transforming animal cells.

In one embodiment, the recombinant expression vectors may also contain nucleic acid molecules, which encode a peptide or peptidomimetic inhibitor of invention, described elsewhere herein.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring" i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (U.S. Pat. Nos. 4,683,202, 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The recombinant expression vectors may also contain a selectable marker gene, which facilitates the selection of transformed or transfected host cells. Suitable selectable marker genes are genes encoding proteins such as G418 and hygromycin, which confer resistance to certain drugs, β-galactosidase, chloramphenicol acetyltansferase, firefly luciferase, or an immunoglobulin or portion thereof such as the Fc portion of an immunoglobulin, such as IgG. The selectable markers may be introduced on a separate vector from the nucleic acid of interest.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987, Tetrahedron Lett. 28:3539-3542; Stec et al., 1985 Tetrahedron Lett, 26:2191-2194; Moody et at, 1989 Nucleic Acids Res. 12:4769-4782; Eckstein, 1989 Trends Biol. Sci. 14:97-100; Stein. In: Oligodeoxynucleotides. Antisense Inhibitors of Gene Expression. Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

In one embodiment of the invention, an antisense nucleic acid sequence, which is expressed by a plasmid vector is used to inhibit LPL protein expression. The antisense expressing vector is used to transfect a mammalian cell or the mammal itself, thereby causing reduced endogenous expression of LPL.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the an, and is described, for example, in Marcus-Sakura (1988. Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between may be about 10 to about 30, nucleotides. In some embodiments, antisense oligomers are about 15 nucleotides. Antisense oligomers about 10 to about 30 nucleotides are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

In one embodiment of the invention, a ribozyme is used to inhibit LPL protein expression. Ribozymes useful for inhibiting the expression of a target molecule may be designed by incorporating target sequences into the basic ribozyme structure, which are complementary, for example, to the mRNA sequence encoding LPL. Ribozymes targeting LPL, may be synthesized using commercially available reagents (Applied Biosystems, Inc., Foster City, Calif.) or they may be genetically expressed from DNA encoding them.

In one embodiment, the inhibitor of LPL may comprise one or more components of a CRISPR-Cas system. CRISPR methodologies employ a nuclease, CRISPR-associated (Cas), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas and guide RNA (gRNA) may be synthesized by known methods. Caslguide-RNA (gRNA) uses a non-specific DNA cleavage protein Cas, and an RNA oligo to hybridize to target and recruit the Cas/gRNA complex. In one embodiment, a guide RNA (gRNA) targeted to a gene encoding LPL, and a CRISPR-associated (Cas) peptide form a complex to induce mutations within the targeted gene. In one embodiment, the inhibitor comprises a gRNA or a nucleic acid molecule encoding a gRNA. In one embodiment, the inhibitor comprises a Cas peptide or a nucleic acid molecule encoding a Cas peptide.

The guide RNA sequence can be a sense or anti-sense sequence. In the CRISPR-Cas system derived from *S. pyogenes* (spCas9), the target DNA typically immediately precedes a 5'-NGG or NAG proto-spacer adjacent motif (PAM). Other Cas9 orthologs may have different PAM specificities. For example, Cas9 from *S. thermophilus* (stCas9) requires 5'-NNAGAA for CRISPR I and 5'-NGGNG for CRISPR3 and *Neiseria menigiditis* (nmCas9) requires 5'-NNNN-GATT. Cas9 from *Stapylococcus aureus* suhsp. *aureus* (saCas9) requires 5'-NNGRRT (R=A or G). The specific sequence of the guide RNA may vary, but, regardless of the sequence, useful guide RNA sequences will be those that minimize off-target effects while achieving high efficiency mutation of LPL.

In some embodiments, the composition comprises multiple different gRNA molecules, each targeted to a different target sequence. In some embodiments, this multiplexed strategy provides for increased efficacy. These multiplex gRNAs can be expressed separately in different vectors or expressed in one single vector.

The isolated nucleic acid molecules of the invention, including the RNA molecules (e.g., crRNA, tracrRNA, gRNA) or nucleic acids encoding the RNA molecules, may be produced by standard techniques. For example, polymerase chain reaction (PCR) techniques can be used to obtain an isolated nucleic acid containing a nucleotide sequence described herein, including nucleotide sequences encoding a polypeptide described herein. PCR can be used to amplify specific sequences from DNA as well as RNA, including sequences from total genomic DNA or total cellular RNA. Various PCR methods are described in, for example, *PCR Primer: A Laboratory Manual, 2$^{nd}$ edition*, Dieffenbach and Dveksler, eds., Cold Spring Harbor Laboratory Press, 2003. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

The isolated nucleic acids also can be chemically synthesized, either as a single nucleic acid molecule (e.g., using automated DNA synthesis in the 3' to 5' direction using phosphoramidite technology) or as a series of oligonucleotides. Isolated nucleic acids of the invention also can be obtained by mutagenesis of, e.g., a naturally occurring portion crRNA, tracrRNA, RNA-encoding DNA, or of a Cas9-encoding DNA In some embodiments, the isolated RNA molecules are synthesized from an expression vector encoding the RNA molecule, as described in detail elsewhere herein.

In one embodiment, the Cas9 protein comprises an amino acid sequence identical to the wild type *Streplococcus pyogenes* Cas9 amino acid sequence. In some embodiments, the Cas protein may comprise the amino acid sequence of a Cas protein from other species, for example other *Streptococcus* species, such as *thermophilus; Psuedomona aeruginosa, Escherichia coli*, or other sequenced bacteria genomes and archaea, or other prokaryotic microorganisms. Other Cas proteins, useful for the present invention, known or can be identified, using methods known in the art (see e.g., Esvelt et al., 2013, Nature Methods, 10: 1116-1121). In some embodiments, the Cas protein may comprise a modified amino acid sequence, as compared to its natural source. For example, in one embodiment, the wild type *Streptococcus pyrogenes* Cas9 sequence can be modified. For example, in some embodiments, the Cas9 protein comprises dCas9 having point mutations D10A and H840A, thereby rendering the protein as catalytically deficient. In some embodiments, the amino acid sequence can be codon optimized for efficient expression in human cells (i.e., "humanized) or in a species of interest.

The present invention also includes a vector in which the isolated nucleic acid of the present invention is inserted. The art is replete with suitable vectors that are useful in the present invention.

In brief summary, the expression of natural or synthetic nucleic acids encoding a protein inhibitor is typically achieved by operably linking a nucleic acid encoding the protein inhibitor or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the an. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method.

In some embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another, in the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter. MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of a protein inhibitor, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity, Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art in the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a peptide or protein into a host cell include calcium phosphate precipitation, lipofecrion, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York).

Biological methods for introducing a peptide or protein of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a peptide or protein into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular polypeptide, e.g., by immunological means (ELISAs and Western blots) or by assays described herein to identify agents falling within the scope of the invention.

Antibody Inhibitors

In some embodiments, the inhibitor is an antibody, or antibody fragment. In some embodiments, the inhibitor is an antibody, or antibody fragment, that specifically binds to LPL. That is, the antibody can inhibit LPL to provide a beneficial effect.

The antibodies may be intact monoclonal or polyclonal antibodies, and immunologically active fragments (e.g., a Fab or $(Fab)_2$ fragment), an antibody heavy chain, an antibody light chain, humanized antibodies, a genetically engineered single chain $F_V$ molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, humanized antibodies, fragments and chimeras, may be prepared using methods known to those skilled in the art.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1" "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VI region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand, binding site on the receptor, a ligand-receptor complex, and a marker. Bispecific antibodies can comprise a first antigen-binding site that specifically binds to a first target and a second antigen-binding site that specifically binds to a second target, with particularly advantageous properties such as producibility, stability, binding affinity, biological activity, specific targeting of certain T cells, targeting efficiency and reduced toxicity. In some instances, there are bispecific antibodies, wherein the bispecific antibody binds to the first target with high affinity and to the second target with low affinity. In other instances, there are bispecific antibodies, wherein the bispecific antibody binds to the first target with low affinity and to the second target with high affinity. In other instances, there are bispecific antibodies, wherein the bispecific antibody binds to the first target with a desired affinity and to the second target with a desired affinity.

Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

Delivery Vehicles

In one embodiment, the present invention provides a composition comprising delivery vehicle comprising an inhibitor of LPL. For example, in one embodiment, the delivery vehicle comprises a peptide inhibitor comprising at least one of SEQ ID NO: 1, SEQ ID NO: 2, SEQ ID NO: 3, SEQ ID NO: 4 or SEQ ID NO: 34.

Exemplary delivery vehicles include, but are not limited to, microspheres, microparticles, nanoparticles, polymerosomes, liposomes, and micelles. For example, in some embodiments, the delivery vehicle is loaded with peptide inhibitor, or a nucleic acid molecule encoding a peptide inhibitor. In some embodiments, the delivery vehicle provides for controlled release, delayed release, or continual release of its loaded cargo. In some embodiments, the delivery vehicle comprises a targeting moiety that targets the delivery vehicle to a treatment site.

In one embodiment, the composition comprises a nanoparticle comprising a loaded peptide inhibitor described herein. In certain embodiments, the nanoparticle is a lipid nanoparticle. In certain embodiments, the nanoparticle is a polymeric nanoparticle comprising one or more polymers, including, but not limited to, PLGA and PEG.

The delivery vehicle can be of various sizes. The appropriate size can vary based on the method of administration, the location to which the delivery vehicle is administered, the therapeutic agent employed and disease or disorder to be treated, as will be appreciated by a person of skill in the art in light of the teachings disclosed herein. For example, in some embodiments the delivery vehicle has a diameter of at least about 1 nm, or from about 1 nm to about 50 microns. The delivery vehicle can also have a diameter of, for example, from about 1 nm to about 30 microns; or from about 1 nm to about 10 microns; or from about 1 nm to about 6 microns; from about 1 nm to about 5 microns; or from about 1 nm to about 3 microns; or from about 1 nm to about 1000 nm; or from about 25 nm to about 750 nm; or from about 50 nm to about 500 nm; or from about 100 nm to about 300 nm. In some embodiments, the average delivery vehicle size can be about 1 nm, about 10 nm, about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, or about 1000 nm, or about 2.000 nm, or about 5,000 nm, or about 6,000 nm, or about 10,000 nm, or about 20,000 nm, or about 50,000 nm, or about 100,000 nm. In some embodiments, the delivery vehicle size can be about 100 microns or less, about 50 microns or less, about 30 microns or less, about 10 microns or less, about 6 microns or less, about 5 microns or less, about 3 microns or less, about 1000 nm or less, about 800 nm or less, about 600 nm or less, about 500 nm or less, about 400 nm or less, about 300 nm or less, about 200 nm or less, or about 100 nm or less. In some embodiments, the delivery vehicle con be a nanoparticle or a microparticle, as these terms are defined herein. In some embodiments, the drug delivery system can contain a plurality of delivery vehicles. The delivery vehicles can be all nanoparticles, all microparticles, or a combination of nanoparticles and microparticles.

The delivery vehicles of the drug delivery system can include a biocompatible polymer. As used herein, the term "biocompatible polymer" encompasses any polymer that can be administered to a patient without adverse effects to the patient, or for which any adverse effects are deemed by a person having ordinary skill in the art to be outweighed by the benefits brought about by the drug delivery system in light of the mode of administration, the therapeutic agent employed, and/or the eye disorder to be treated, and also when considered in light of the availability of alternative therapeutic regimen and their characteristics.

Examples of biocompatible polymers include but are not limited to polystyrenes; poly(hydroxy acid); poly(lactic acid); poly(glycolic acid); poly(lactic acid-co-glycolic acid); poly(lactic-co-glycolic acid); poly(lactide); poly(glycolide); poly(lactide-co-glycolide); polyanhydrides; polyorthoesters; polyamides; polycarbonates; polyalkylenes; polyethylenes; polypropylene; polyalkylene glycols; poly(ethylene glycol); polyalkylene oxides; poly(ethylene oxides); polyalkylene terephthalates; poly(ethylene terephthalate); polyvinyl alcohols; polyvinyl ethers; polyvinyl esters; polyvinyl halides; poly(vinyl chloride); polyvinylpyrrolidone polysiloxanes; poly(vinyl alcohols); poly(vinyl acetate); polyurethanes; co-polymers of polyurethanes; derivativized celluloses; alkyl cellulose; hydroxyalkyl celluloses; cellulose ethers; cellulose esters; ultra celluloses; methyl cellulose; ethyl cellulose; hydroxypropyl cellulose; hydroxy-propyl methyl cellulose; hydroxybutyl methyl cellulose; cellulose acetate: cellulose propionate; cellulose acetate butyrate; cellulose acetate phthalate; carboxylethyl cellulose; cellulose triacetate; cellulose sulfate sodium salt; polymers of acrylic acid; methacrylic acid; copolymers of methacrylic acid; derivatives of methacrylic acid; poly(methyl methacrylate); poly(ethyl methacrylate); poly(butylmethacrylate); poly(isobutyl methacrylate); poly(hexylmethacrylate); poly(isodecyl methacrylate); poly(lauryl methacrylate); poly(phenyl methacrylate); poly(methyl acrylate); poly(isopropyl acrylate); poly(isobutyl acrylate); poly(octadecyl acrylate); poly(butyric acid); poly(valeric acid); poly(lactide-co-caprolactone); copolymers of poly(lactide-co-caprolactone); blends of poly(lactide-co-caprolactone); hydroxyethyl methacrylate (HEMA); copolymers of HEMA with acrylate; copolymers of HEMA with polymethylmethacrylate (PMMA); polyvinylpyrrolidone/vinyl acetate copolymer (PVP/VA); acrylate polymers/copolymers; acrylate/carboxyl polymers; acrylate hydroxyl and/or carboxyl copolymers; polycarbonate-urethane polymers; silicone-urethane polymers; epoxy polymers; cellulose nitrates; polytetramethylene ether glycol urethane; polymethylmethacrylate-2-hydroxyethylmethacrylate copolymer; polyethylmethacrylate-2-hydroxyethylmethacrylate copolymer; polypropylmethacrylate-2-hydroxyethylmethacrylate copolymer polybutylmethacrylate-2-hydroxyethymethacrylate copolymer; polymethylacrylate-2-hydroxyethylmethacrylate copolymer, polyethylacrylate-2-hydroxyethylmethacrylate copolymer polypopylacrylate-2-hydroxymethacrylate copolymer; polybutylacrylate-2-hydroxyethylmethacrylatec copolymer copolymermethylvinylether maleicanhydride copolymer, poly (2-hydroxyethyl methacrylate) acrylate polymer/copolymer; acrylate carboxyl and/or hydroxyl copolymer; olefin acrylic acid copolymer, ethylene acrylic acid copolymer; polyamide polymersicopolymers; polyimide polymers/copolymers; ethylene vinylacetate copolymer; polycarbonate urethane; silicone urethane; polyvinylpyridine copolymers; polyether sulfones; polygalactin, poly-(isobutyl cyanoacrylate), and poly(2-hydroxyethyl-L-glutamine); polydimethyl siloxane; poly(caprolactones); poly(ortho esters); polyamines; polyethers; polyesters, polycarbamates; polyureas; polyimides; polysulfones; polyacetylenes; polyethyeneimines; polyisocyanates; polyacrylates; polymethacrylates; polyacrylonitriles; polyarylates; and combinations, copolymers and/or mixtures of two or more of any of the foregoing. In some cases, the delivery vehicle includes a hydrophobic material and at least one bioactive agent. In certain embodiments, the hydrophobic material is used instead of a polymer. In other embodiments, the hydrophobic material is used in addition to a polymer.

In some embodiments, the delivery vehicle comprises a biodegradable polymer. The biodegradable polymer can contain a synthetic polymer, although natural polymers also can be used. The polymer can be, for example, poly(lactic-co-glycolic acid) (PLGA), polystyrene or combinations thereof. The polystyrene can, for example, be modified with carboxyl groups. Other examples of biodegradable polymers include poly(hydroxy acid); poly(lactic acid); poly(glycolic acid); poly(lactic acid-co-glycolic acid); poly(lactide); poly (glycolide); poly(lactide-co-glycolide); polyanhydrides; polyorthoesters; polyamides; polycarbonates; polyalkylenes, polyethylene; polypropylene; polyalkylene glycols; poly(ethylene glycol); polyalkylene oxides; poly(ethylene oxides); polyalkylene terephthalates; poly(ethylene terephthalate); polyvinyl alcohols; polyvinyl ethers; polyvinyl esters; polyvinyl halides; poly(vinyl chloride); polyvinylpyrrolidone; polysiloxanes; poly(vinyl alcohols); poly (vinyl acetate); polyurethanes; co-polymers of polyurethanes; derivativized celluloses; alkyl cellulose; hydroxyalkyl celluloses; cellulose ethers; cellulose esters; nitro celluloses; methyl cellulose; ethyl cellulose; hydroxypropyl cellulose; hydroxy-propyl methyl cellulose; hydroxybutyl methyl cellulose; cellulose acetate; cellulose propionate; cellulose, acetate butyrate; cellulose acetate phthalate; carboxylethyl cellulose; cellulose triacetate; cellulose sulfate sodium salt; polymers of acrylic acid; methacrylic acid; copolymers of methacrylic acid; derivatives of methacrylic acid; poly(methyl methacrylate); poly(ethyl methacrylate); poly(butylmethacrylate); poly(isobutyl methacrylate); poly(hexylmethacrylate); poly(isodecyl methacrylate); poly(lauryl methacrylate); poly(phenyl methacrylate); poly(methyl acrylate); poly(isopropyl acrylate); poly (isobutyl acrylate); poly(octadecyl acrylate); poly(butyric acid); poly(valeric acid); poly(lactide-co-caprolactone); copolymers of poly(lactide-co-caprolactone); blends of poly (lactide-co-caprolactone); polygalactin; poly-(isobutyl cyanoacrylate); poly(2-hydroxyethyl-L-glutam-nine); and combinations, copolymers and/or mixtures of one or more of any of the foregoing. Furthermore, as a person of ordinary skill in the art would appreciate, some of the polymers listed above as "biocompatible" can also be considered biodegradable, whether or not they are included in the above listing of representative biodegradable polymers. As used herein, "derivatives" include polymers having substitutions, additions of chemical groups and other modifications routinely made by those skilled in the art.

In some embodiments, the delivery vehicle comprises a targeting moiety, for example on the outer shell or membrane, which directs the vehicle to a specific tissue, cell, or treatment site. For example, the vehicle may comprise a targeting moiety that directs the vehicle of the present invention to bone, an osteoclast, or to sites of bone resorption.

Substrates

In one embodiment, the present invention provides a scaffold, substrate, or device comprising an LPL inhibitor as described herein. For example, in one embodiment, the scaffold, substrate, or device comprises a peptide inhibitor comprising at least one of SEQ ID NO: 1, SEQ ID NO: 2, SEQ ID NO: 3, SEQ ID NO: 4 or SEQ ID NO: 34.

For example, in some embodiments, the present invention provides a tissue engineering scaffold, including but not limited to, a hydrogel, electrospun scaffold, polymeric matrix, or the like, comprising the inhibitor. In certain embodiments, the inhibitor may be coated along the surface of the scaffold, substrate, or device. In certain embodiments, the inhibitor is encapsulated within the scaffold, substrate, or device.

Pharmaceutical Compositions

The present invention also provides pharmaceutical compositions comprising one or more of the compositions described herein. Formulations may be employed in admixtures with conventional excipients, i.e., pharmaceutically acceptable organic or inorganic carrier substances suitable for administration to a treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

Administration of the compositions of this invention may be carried out, for example, by parenteral, by intravenous, subcutaneous, intramuscular, or intraperitoneal injection, or by infusion or by any other acceptable systemic method.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group: benzyl alcohol, sorbic acid, parabens, imidurea and combinations thereof.

In one embodiment, the composition includes an antioxidant and a chelating agent that inhibits the degradation of one or more components of the composition. Exemplary antioxidants for some compounds are BHT, BHA, alpha-tocopherol and ascorbic acid. Exemplary chelating agents include edetate salts (e.g. disodium edetate) and citric acid. The chelating agent is useful for chelating metal ions in the composition that may be detrimental to the shelf life of the formulation. While BHT and disodium edetate may be the antioxidant and chelating agent respectively for some compounds, other suitable and equivalent antioxidants and chelating agents may be substituted therefore as would be known to those skilled in the ar.

Liquid suspensions may be prepared using conventional methods to achieve suspension of the compounds or other compositions of the invention in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are nor limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl pare hydroxybenzoates, ascorbic acid, and sorbic acid.

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, chewing gum, varnishes, sealants, oral and teeth "dissolving strips", or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type. OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Methods of Inhibiting LPL

In one aspect, the present invention provides a method of inhibiting LPL expression, activity or both. For example, in certain embodiments, the method reduces, inhibits, or prevents LPL phosphorylation, for example on Ser 5, Ser 7, or Ser 5 and Ser 7 of LPL.

In one embodiment, the method of inhibiting LPL comprises administering to a subject or biological system (e.g., a cell, a population of cells, a tissue, an organ, or another system) a composition comprising an inhibitor of LPL, as described elsewhere herein. For example, in one embodiment, the method comprises administering to a subject or biological system a composition comprising a peptide inhibitor, or a nucleic acid molecule encoding a peptide inhibitor, wherein the peptide inhibitor comprises an N-terminal fragment, or variant thereof, of LPL which acts as a competitive inhibitor of LPL. In one embodiment, the method comprises administering to a subject or biological system a composition comprising a peptide inhibitor, or a nucleic acid molecule encoding a peptide inhibitor, wherein the peptide inhibitor comprises at least one of SEQ ID NO: 1, SEQ ID NO: 2, SEQ ID NO: 3, SEQ ID NO: 4 or SEQ ID NO: 34. In one embodiment, the method comprises administering to a subject or biological system a composition comprising a fusion peptide, or a nucleic acid molecule encoding a fusion peptide inhibitor, wherein the fusion peptide comprises a transduction domain and an inhibitor domain. In some embodiments, the inhibitor domain of the fusion peptide comprises an N-terminal fragment, or variant thereof, of LPL which acts as a competitive inhibitor of LPL, in some embodiments, the inhibitor domain of the fusion peptide comprises at least one of SEQ ID NO: 1, SEQ ID NO: 2, SEQ ID NO: 3, SEQ ID NO: 4 or SEQ ID NO: 34.

In some embodiments, the method of inhibiting LPL is used to reduce, inhibit, or prevent bone resorption or bone resorption activity of osteoclasts. In some embodiments, the method of inhibiting LPL is used to treat or prevent a disease or disorder associated with bone resorption, including but not limited to osteoporosis and periodontal disease.

Treatment Methods

The present invention provides a method for the treatment or prevention of a disease or disorder associated with bone resorption in a subject in need thereof. The present method may be used to treat or prevent any disease or disorder characterized by aberrant or excessive bone loss or bone resorption.

Examples of diseases and disorders that may be treated or prevented by way of the present method include, but are not limited to, osteoporosis, idiopathic primary osteoporosis, age-related osteoporosis, glucocorticoid-induced osteoporosis, Hajdu-Cheney syndrome, osteolysis, post-transplant bone disease, Pager's disease of bone, bone loss associated with cancer, periodontal disease, and periodontitis.

In some embodiments, compositions of the present invention are co-administered with other therapeutics or prophylactics relevant to the diseases including, but not limited to, bisphosphonates, estrogen, selective estrogen receptor modulators (SERMs), parathyroid hormone, calcitonin, calcium, vitamin D, hormone therapy, hormone-like compounds, RANKL inhibitors, denosumab, teriparatide, raloxifene, and abaloparatide. An exemplary hormone-like medication for treating and preventing osteoporosis, includes, but is not limited to raloxifene (Evista). An exemplary RANKL inhibitor is Denosumab (Prolia, Xgeva), which can reduce the risk of osteoporotic fracture, and can be used in those unable to take a bisphosphonate such as those with reduced kidney function. Another exemplary therapeutic is teriparatide (Forteo), a recombinant protein form of parathyroid hormone, typically reserved for men and postmenopausal women who have very low bone density, who have had fractures or whose osteoporosis is caused by steroid medication. Another exemplary therapeutic is abaloparatide (Tymlos), a parathyroid hormone-related protein analog drug that, like teriparatide, has the potential to rebuild bone.

In some embodiments, the composition of the invention is administered before, during, or after another treatment of the disease or disorder.

In one aspect, the invention provides a method for preventing in a subject, a disease or disorder, by administering to the subject a composition described herein. Subjects at risk for a disease or disorder identified by, for example, any diagnostic or prognostic assay. Administration of a prophylactic agent can occur prior to the manifestation of symptoms characteristic of the disease or disorder, such that the disease or disorder is prevented or delayed in its progression.

Another aspect of the invention pertains to methods of modulating expression, activity, or phosphorylation of LPL for therapeutic purposes. The modulatory method of the invention involves contacting a cell or subject with a composition described herein that modulates the expression, activity, or phosphorylation of LPL.

In some embodiments, the method comprises administering an effective amount of a composition described herein to a subject diagnosed with, suspected of having, or at risk for developing disease or disorder associated with bone resorption. In some aspects, the composition is contacted to a cell or tissue where a condition is present or at risk of developing. In one embodiment, the composition is administered systemically to the subject.

The composition of the invention may be administered to a patient or subject in need in a wide variety of ways. Modes of administration include intraoperatively intravenous, intravascular, intramuscular, subcutaneous, intracerebral, intraperitoneal, soft tissue injection, surgical placement, arthroscopic placement, and percutaneous insertion, e.g., direct injection, cannulation or catheterization. Any administration may be a single application of a composition of invention or multiple applications. Administrations may be to single site or to more than one site in the individual to be treated. Multiple administrations may occur essentially at the same time or separated in time.

Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "therapeutic amount" is indicated, the precise amount of the compositions of the present invention to be administered can be determined by a physician with consideration of individual differences in age, weight, disease type, extent of disease, and condition of the patient (subject).

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are administered by i.v. injection.

The pharmaceutical compositions useful for practicing the invention may be administered to deliver a dose of from 1 ng/kg/day and 100 mg/kg/day. In one embodiment, the invention envisions administration of a dose which results in a concentration of the compound of the present invention from 1 µM and 10 µM in a mammal.

Typically, dosages which may be administered in a method of the invention to a mammal range in amount from 0.5 µg to about 50 mg per kilogram of body weight of the mammal, while the precise dosage administered will vary depending upon any number of factors, including but not limited to, the type of mammal and type of disease state being treated, the age of the mammal and the route of administration. In one embodiment, the dosage will vary from about 1 µg to about 50 mg per kilogram of body weight of the mammal, in one embodiment, the dosage will vary from about 1 mg to about 10 mg per kilogram of body weight of the mammal.

The compound may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

The administration of a nucleic acid or peptide inhibitor of the invention to the subject may be accomplished using gene therapy. Gene therapy, which is based on inserting a therapeutic gene into a cell by means of an ex vivo or an in vivo technique. Suitable vectors and methods have been described for genetic therapy in vitro or in vivo, and are known as expert on the matter; see, for example, Giordano, Nature Medicine 2 (1996), 534-539; Schaper, Circ. Res 79 (1996), 911-919; Anderson, Science 256 (1992), 808-813; Isner, Lancet 348 (1996), 370-374; Muhlhauser, Circ. Res 77 (1995), 1077-1086; Wang, Nature Medicine 2 (1996), 714-716; WO9429469 WO97/00957 or Schaper, Current Opinion in Biotechnology 7 (1996), 635-640 and the references quoted therein. The polynucleotide codifying the polypeptide of the invention can be designed for direct insertion or by insertion through liposomes or viral vectors (for example, adenoviral or retroviral vectors) in the cell. In one embodiment, the cell is a cell of the germinal line, an embryonic cell or egg cell or derived from the same. In some instances, the cell is a core cell. Suitable gene distribution systems that can be used according to the invention may include liposomes, distribution systems mediated by receptor, naked DNA and viral vectors such as the herpes virus, the retrovirus, the adenovirus and adeno-associated viruses, among others. The distribution of nucleic acids to a specific site in the body for genetic therapy can also be achieved by using a biolistic distribution system, such as that described by Williams (Proc. Natl. Acad. Sci. USA, 88 (1991), 2726-2729). The standard methods for transfecting cells with recombining DNA are well known by an expert on the subject of molecular biology, see, for example, WO94/29469; see also supra. Genetic therapy can be carried out by directly administering the recombining DNA molecule or the vector of the invention to a patient or transfecting the cells with the polynucleotide or the vector of the invention ex vivo and administering the transfected cells to the patient.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: L-Plastin Phosphorylation Regulates the Early Phase of Sealing Ring Formation by Actin Bundling Process in Mouse Osteoclasts The process of sealing ring formation requires major actin filament reorganization. It was previously demonstrated that an actin-bundling protein L-plastin has a role in the cross-linking of actin filaments into tight bundles and forms actin aggregates (denoted as nascent sealing zones). These nascent sealing zones mature into fully functional sealing rings, t is described herein that TNF-alpha signaling regulates the phosphorylation of serine-5 and -7 in L-plastin which increases the actin bundling capacity of L-plastin and hence the formation of nascent sealing zones in mouse osteoclasts. Using the TAT-mediated transduction method, the role of L-Plastin was confirmed in nascent sealing zones formation at the early phase of sealing ring assembly. Transduction of TAT-fused full-length L-plastin peptide significantly increases the number of nascent sealing zones and therefore sealing rings. But, transduction of amino-terminal L-plastin peptides comprising the serine-5 and -7 reduces the formation of both nascent sealing zones and sealing rings. Therefore, bone resorption in vitro was reduced considerably. The decrease was associated with the selective inhibition of cellular L-plastin phosphorylation by the transduced peptides. Neither the formation of podosomes nor the migration was affected in these osteoclasts. Further, it is described herein that phosphorylation of L-plastin on serine 5 and -7 residues increases F-actin bundling capacity. These studies provide a better understanding of L-plastin as a potential regulator at the early phase of scaling ring formation and further provides a new therapeutic target to treat bone loss.

The materials and methods employed in these experiments are now described.

Mice

C57/BL6 mice (six to eight-week-old mice) were used for osteoclast preparation. Antibody to LPL (SC-16657; Goat) was bought from Santa Cruz Biotechnology, Inc. (Santa Cruz, Calif.). Antibodies to GAPDH and TNF-α receptor 1 (TNFR1) were purchased from R & D Systems (Minneapolis, Minn.). Protein estimation reagent, molecular weight standards for proteins, and PAGE reagents were bought from Bio-Rad (Hercules, Calif.). Cy2- and Cy3-conjugated secondary antibodies were purchased from Jackson Immunoresearch (West Grove, Pa.). HRP-conjugated secondary antibodies for immunoblotting and phosphoserine (p-Serine) antibody were bought from Abcam (Cambridge, Mass.). Mounting solutions for mounting of coverslips were bought from Thomas Scientific (Swedesboro, N.J.) or Vector Labs (Burlingame, Calif.). Rhodamine-phalloidin and all other chemicals were purchased from Sigma (St. Louis, Mo.).

Preparation of Osteoclasts from Long Bones

Osteoclasts were generated in vitro using long bone marrow cells of six to eight weeks-old C57B16 mice as described previously (Chellaiah et alt, 2000, J. Cell Biol., 148: 665-678; Chellaiah et al., 2000, J. Biol. Chem., 275:

11993-12002). The multinucleated osteoclasts were seen from day four onward. The heterogeneous culture consists of a large number of (>85%) multinucleated giant osteoclasts and some osteoclast precursors (~10 to 15%).

Treatment of Osteoclasts with Bone Particles and TNFR-1 Antibody

Bone particles (60-80 µm in size) were prepared as described previously (Ma et at, 2010, J. Biol. Chem., 285: 29911-29924). After flushing the marrow cells for osteoclast differentiation as described above, long bones of mice (free of cells inside and muscles outside) were washed extensively with PBS and kept in ethanol until use. Long bones were air-dried in the hood and homogenized by a mini blender. Bone particles were sieved and used for experiments. Multinucleated osteoclasts were seen from day four onward. At this time cultures were added with bone particles (100 µg/ml media) for 3-4 hours or 12-14 hours in the presence of TNF-α (20 ng/ml). Some cultures were treated with 3-5 µg/ml TNFR1 antibody. Osteoclasts were preincubated with the TNFR1 antibody for 60-90 minutes before the addition of TNF-α to enhance the blocking effect. Osteoclasts incubated with bone particles for 3-4 or 12-14 hours in the presence of TNF-α were used for lysate preparations.

Cloning of L-Plastin Constructs

Bacterial expression constructs coding various HIV-TAT fusion peptides of LPL were generated by PCR method as described (Ma et al., 2008, J. Mol. Signal, 3: 4). LPL constructs were generated from mouse cDNA library using the following primers:

```
Full length (FL-) LPL:
(F)
                                       (SEQ ID NO: 24)
5'-ACA TGA CCG GTA TGG CCA GAG GAT CCG TG-3'
and (R)
                                       (SEQ ID NO: 25)
5'-CAC ATG AAT TCA CTT ACA CCC TCT TCA TCC CTT

TC-3';

Amino terminal (NT)-LPL:
(F)
                                       (SEQ ID NO: 26)
5'-ACA TGA CCG GTA TGG CCA GAG GAT CCG TG-3'
and (R)
                                       (SEQ ID NO: 27)
5'-CAC ATG AAT TCA CTT AGT ACC CAG GCA GAGGCA GGC

AG-3';

Actin binding domain (ABD) of LPL:
(F)
                                       (SEQ ID NO: 28)
5'-ACA TGA CCG GTA CCT CTG AGC AGT CCA GCG TTG-3'
and (R)
                                       (SEQ ID NO: 29)
5'-CAC ATG AAT TCA CTT ACT TCT GTC CAC CTC CGA

TAT C-3'.
```

The PCR products of LPL were inserted into the AgeI/EcoRI site of a bacterial expression vector, pTAT-HA, to produce TAT fusion proteins. The sequences of all the clones were confirmed for reading frame by DNA sequencing.

Site-Directed Mutagenesis of L-Plastin

Mutations at Ser5 and Ser7 were generated using the Quick Change Site-Directed Mutagenesis (SDM) Kit (Agilent Technologies. Halethorpe) and as per the instructions provided in the manufacturer's protocol. Full-length L-plastin (FL-LPL) cDNA (GenBank Accession: BC010271) have been used to generate the Ser-5 and Ser-7 to Ala-5 and Ala-7 mutant. The following forward and reverse primers with SalI and SphI sites, respectively are used to generate the mutants: F5'-ACGCGTCGACATGGCCAGAGGAGCAGTGGCC-GATGAGGAAATGATG-3'(SEQ ID NO: 30); R5'-TGCTG CAGCATGCATTCTGCCCTC 3' (SEQ ID NO: 31). First, the SalI-SphI fragment of the mutated cDNA was generated in pCMV-SPORT6. Several positive clones have been identified and sequenced to verify the insertion of expected mutations and also for the insertion of any other unsought mutations during the mutagenesis process. Subsequently, mutated FL-LPL was cloned into the pTAT-HA vector at KpnI-EcoRI sites to produce mutated TAT-fused mutated FL-LPL protein. The forward and reverse primers containing KpnI-EcoRI sites, respectively are as follows: F-'5' CGGGGTACCATGGCCAGAGAGGACAGTGGCC-3' (SEQ ID NO: 32); R-5' GGAATGAAGAG GGTGT-GAGAATT CCGG-3' (SEQ ID NO: 33).

Purification of TAT-Fused LPL Proteins, and Transduction of TAT-Fused LPL Proteins into Osteoclasts The vector pTAT-HA has an N-terminal 6-histidine leader (Nagahara et al., 1998, Nature Medicine, 4:1449-1452). Hence, TAT-fused LPL peptides were purified using Ni-NTA column essentially as described previously (Chellaiah et al., 2000, J. Biol. Chem., 275: 11993-12002; Vocero-Akbani et al., 2001, Meth. Enzymol., 332: 36-49). For transduction with TAT-fused peptides (100-150 nM), osteoclasts were first kept in serum-free α-MEM for two hours. Afterward, TAT proteins of interest, bone particles, and TNF-α were added to cells in serum-free α-MEM Lysates were made from these cells for immunoprecipitation and immunoblotting analyses. Osteoclasts plated on dentine slices in the presence of TAT-proteins of interest and TNF-α for 3-6 hours or 12-14 hours were used for immunostaining or actin staining analyses. Osteoclast cultures treated only with TNF-α were used as controls.

Lysate Preparation, Immunoprecipitation and Immunoblotting Analysis

Following various treatments, osteoclasts were washed three-times with cold PBS and lysed in a radioimmune precipitation buffer (RIPA; 10 mM Tris-HCl, pH 7.2, 150 mM NaCl, 1% deoxycholate, 1% Triton X-100, 0.1% SDS, 1% aprotinin, 2 mM PMSF, 100 M $Na_3VO_4$, and 1% aprotinin). Cells were rocked on ice for 15 minutes and scraped off with a cell scraper. Cell lysates were centrifuged at 15,000 rpm for 5 minutes at 4° C., and the supernatant was saved. Protein contents were measured using Bio-Rad protein assay reagent. Equal amounts of lysate proteins (100-150 µg) were used for immunoprecipitations. Immunoprecipitations and Western blotting were done as described previously (Chellaiah et al., 1998, J. Biol. Chem., 273: 11908-11916; Chellaiah et al., 1996, Mol. Biol. Cell, 7: 743-753).

Fluorescent Labeling of Proteins in Osteoclasts

Osteoclast precursors ($10^5$ cells/coverslips) were cultured on glass cover slips or dentine slices. Fluorescent labeling was done in osteoclasts transduced or untransduced with TAT-proteins. HA or TAT antibody was used to identify the transduced peptides of interest; rhodamine phalloidin was used to determine actin organization (Chellaiah et al., 2000, J. Cell Biol., 148: 665-678; Chellaiah et al., 2000, J. Biol. Chem., 275: 11993-12002). Immunostained and actin stained osteoclasts were photographed with a Bio-Rad confocal laser-scanning microscope. Images were stored in TIF image format and processed by Adobe Photoshop (Adobe Systems Inc., Mountain View. Calif.).

Measurement of Filamentous Actin (F-Actin) Content with Rhodamine Phalloidin

For the measurement of F-actin, osteoclasts transduced with TAT-LPL peptides of interest for 15 to 30 minutes were re-plated on dentine slices for 3 to 4 hours or 10-12 hours, respectively, in the presence of indicated TAT-fused peptides of interest and TNF-α. For each treatment four to six wells in 24 well, culture dishes were used. Cells were fixed and rhodamine phalloidin binding to F-actin was done as described (Chellaiah et al., 2000, J. Cell Biol., 148: 665-678; Chellaiah et al., 2000, J. Biol. Chem., 275: 11993-12002: Chellaiah et at, 2007, J. Biol. Chem., 282: 10104-10116), Resorption Pit Formation Assay In Vitro Using Dentine Slices Osteoclasts transduced with TAT-LPL peptides of interest for 30 minutes, were re-plated on dentine slices for 10-12 hours in the presence of TAT-fused peptides of interest and TNF-α. Some cultures were treated with a neutralizing antibody to TNFR-1. Resorption assay was performed as described previously (Chellaiah et al., 2000, J. Cell Biol., 148: 665-678; Chellaiah at al., 2000, J. Biol. Chem., 275: 11993-12002). Resorbed area were also scanned in confocal microscopy. Images were stored in TIF format and processed by Adobe Photoshop (Adobe Systems Inc.) (Chellaiah et al., 2000, J. Cell Biol, 148: 665-678). The resorbed pit areas were quantified and data were compiled from four slices per treatment and per experiment. The resorbed pit areas (20-25 pits/slice) were quantified and data were compiled from four slices per treatment. The data showed (G) are the mean±SD of one experiment performed. The area of the pit was determined from the free-hand traced perimeter using the LSM software (Chellaiah et al., 2000, J. Cell Biol., 148: 665-678). As per Cosmo Bio recommendations, the results of one experiment was compiled for the presentation.

Transwell Migration Assay

Transwell migration was done essentially as reported previously (Chellaiah et al., 2000, J. Cell Biol., 148: 665-678). Osteoclasts that migrated to the underside of the transwell membrane were stained with hematoxylin stain. Dried filters ware cut out and mounted with a permount solution (Thomas Scientific, Swedesboro, N.J.) on a glass slide. Cells were viewed under X40 objective in an inverted microscope. Six fields per transwell insert were counted using a Zeiss microscope as described previously (Chellaiah et al., 2000, J. Biol. Chem., 275: 11993-12002). Data are presented as the number of cells per migrated field (mean±SD) from one experiment.

Statistical Analysis

Data obtained represent the response of the osteoclast culture as a whole (>85% multinucleated giant cells and -10-5% osteoclast precursors). Statistical significance was determined using either analysis of variance ANOVA or student's t-Test (INSTAT; Version 6.0, Graph Pad software. GraphPad Inc, San Diego, Calif.). Results are presented as means±SD. A probability value<0.05 was considered to be statistically significant and <0.01 was considered to be highly significant.

The results of experiments are now described.

Expression and Purification of the TAT-Fused LPL Peptides

Purified proteins were subjected to SDS-PAGE followed by Western analysis with a hemagglutinin (HA) antibody and Coomassie blue staining to determine the molecular weight and homogeneity. The following HA-TAT fused LPL proteins were generated; unmutated and mutated full-length (FL)-LPL (70-75 kDa), amino terminal (NT)-LPL-15 kDa), and actin binding domains (ABD; 50-55 kDa) of LPL (FIG. 1A). Purified proteins were analyzed in an 8% (FL-LPL; ABD-LPL) or 15% (NT-LPL and TAT-HA vector protein) SDS-PAGE. Gels were stained with Coomassie blue stain (FIG. 1B). TAT-HA vector (8-10 kDa) and Herplex Simplex Virus thymidine kinase (HSV-TK; 42 kDa) proteins were used as controls for transduction experiments. Dose- and time-dependent uptake of proteins by osteoclasts were done as shown previously (Hanein et al., 1998, Nat. Struct. Biol., 5: 787-792). Maximum uptake was seen between the 100-200 nM dose of TAT-fused PL-LPL (FIG. 1C; lanes 3-5). The uptake of TAT-fused FL-LPL reaches maximal levels at 45 minutes to 2 hours (FIG. 1D; lanes 4 and 5) and the protein appeared to be stable for up to 6-8 hours (lane 6) and reduced from 12 hours onwards (lanes 7-9). Therefore, osteoclasts were incubated with 150 nM TAT-fused peptides (control and LPL peptides) for 3-4 hours. Loading was normalized to the cellular levels of GAPDH for blots shown in FIG. 1C and FIG. 1D. Based on these experiments, 100-150 nM concentration of TAT proteins have been used for experiments shown below.

Analysis of the Effect of Transduction of TAT-Fused LPL Peptides on the Phosphorylation of Endogenous LPL and Actin Modulations Previous studies have shown that the actin bundling process is dependent on the phosphorylation of LPL (Al et al., 2010, PLoS ONE, 5, e9210; Delanote et al., 2005, Acta Pharmacol. Sin., 26: 769-779; Ma et al., 2010, J. Biol. Chem., 285; 29911-29924; Morley, 2012, Int. J. Cell Biol., 2012: 935173; Wang et al., 2010, J Immunol., 185: 7487-7497). Here, experiments were conducted to elucidate the significance of LPL phosphorylation on actin dynamics associated with the NSZs formation in osteoclasts transduced with TAT-fused LPL peptides (FIG. 1). First, experiments were conducted to examine the phosphorylation of endogenous LPL in the presence of bone particles and TNF-α. Osteoclasts untransduced (FIG. 2A; lane 1) or transduced with peptides such as unmutated (lanes 2 and 5) and mutated FL-LPL (lane 6), ABD (lane 4) and non-specific control peptide HSV-TK (lane 7) demonstrated basal level phosphorylation of endogenous LPL (~68-70 kDa). Phosphorylation of the transduced TAT-fused FL-LPL was also seen at a molecular mass of ~80 kDa in FL-LPL transduced osteoclasts (FIG. 2A; lanes 2 and 5) and not in mutated FL-LPL transduced osteoclasts (lane 6). Most importantly, transduction of NT-LPL exerted a significant inhibitory effect on the phosphorylation of endogenous LPL (lane 3). Inhibition was found to be >72±7.3% (mean±SD of three blots) with NT-LPL peptide. Immunoblotting with an LPL antibody demonstrates both endogenous LPL protein (FIG. 28, Lanes 1-7) and transduced FL-LPL peptide (mutated and unmutated; lanes 2, 5, and 6).

Figure 20:
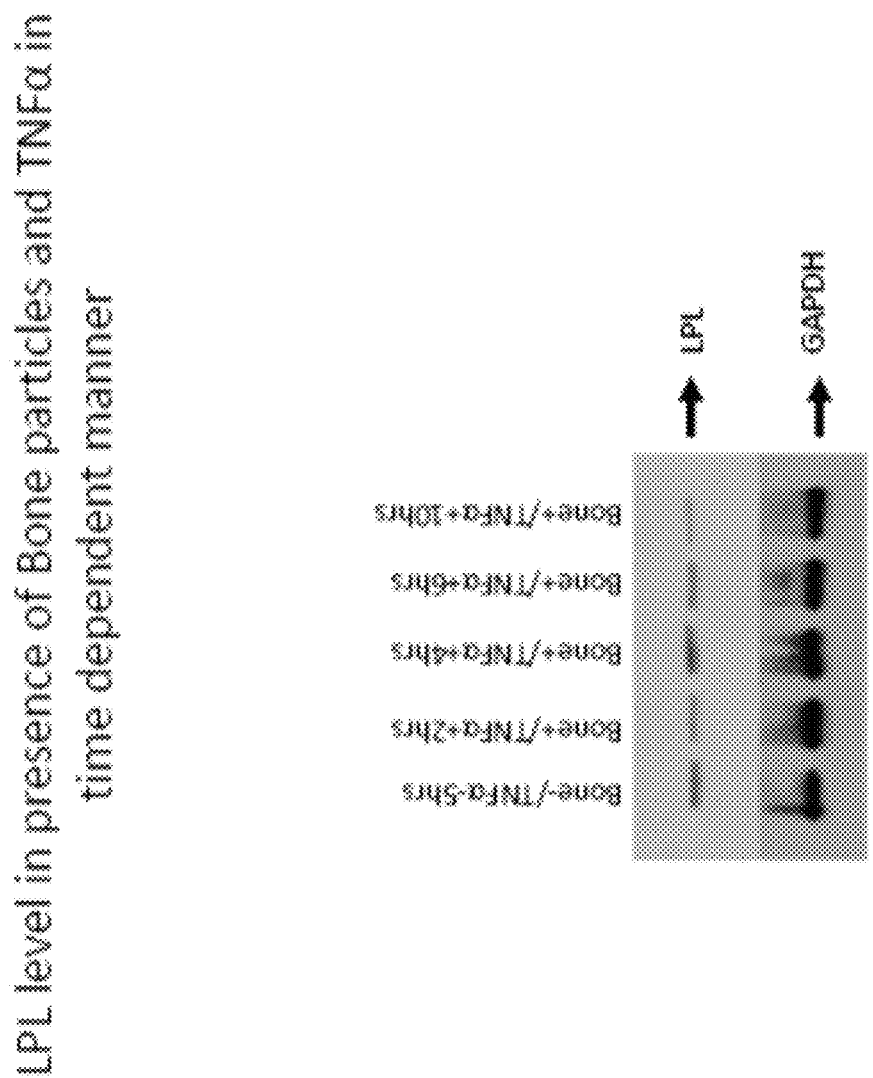
FIG. 20 depicts the results of example experiments depicting time-dependent changes in LPL level in the presence of TNF-α and bone particles in osteoclasts derived from RAW cells. As shown previously (Ma et al., 2010, J Biol Chem., 285: 2991-29924) in mouse osteoclasts, a time-dependent change in LPL level was observed in the presence of TNF-α and bone particles. An increase was observed at 4 hours and decreased gradually from 6 to 10 hours. Lane 1 is the LPL level in the absence of bone.

Next, experiments were conducted to determine whether the decrease in the phosphorylation of cellular LPL (FIG. 2A, lane 3) is due to competitive inhibition mediated by the transduced NT-LPL peptide. Immunoblotting with a p-Serine antibody (FIG. 2D; lanes 1 and 2) demonstrated the phosphorylation of transduced NT-LPL peptide (FIG. 2D; lane 2). Stripping and reprobing of this blot with an antibody to HA demonstrate the immunoprecipitated levels of the transduced NT-LPL level (FIG. 2D, lane 4). Neither NT-LPL nor phospho-NT-LPL was observed in the immunoprecipitates made with non-immune serum (NI; FIG. 20; lanes 1 and 3). GAPDH immunoblot was used to normalize the amount of lysate protein used (input) for indicated immunoprecipitations (FIG. 2C and FIG. 2D). Results with mutated FL-LPL (A5A7) and NT-LPL suggest that TNF-α signaling regulates the phosphorylation of LPL protein. Also, NT-LPL peptide can inhibit the phosphorylation of endogenous (cellular) LPL competitively.

Figure 3:
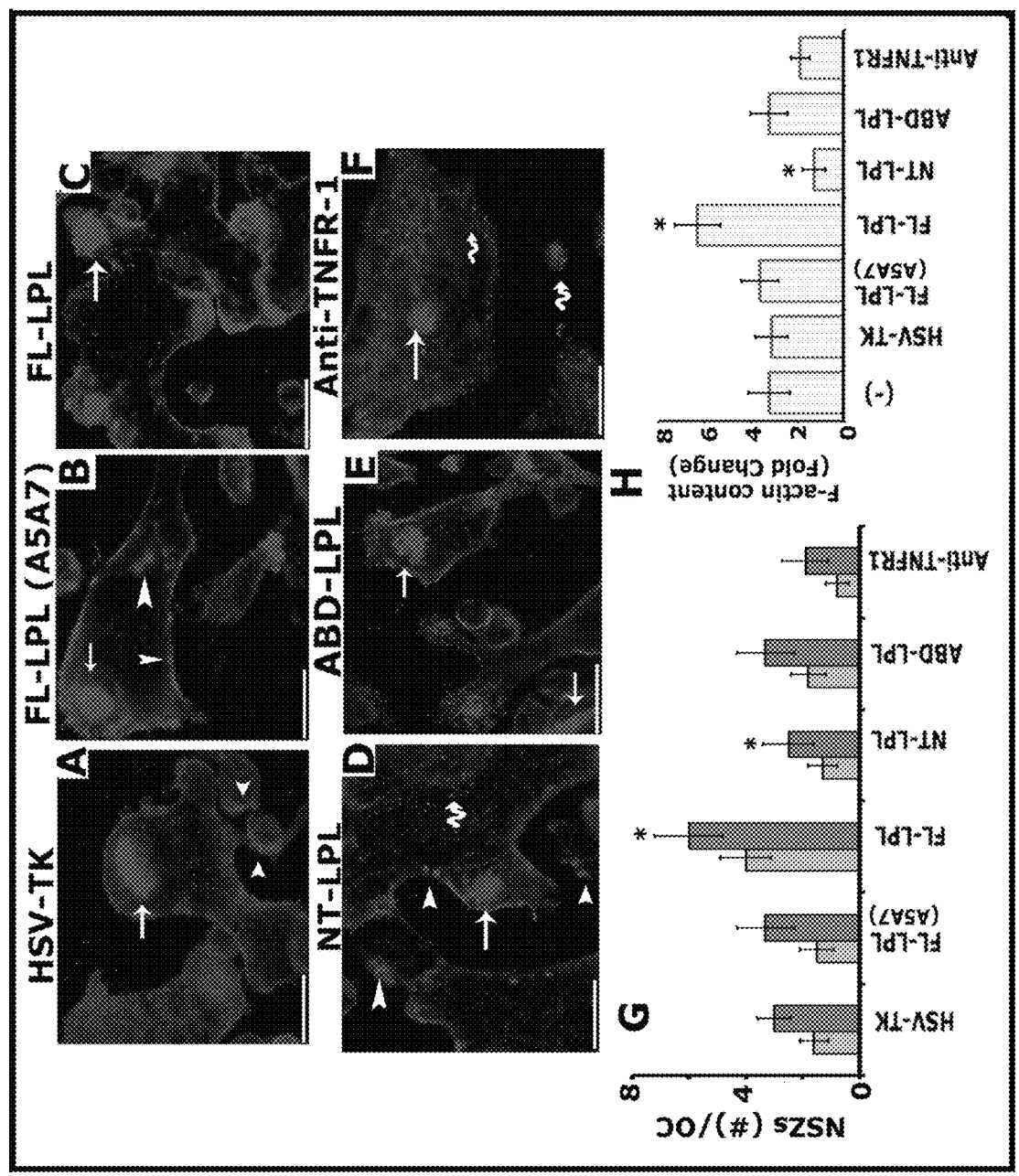
FIG. 3, comprising

Analysis of the Effect of Transduction of TAT-Fused LPL Peptides on NSZs Formation in Osteoclasts Plated on Dentine Consequently, it was of interest to study whether the transduced peptides would modulate actin dynamics in osteoclasts and whether this modulation was associated with the phosphorylation of transduced peptides. Therefore, osteoclasts transduced with various domains of LPL were plated on dentine slices for 2-3 hours in the presence of TNF-α and actin staining was done (FIG. 3A-FIG. 3F). The number of small and big NSZs were counted in 100-120 osteoclasts and provided as a graph (FIG. 3G). The effects of various TAT-fused LPL peptides on the total F-actin content of osteoclasts was also examined (FIG. 3H). Actin staining showed that big NSZs were found at the extensions of the plasma membrane. The number of NSZs and F-actin content are more or less equal in osteoclasts transduced with peptides such as HSV-TK, mutated FL-LPL (A5A7), and ABD-LPL (FIG. 3A, FIG. 3B, and FIG. 3E). ABD alone had no effect on the actin bundling process and NSZs formation. The level observed in these osteoclasts are considered the basal level and no additional actin bundling process took place. However, a substantial increase above the basal level was found in the number of NSZs and F-actin content in osteoclasts transduced with FL-LPL (FIG. 3C, FIG. 3G and FIG. 3H). A significant decrease below the basal level was observed in osteoclasts transduced with NT-LPL (FIG. 3D) or treated with a neutralizing antibody to TNF receptor 1 (TNFR-1; FIG. 3F). The number of big and small NSZs and F-actin content are significantly reduced in these osteoclasts (FIG. 3G and FIG. 3H). Actin enriched aggregates are seen in larger and smaller sizes. They are certainly bigger than typical podosomes (FIG. 3F; indicated by wavy arrows) and are growing NSZs. Arrowheads in FIG. 3A, FIG. 3B, and FIG. 3D denote where small aggregates have been found. It is also interesting to observe that formation of podosome-like structures (indicated by wavy arrows) which are not affected by NT-LPL peptide or neutralizing antibody to TNFR-1. However, impaired endogenous LPL phosphorylation changed not only the formation of larger NSZs but also membrane extensions which assist in the spreading of osteoclasts.

Figure 2:
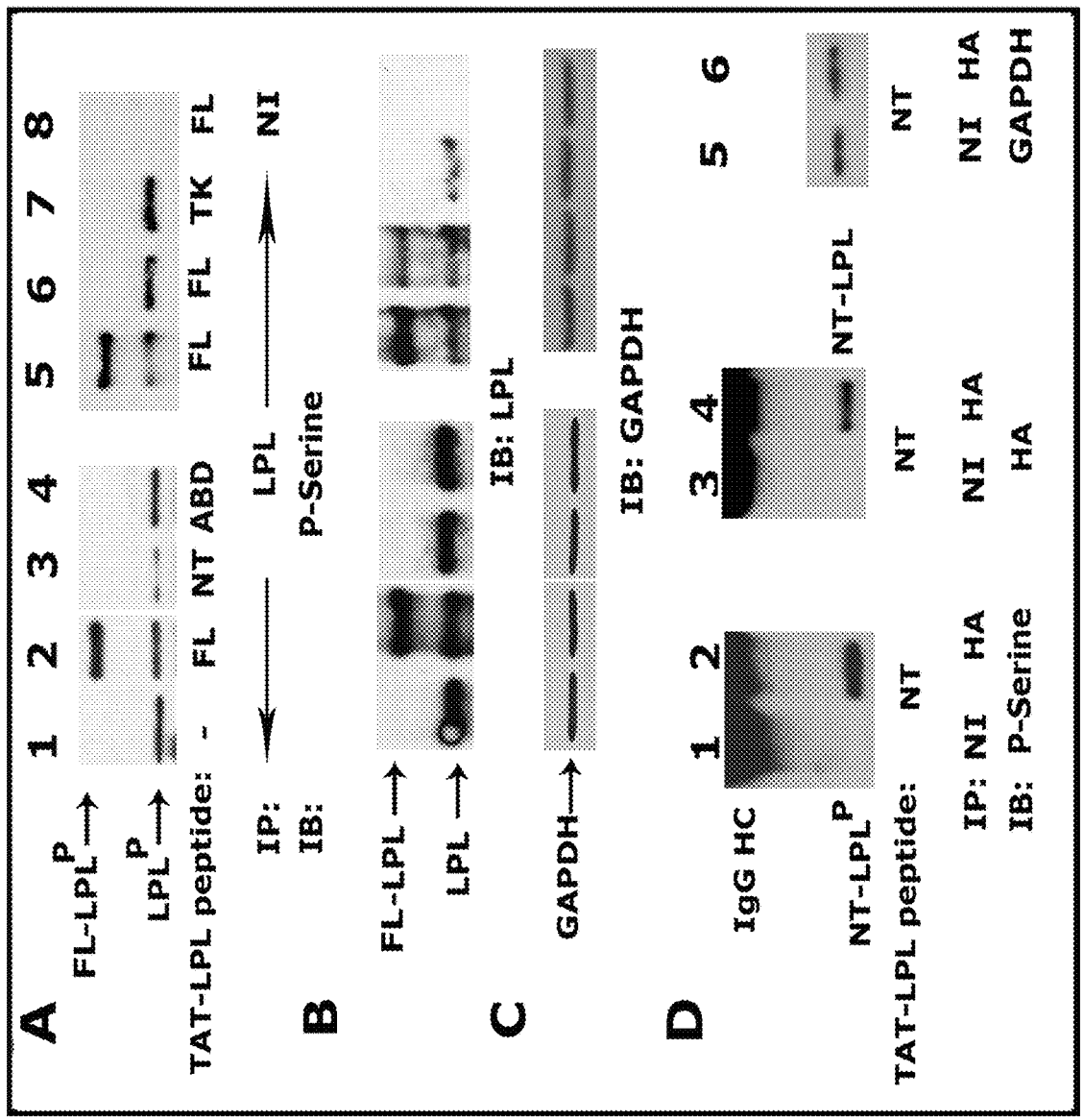
FIG. 2, comprising
Figure 7:
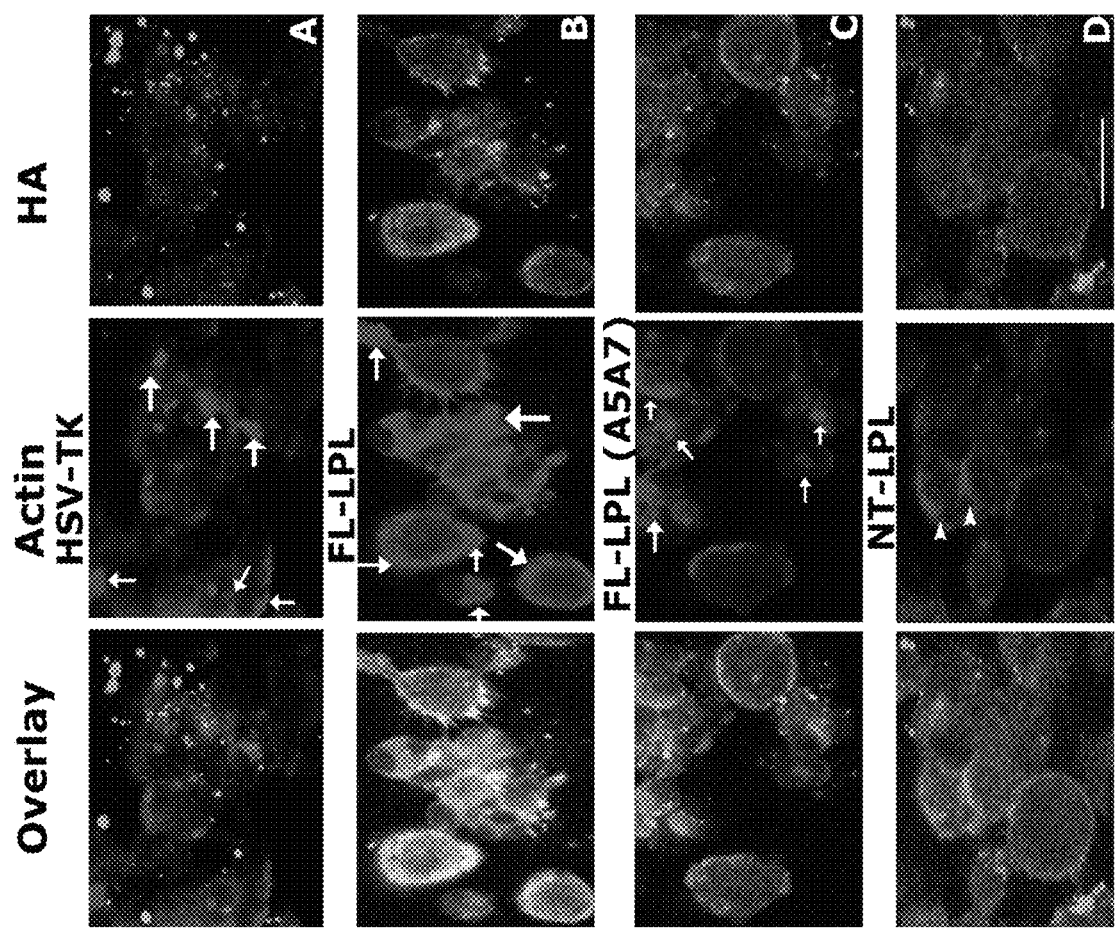
FIG. 7, comprising

Changes in NSZs formation in many osteoclasts transduced with various TAT-fused peptides are shown at lower magnification (FIG. 7). Transduction of HSV-TK or mutated FL-LPL (A5A7) did not affect the formation of basal level NSZs (FIG. 7A and FIG. 7C). Failure of colocalization of these transduced peptides (green) with actin in these NSZs suggests that the endogenous or cellular LPL regulates the formation of these NSZs. Most remarkably, the colocalization (yellow) of the transduced FL-LPL peptide with actin (red) suggests that those NSZs are formed by the actin bundling process mediated by the transduced FL-LPL (FIG. 7B). Nevertheless, the number of NSZs are very minimal in osteoclasts transduced with NT-LPL (FIG. 7D). This observation establishes that NT-LPL peptide has the potential to efficiently suppress the actin bundling activity via competitive inhibition of endogenous LPL phosphorylation as shown in FIG. 2.

Figure 4:
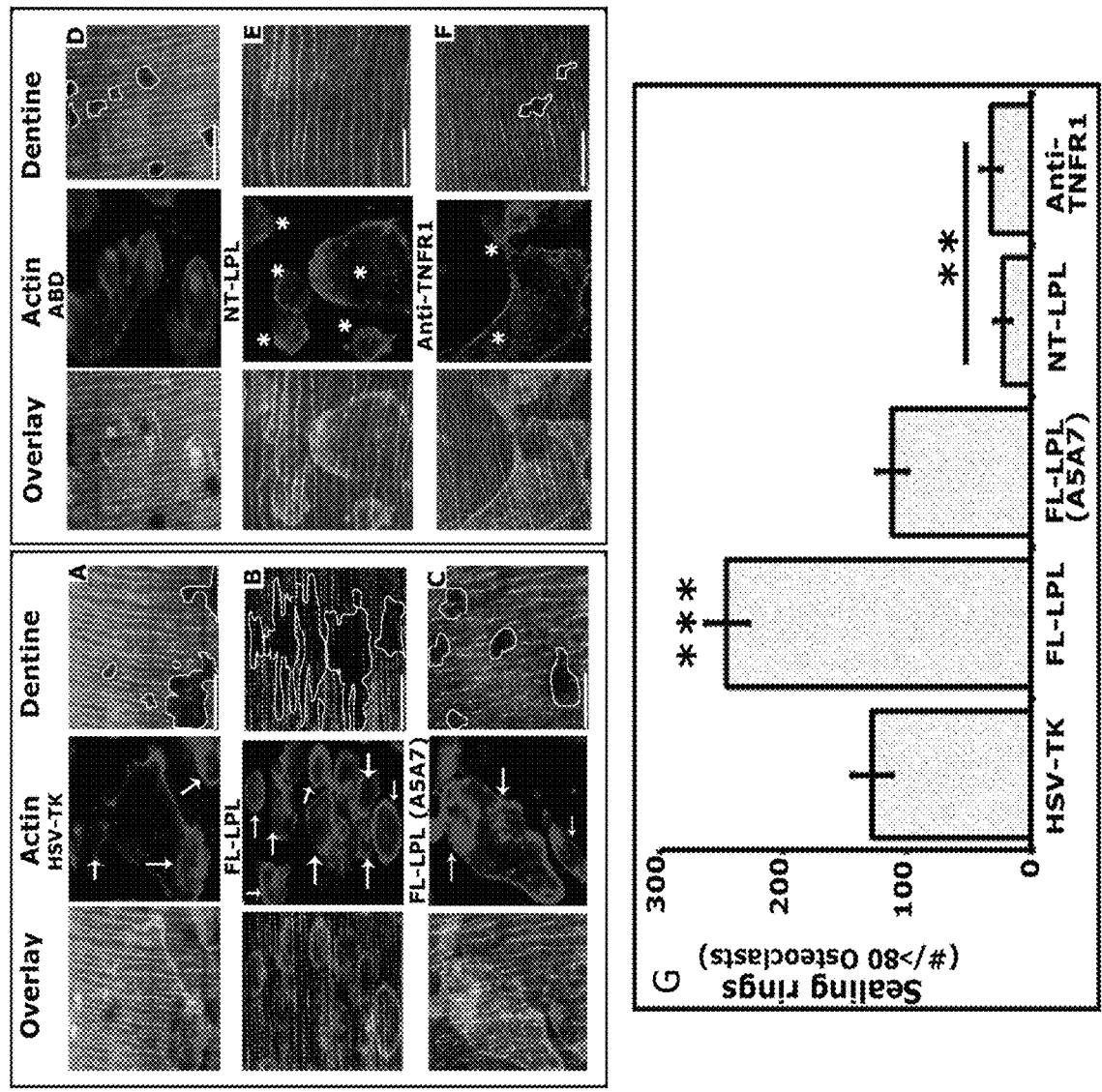
FIG. 4, comprising
Figure 5:
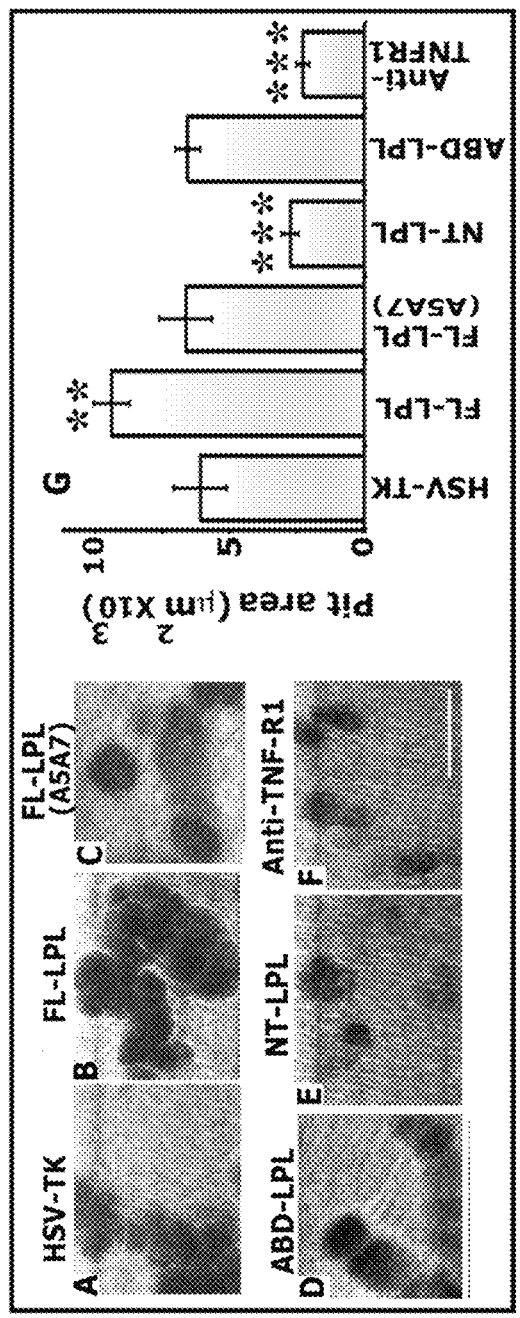
FIG. 5, comprising

Analysis of the Effect of Transduced TAT Fused LPL Peptides on the Formation of Scaling Rings and Resorption Pits in Osteoclasts Plated on Dentine Next, experiments were conducted to examine whether the inducible and inhibitory effects of FL-LPL and NT-LPL, respectively, have an impact on the formation of fully functional sealing rings and bone resorption. Osteoclasts plated on dentine for 10-12 hours in the presence HSV-TK (FIG. 4A), FL-LPL (FIG. 4B), FL-LPL (A5A7; FIG. 4C), ABD (FIG. 4D), NT-LPL (FIG. 4E) and neutralizing antibody to TNFR-1 (FIG. 4F) were stained for actin with rhodamine phalloidin (red). Distribution of sealing rings (red) and scans of dentine slices (green-pseudocolor) are shown (FIG. 4). Scaling rings (indicated by the arrows in FIG. 4A-FIG. 4D) that are capable of resorbing the dentine matrix and pits were found underneath those sealing rings (overlay panels of FIG. 4A-FIG. 4C). Resorption pits were outlined with white lines in green panels representing dentine slice. Sealing rings counted in 80-100 osteoclasts are expressed as sealing rings per osteoclasts in the graph provided (FIG. 4G). The number of sealing rings was increased in osteoclasts transduced with PL-LPL Multiple sealing rings were observed in osteoclasts transduced with FL-LPL (FIG. 4B and FIG. 4G) as compared with cells transduced with HSV-TK (FIG. 4A and FIG. 4G) or mutant FL-LPL (FIG. 4C). Multiple resorption pits underneath the sealing rings suggest that the sealing rings formed were efficient and functional. An increase in the number of sealing rings corresponds with an increase in the number and size (area) of resorption pits (FIG. 5B and FIG. 5G). A significant decrease in the formation of NSZs (FIG. 3) with NT-LPL peptide corresponds with a reduction in sealing ring formation and resorption (FIG. 4E, FIG. 4G, FIG. 5E, and FIG. 5G). FL-LPL and NT-LPL have opposing effects on actin ring formation and resorption which indeed is comparable to their impact on the NSZs formation. A decrease in the number of NSZs and sealing rings (FIG. 3 and FIG. 4) by a neutralizing antibody to TNF receptor 1 (TNFR1) also corresponds with a decrease in resorption function (FIG. 5F and FIG. 5G). These observations suggest that TNF-α signaling regulates LPL phosphorylation. NSZs seem to be the precursor zones from which maturation of fully functional sealing rings ensues.

Figure 6:
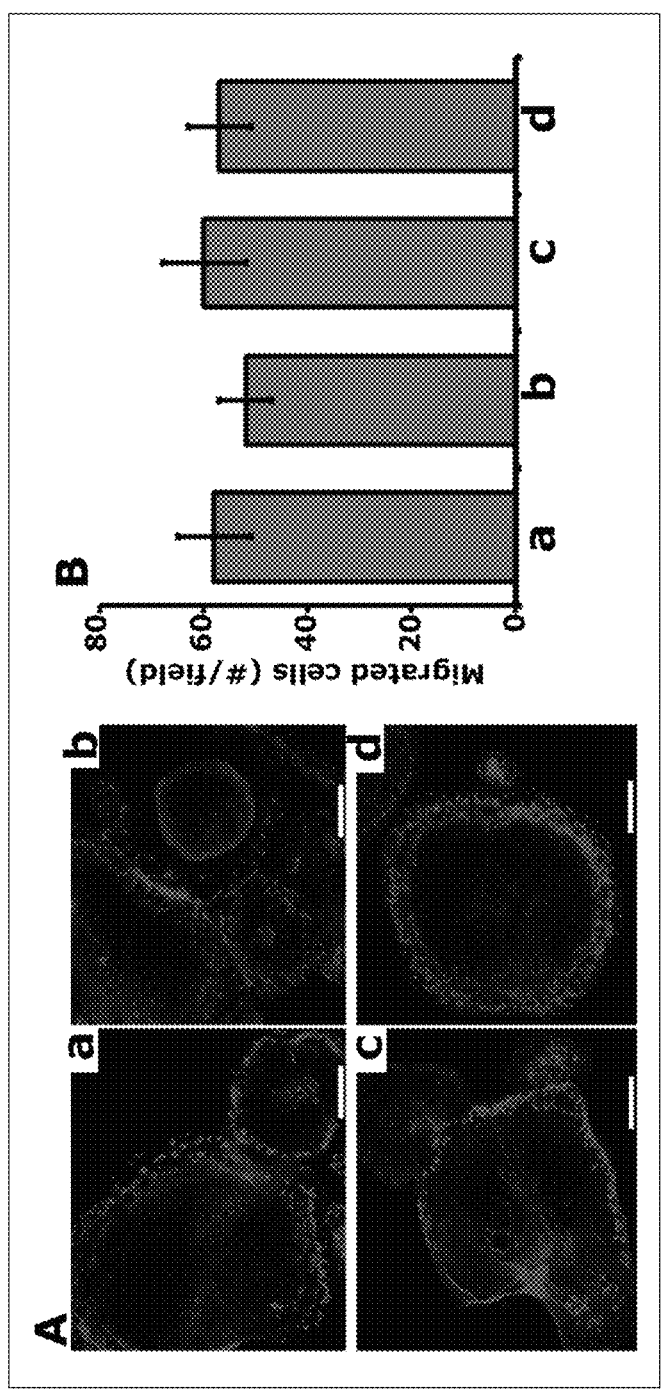
FIG. 6, comprising FIG. 6A

Analysis of the Effect of Transduced TAT Fused LPL Peptides on the Formation of Podosomes and Migration LPL (aka fimbrin) was shown to localize in the podosomes of osteoclasts (de Arruda et al., 1990, J. Cell Biol., 111:1069-1079). However, studies on the role of LPL in actin modulation, podosome assembly/disassembly, and migration are limited. Having shown that NT-LPL peptide has the potential to reduce NSZs formation via, suppressing the function of endogenous LPL in osteoclasts, experiments were conducted whether this peptide would have a similar inhibitory effect on actin modulation involved in podosome assembly/disassembly and migration (FIG. 6A and FIG. 6B). TAT-fused FL-LPL (a), mutated FL-LPL (b), ABD (c), and NT-LPL (d) does not affect the actin modulation involved in podosome assembly/disassembly (FIG. 6A) and migration (FIG. 6B). Actin staining was observed in the podosomes of osteoclast treated with indicated peptides. It is concluded that LPL is indispensable to drive the actin bundling processes involved in sealing ring formation.

Role of LPL in Bone Resorption

The process of sealing ring formation in osteoclasts requires significant actin filament reorganization; bundling and stability of actin filaments are fundamental steps in the formation of sealing rings, which allow osteoclasts to adhere to the bone surface tightly. The data provided herein show that LPL regulates the actin bundling process at the early stage of sealing ring formation. Cooperativity between serine phosphorylation and actin binding to ABDs of LPL is required for the actin bundling process mediated by LPL. A novel mechanistic link between LPL and cortactin in the formation of sealing ring was previously demonstrated. Cyclical changes in the levels of LPL protein and phosphorylation corresponded well with the actin cytoskeletal reorganization in resorbing osteoclasts. NSZs function as secondary adhesive sites during membrane extensions. Present results corroborate previous observations (Ma et al., 2010, J. Biol. Chem., 285: 29911-29924) that polymerization of actin generates a force to push the plasma membrane forward to produce membrane extensions. NSZs formed at the extensions serve as adhesive structures which facilitate spreading of osteoclasts on bone.

It was understood that towards the beginning of the resorption phase, sealing rings are formed from the fusion of podosomes (Lakkakorpi et al., 1991, J. Bone Miner. Res., 6: 817-826; Lakkakorpi et al., 1996, Microse Res Tech., 33; 171-181; Teti et al., 1991, Amer. J. Physiol., 261; C1-C7). However, various findings have suggested that sealing rings formed on bone have a unique three-dimensional organization that is not derived from podosomes. Podosomes do not fuse together to form sealing rings on the dentine slice or mineralized matrix (Jurdic et at, 2006, Eur. J. Cell Biol., 85: 195-202; Saltel et al, 2004, Mol. Biol. Cell, 15: 5231-5241). It has also been suggested that podosomes may transform from individual dynamic structures to two-dimensional clusters. From these clusters, highly dynamic rings are formed, which eventually stabilize. This transition correlates with enhanced actin reorganization and a 10-fold increase in the amounts of F-actin (Luxenburg et al., 2007, PLoS.ONE., 2: e179). Podosomes do not require adhering firmly to extracellular matrix (ECM) as they are rapidly constructed and removed. Their half-life is about 2-12 minutes (Kanehisa et al., 1990, Bone, 11: 287-293). The sealing ring is supposed to have very close and stable adhesion to ECM on the bone surface to generate tight sealing zone. Osteoclasts transduced with NT-LPL peptide did not have any effect on the actin modulation involved in the formation of podosomes. This suggests that the bundling of the actin filaments is not one of the processes involved in the formation of podosomes. However, NT-LPL peptide blocked the formation of NSZs. NSZs are several folds larger than the typical podosome structures. These observations are consistent with the suggestions made by others (Luxenburg et al., 2007, PLoS. ONE., 2: e179) in the formation of actin-rich aggregates before the establishment of sealing rings. Even so, if one considers that sealing rings are derived from podosomes, there should be remarkable changes in the reorganization of actin filaments because of the architectural nature of podosomes and sealing rings.

NSZs represent a part of the phenotypic changes that occur before the formation of scaling rings on mineralized matrix. The contemporary view of actin reorganization in sealing ring formation and resorption activity have focused predominantly on integrin $\alpha v\beta 3$ signaling (Batsir et al., 2017, Cytoskeleton (Hoboken.), 74: 72-81; Biswas et al., 2004, BMC. Cell Biol., 5: 19; Chellaiah et al., 2007, J. Biol. Chem., 282: 10104-10116; Duong et al., 1998, J. Clin. Invest., 102: 881-892; Faccio et al., 2002, J Cell Sci., 115: 2919-2929; Feng et al., 2001, J Clin. Invest, 107: 1137-1144; Georgess et al., Cell Adh. Migr., 8: 191-204; Hartman et al., 2000, Expert. Opin. Investig. Drugs, 9: 1281-1291; Izawa et al., 2012, Mol. Cell Biol., 32; 2943-2953; Lee et al., 2015, Biomed. Res. Int., 2015: 680145; Chellaiah et al., 2009, J Cell Physiol. 220:382-393: Ma et al., 2010, J. Biol. Chem., 285: 29911-29924; Miyazaki et al., 2004, J. Biol. Chem., 279: 17660.17666; Nakamura et al., 1999, J. Cell Sci., 112 (Pt 22): 3985-3993; Novack et al., 2011, Ageing Res. Rev., 10: 54-61; Soysa et al., 2015, Biochem. Biophys. Res. Commun., 476: 115-120; Teitelbaum, 2011, Ann. N.Y. Acad. Sci., 1240: 14-17). Osteoclasts from integrin β3 knockout mice (McHugh et al., 2000, J. Clin. Invest., 105: 433-440) expressing a cytoplasmic domain deleted β3 constructs (Feng et at, 2001, J Clin. Invest., 107: 113741144) or treated with echistatin (Nakamura et al., 1999, J. Cell Sci., 112 (Pt 22): 3985.3993) in fact have shown actin aggregates (Feng et al., 2001, J Clin. Invest., 107: 1137-1144; Nakamura et al., 1999, J. Cell Sci., 112 (Pt 22): 3985-3993). It is possible that these aggregates may not be considered as an important zone at the time of these observations. Regulation of the formation of NSZs by TNF-α or RANKL signaling provides a new concept in osteoclast bone resorption. Identification of formation of NSZs prior to sealing ring formation and localization of integrin $\alpha v\beta 3$ in the NSZs provides a paradigm shift from the existing model of "OC adhesion to the bone surface → assembly of sealing rings by $\alpha v\beta 3$ signaling → bone resorption" to the new model of "OC adhesion to the bone surface→ formation of nascent sealing zones by TNF-α or RANKL signaling→ maturation of NSZs to sealing rings by $\alpha v\beta 3$ signaling→ bone resorption".

Sealing rings consisting of stable actin filaments that generate tight sealing zones on the bone surface. The areas encompassed by actin filaments in sealing rings range from 1-10 μm (Luxenburg et al., 2006, Eur. J. Cell Biol., 835: 203-211). Because of the architectural nature of sealing rings, a major reorganization of actin filaments is required during their formation. LPL was shown as one of the bundling proteins which cross-links actin filaments to tight bundles (Delanote et al., 2005, Acta Phamacol. Sin., 26: 769-779; Foran et al., 2006, Int. J. Cancer, 118: 2098-2104; Frederick et al., 1996, Cancer Res., 56: 138-144; Luxenburg et al., 2006, Eur. J. Cell Biol., 85: 203-211; Winder et al., 2005, J. Cell Sci., 118: 651-654). Actin bundling is mediated by two tandem repeats of actin-binding domains (ABD) in LPL. These domains assist in binding two actin filaments into parallel arrays for bundle assembly (Hanein et at, 1998, Nat. Struct. Biol., 5: 787-792; Namba et al., 1992, J. Biochem. (Tokyo), 112: 503-507: Volkmann et al., 2001, J. Cell Biol., 153: 947-956). Actin-binding proteins which have two discrete actin-binding domains nearby can achieve the process of actin bundling (Winder et at, 2005, J. Cell Sci., 118: 651-654). Although, osteoclasts express alpha (α)-actinin, which is also an actin-bundling protein, actin bundles generated by α-actinin are loose structures as seen in actin stress fibers (Luxenburg et. al, 2006, Eur. J. Cell Biol., 85: 203-211; Marchisio et al., 1987, Exp. Cell Res., 169: 202-214). This is because ABDs are placed at a distance in α-actinin and separated by a helical spacer region. LPL seems to be an appropriate protein in the tight bundling of actin filaments essential for osteoclast bone resorption. LPL was also shown to stabilize actin filaments and protect them against depolymerization (Lebart et at, 2004, Biochemistry, 43: 2428.2437), which is a must for the efficient function of sealing ring during bone resorption.

Phosphorylation of LPL on Ser-5 and -7 residues was shown to be essential for actin binding/bundling activity of LPL (Janji et al., 2006. J. Cell Sci., 119: 1947-1960). In the experiments described herein, transduction of TAT-fused NT-LPL peptide into osteoclasts allowed for the correlation of the observed actin modulation with LPL functional domains. Analyses with TAT-fused LPL peptides not only revealed the feasibility of the techniques but also the ability of the peptides to induce changes in the actin cytoskeleton of resorbing osteoclasts. An increase in F-actin content, number of NSZs and sealing rings in osteoclasts transduced with FL-LPL peptide showed the significance of LPL in the formation of NSZs. Also, NT-LPL peptide partially or entirely blocked the phosphorylation of endogenous LPL. This is reflected in the organization of NSZs and sealing rings as well as resorption activity. The data derived from experiments with NT-LPL, ABD and mutated FL-LPL at serine residues elucidate the specific role of LPL phosphorylation on NSZs formation. Serine phosphorylation of LPL is a necessary process in the effects mediated by ABD such as bundling and stabilization of actin filaments. Therefore, no additional results in the formation of actin aggregates were observed in osteoclasts transduced with either mutated FL-LPL (A5A7) or ABD.

The findings herein, a) indicate that phosphotylation of LPL on serine residues regulate actin bundling via two ABDs. b) demonstrate the significance of LPL phosphorylation and function in NSZs formation at the early stage of sealing ring formation. c) demonstrate that phosphorylation of LPL acts as an integrator of signals that control the actin bundling action. d) show that LPL stabilizes actin bundles to mature into sealing rings. These studies identify LPL as a novel therapeutic target in osteoclast-mediated events.

Example 2: Peptidomimetic Inhibitors of L-Plastin Reduce the Resorptive Activity of Osteoclast but not the Bone Forming Activity of Osteoblasts In Vitro Sealing ring formation is a requirement for osteoclast function. As described above, the actin-bundling protein L-plastin plays a role in the assembly of nascent sealing zones (NSZs) at the early phase of sealing ring formation in osteoclasts. TNF-α signaling regulates this actin assembly by the phosphorylation of L-plastin on serine-5 and -7 residues at the amino-terminal end. These NSZs function as a core for integrin localization and coordinating integrin signaling required for maturation into fully functional sealing rings. The experiments presented herein were conducted to elucidate the essential function of L-plastin phosphorylation in actin bundling, a process required for NSZs formation. The present study was undertaken to determine whether targeting serine phosphorylation of cellular L-plastin would be the appropriate approach to attenuate the formation of NSZs.

The experiments described herein use TAT-fused small molecular weight (10aa) amino-terminal-LPL peptides ((sNT)-LPL; "$^1$MARGSVSDEE$^{10}$" (SEQ ID NO: 1)) containing phospho-Ser-5 and Ser-7 (PL; also represented as unsubstituted) and substituted peptides with Ala-5 and -7 for Ser-5 and Ser-7 (P2-P4), lmmunoblotting, actin staining, and dentine resorption analyses were done to determine cellular L-plastin phosphorylation, NSZ or sealing ring formation, and osteoclast function, respectively. Immunoblotting for bone formation markers, Alizarin red staining and alkaline phosphatase activity assay have been done to determine the effect. It is shown herein that transduction of unsubstituted (P1) and substituted peptides at either Serine 5 or Serine 7 with Alanine (P3 and P4) demonstrated variable inhibitory effects on the phosphorylation of cellular L-plastin protein. Peptide Pt reduces substantially 1) cellular Lplastin phosphorylation; 2) formation of nascent sealing zones and sealing rings and 3) bone resorption. Substitution of both Serine-S and 0.7 with Alanine (P2) had no effects on the inhibitory activities described above. Furthermore, either the L-plastin (P1-P5) or (P6) control peptides had a little or no effect on the a) assembly/disassembly of podosomes and migration of osteoclasts; b) mineralization process mediated by osteoblasts in vitro.

Thus, the experiments presented herein demonstrate that small molecular weight peptidomimetics of L-plastin inhibits bone resorption by osteoclasts via attenuation of NSZ and sealing ring formation but not bone formation by osteoblasts in vitro. Thus, L-plastin provides a valuable therapeutic target to treat and prevent diseases associated with bone loss without affecting bone formation.

The materials and methods used in these experiments are now described.

Materials

Antibody to L-plastin (SC-16657; Goat) was bought from Santa Cruz Biotechnology, Inc. (Santa Cruz, Calif.). Antibodies to GAPDH was purchased from R & D Systems (Minneapolis, Minn.) and Sigma (St. Louis, Mo.). Protein estimation reagent, molecular weight standards for proteins, and PAGE reagents were bought from Bio-Rad. Cy2- and Cy3-conjugated secondary antibodies were purchased from Jackson Immunoresearch (West Grove, Pa.). HRP-conjugated secondary antibodies for immunoblotting were obtained from GE Healthcare. Antibody to phosphoserine (p-Serme) was bought from Zymed laboratories (61-8100) or Millipore (AB1603). Alizarin red solution was bought from Life-line Cell Technology (CM-0058; Fredrick, Md.) Rhodamine-phalloidin and other chemicals were purchased from Sigma (St. Louis, Mo.).

Studies in Osteoclasts

Mia

C57/BL6 mice (six to eight-week-old mice) were used for osteoclast preparation.

Preparation of Osteoclast Precursors from Mice and Treatment of Osteoclasts with Bone Particles C57/BL6 mice were used for osteoclast preparation as described previously (Chellaiah et al., 2000, J. Cell Biol., 148: 665.678; Chellaiah et al., 2007, J. Biol. Chem., 282: 10104-10116). Osteoclasts were generated in vitro using mouse bone marrow (BM) cells as described (Chellaiah et al., 2000, J. Cell Biol., 148: 665-678; Chellaiah et al., 2007, J. Biol. Chem., 282: 10104.10116). Osteoclasts differentiated from RAW 264.7 cells were also used to corroborate a few of the observations made with osteoclasts derived from mouse BM cells. Osteoclasts from RAW 264.7 cells were generated as described previously (Gupta et al., 2003, J Bone Miner Res 18: 669-685). Conditions were established that offer >90% population of mature multinucleated osteoclasts from both mouse bone marrow and RAW cells.

Treatment of Osteoclasts with Bone Particles

After flushing the marrow cells for osteoclast differentiation, long mouse bones (free of cells inside and muscles outside) were washed extensively with PBS and kept in ethanol until use. Long bones were air-dried in the hood and homogenized by a mini blender. Bone particles were sieved, and bone particles 60-80 μm in size were used for experiments. The multinucleated osteoclasts were seen from day four onward from mouse BM or RAW cells. At this stage, osteoclasts were added with sterile native bone particles (100 μg/ml medium) for 3-4 hours or 12-14 hours in the presence of TNF-α (20 ng/ml).

Transduction of TAT-Fused sNT-LPL Peptides into Osteoclasts

After cells were kept in the serum-free α-MEM medium for two hours, LPL peptides of interest were added to a final concentration of 100-150 nM to cells in serum-free media (Chellaiah et al, 2000, J. Biol. Chem., 275: 11993-12002). Osteoclasts transduced with peptides of interest and added with bone particles in the presence of TNF-α for 3-4 hours or 12-14 hours were used for lysate preparations. Cells plated on coverslips and treated with peptides were used for actin staining to detect podosomes. After transduction for 30 min., osteoclasts were re-plated on dentine slices with respective LPL peptide and TNF-α for 3-6 hours or 12-14 hours. These cells were used for Actin staining with rhodamine-phalloidin or immunostaining analyses (Chellaiah et al., 2000, J. Biol. Chem., 275: 11993-12002; Chellaiah et al., 2000, J. Cell. Biol., 148: 665-678; Chellaiah et al., 2003, J Biol Chem 278: 29086-29097).

Lysate Preparation

Following various treatments, osteoclasts were washed three times with cold PBS and lysed in a Triton-containing lysis buffer as described (Chellaiah et al., 1996, Mol. Biol. Cell, 7: 743-753). Cells were rocked on ice for 15 minutes, and scraped off with a cell scraper. Cell lysates were centrifuged at 15,000 rpm for 5 minutes, at 4° C., and the supernatant was saved. Protein contents were measured using Bio-Rad protein assay reagent. Osteoclast cultures were also subjected to a trypan blue dye (Sigma T8154) exclusion test to determine the viability of osteoclasts after various treatments. Cells demonstrated clearcytoplasm with no inclusion of blue dye (Ma t al., 2010, J. Biol. Chem., 285: 29911-29924).

Immunoprecipitation and Immunoblotting (IB) Analyses

About 50-100 µg of lysate protein from mouse osteoclasts and 20-30 µg of lysate protein from RAW cell-derived osteoclasts was used for immunoprecipitation and immunoblotting analyses. Immunoprecipitation with an LPL antibody was done as described previously (Chellaiah et alt, 1996, Mol. Biol. Cell, 7: 743-753). The proteins were transferred to a PVDF membrane for IB analysis after 10% SDS-PAGE. Blots were blocked with 10% milk in PBS containing 0.5% Tween (PBS-T) for 2-3 hours and then incubated with 1:1000 dilutions of a primary antibody of interest for 2-3 hours. After three washes for 10 minutes each with PBST, the blot was incubated with a 1:1000 dilution of peroxidase-conjugated species-specific respective secondary antibody for 2 hours at room temperature. After three washes for 10 minutes each with PBS-T, protein bands were visualized by chemiluminescence using the ECL kit (Pierce) (Chellaiah et al., 1996, Mol. Biol. Cell, 7: 743-753).

Immunohistochemistry and Actin Staining

Osteoclasts were fixed with 3% paraformaldehyde for 20 minutes and permeabilized with 0.1% Triton X-100 in PBS for 5 minutes. Subsequently, osteoclasts were stained with a primary (HA or integrin αv) and secondary antibody as described (Chellaiah et al., 2003, J Biol Chem 278: 29086-29097). Actin staining was done with rhodamine-phalloidin as described (Chellaiah et al., 2000, J. Biol. Chem., 275: 11993-12002; Chellaiah et al., 2000, J. Cell Biol., 148: 665-678). Cells were washed and mounted on a slide in a mounting solution (Vector Laboratories) and sealed with nail polish. Immunostained osteoclasts were photographed with a Bio-Rad and Nikon confocal microscope. Images were stored in TIF image format and processed by Adobe Photoshop (Adobe Systems Inc., Mountain View, Calif.).

Measurement of F-Actin Content Using Rhodamine-Phalloidin Binding

Osteoclasts were transduced with LPL and control peptides. For each treatment four to six wells in 24 well culture dishes were used. Cells were fixed and rhodamine phalloidin binding to F-actin was done as described (Chellaiah et al., 1998, J. Biol. Chem., 273: 11908-11916; Chellaiah et al., 1996, Mol. Biol. Cell, 7: 743-753).

Dentine Resorption Lacuna and Migration Assays

Resorption was evaluated using dentine slices as described previously (Chellaiah et al., 2000, J. Biol. Chem., 275: 11993-12002). After transduction for 30 minutes, osteoclasts were re-plated on dentine slices for 12-16 hours to detect resorption lacuna in the presence of respective LPL peptide and TNF-α. Each treatment was done in quadruplicates Subsequently, dentine slices were stained with Mayer's acid hematoxylin (Sigma) for 6 minutes followed by washing several times with water. Excess stain in the resorbed area and stained cell debris were removed with a cotton swab. The pits were imaged under an X40 objective in a Zeiss inverted phase contrast microscope fitted with a CCD camera (Chellaiah et al., 2003, J Biol Chem 278: 29086-29097; Chellaiah et al., 2003, Mol Biol Cell, 14: 173-189). Images were stored in TIF format and processed by Adobe Photoshop (Adobe Systems Inc.).

Cell migration (phagokinesis and transwell migration) assays were done as described previously (Chellaiah et al., 2000, J. Cell Biol., 148: 665-678). Osteoclasts transduced with sNT-LPL peptides (P1, P2, P5, and P6) were used for these assays. Three to four transwells were used for each treatment. Migrated cells at the bottom of the wells were counted in 3-4 independent fields/transwell filter. Data are presented as migrated cells/field (mean±SD). The experiment was repeated with three osteoclast preparations. In phagokinesis assay, cell motility was assessed by measuring the areas free of gold particles. By using a grided reticule (Boyce Scientific. Inc.) in the eyepiece of a Nikon microscope, areas free of gold particles were measured using a 10× objective. Areas free of gold particles were represented as area moved in $mm^2$ (Chellaiah et al., 2000, J. Cell Biol., 148: 665-678), Studies in Osteoblasts Osteoblast Cultures and Bone Mineralization Analyses Both MC3T3 and UMR106 cells were used for the assays to detect bone mineralization. Approximately $3\times10^5$ MC3T3 cells were cultured in osteogenic medium (αMEM+10% fetal bovine serum supplemented with 50 mM ascorbic acid and 10 mM β-glycerophosphate) for seven days in the presence of sNT-LPL peptides of interest (100 nM). UMR-106 cells were plated at $0.6\times10^6$ density in a 6-well plate for ALP activity assay and $0.4\times10^6$ in 24-well plate for Alizarin Red S staining (ARS). Cells were maintained in Dulbecco's Modification of Eagles Medium (DMEM) containing 10% FBS (Benchmark), 1% penicillin/streptomycin, and 0.05% gentamicin. After reaching 90-95% confluency, the culture medium was replaced with osteogenic medium (7 mM β-glycerophosphate (Sigma), 50 µM ascorbic acid 2-phosphate (Sigma)) for seven days (Li et al., 2016, Asian J Androl 18: 716-722). sNT-LPL peptides (100 ng) of interest were added to cultures every 20-24 hours for seven days. Cell counting Kit-8 (CCK-8; Sigma) was used in parallel cultures treated as above to determine the viability.

Alizarin Red S Staining (ARS)

After seven days, cells washed three times with PBS were fixed with 4% formaldehyde in PBS for 30 minutes at room temperature (RT). After washing one time with PBS, 2% Alizarin red stain solution was added to each well and incubated for 45 minutes at RT. Then, wells were washed with tap water three times to remove unincorporated excess dye before scanning the plate in an EPSON Perfection V200 Photo scanner. Magnified pictures of the wells were taken using a phase contrast microscopy (Nikon) using 10× or 20× objective.

Alkaline Phosphatase (ALP) Activity Assay

For ALP activity, cells were washed with cold PBS three times and added with lysis buffer (50 mM Tris, 0.1% Triton-x, 1 mM $MgCl_2$, and 100 mM glycine). Lysates were centrifuged at 10,000×g (13000 RPM) for 5 minutes. An equal amount of supernatant protein was used triplicates in a 96-well plate to measure the activity. P-Nitrophenyl phosphate (100 µl; Sigma) was added to each well and absorbance was measured at 405 nm using microplate reader (Cytation3 image reader) with software (Gen5 version 2.09).

Immunoblotting

UMR-106 cells were grown as described above and sNT-LPL peptide of interest (100 nM) were added to cultures every 20-24 hours for seven days. Cells grown in osteogenic medium only were used as controls. The cells were lysed in RIPA lysis buffer containing protease inhibitors (Chellaiah et at, 2000, J. Biol. Chem., 275: 11993-12002). Lysates were incubated on ice for 15 minutes and then centrifuged at 10000×g (13,000 RPM) for 15 minutes at 4° C. The supernatant was collected and the protein concentration was determined using Bradford assay. An equal amount of lysates (10 µg) were subjected to either 8% or 10% SDS-PAGE and transferred to PVDF membranes. Western blotting was done with antibodies to collagen (1:2000) (Novus Biologicals), Runx2 (1:1000) (Santa Cruz), or osterix (1:1000) (Millipore) as described previously (Chellaiah et al., 1998, J. Biol. Chem., 273: 11908-11916; Chellaiah et at, 1996, Mol. Biol. Cell, 7: 743-753). Western blotting with a GAPDH antibody (Sigma) was used as a control for loading.

Statistical Analysis

Data obtained represent the response of the osteoclast culture as a whole (>85% multinucleated giant cells and ~10-15% osteoclast precursors). Statistical significance was determined using either analysis of variance ANOVA or student's t-Test (INSTAT; Version 6.0, Graph Pad software, Graph Pad Inc, San Diego, Calif.). Results are presented as means±SD, A probability value<0.05 was considered to be statistically significant and <0.01 was considered to be highly significant.

The results of the experiments are now described.

Analysis of the Effect of Transduction of TAT-Fused sNT-LPL Peptides on the Phosphorylation of Cellular LPL Previous studies have shown that the actin bundling process is dependent on the phosphorylation of LPL (Ma et al., 2010, J. Biol. Chem., 285: 29911-29924; Delanote et al., 2005, Acta Pharmacol. Sin., 26: 769-779; Al et al., 2010, PLoS ONE, 5, e9210; Morley, 2013, Immunol Rev. 256: 48-62). Most experiments concerning LPL function have been performed in PMNs. Jones et al. analyzed the function of LPL by introducing LPL-derived peptides containing the NT-region into PMNs (Jones et at, 1998, Proc. Natl. Acad. Sci. U.S.A, 95: 9331-9336). The dynamic localization of the proteins L-Plastin and cortactin in regulating actin polymerization has been characterized. Further, the possible molecular interactions involved in the process of NSZs and sealing ring formation by these proteins has been defined (Ma et al., 2010, J. Biol. Chem., 285: 29911-29924). Here, experiments are conducted to identify the essential function of phosphorylation on Ser-5 and 7 by TNF-α signaling in actin bundling, a process required for NSZ formation by LPL.

In this context, it was examined whether an sNT-LPL peptide containing Ser-5 and Ser-7 ($^1$MARGSVSDEE$^{10}$ (SEQ ID NO: 1)) can be used as an inhibitor of endogenous (cellular) LPL phosphorylation and NSZs formation. Therefore, the following sNT-LPL peptides were generated (denoted as P1-P6) as shown in FIG. 8A: Unsubstituted (P1), Ser-5 and Ser-7 substituted to Alanine 5 and 7 (P2; A5A7), either Ser-5 (P3; A5S7) or Ser-7 (P4; S5A7) is substituted to Alanine, and scrambled (P5). TAT peptide (P6) alone was also used as a control.

Figure 16:
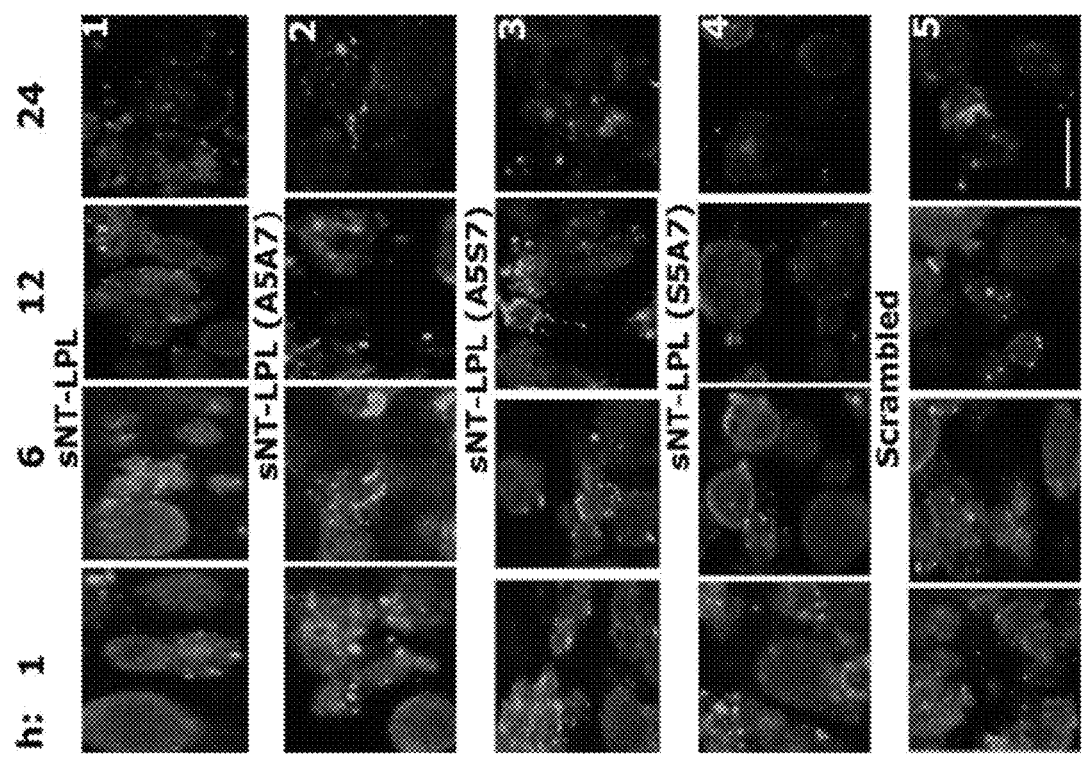
FIG. 16 depicts the results of example experiments demonstrating the time-dependent uptake of indicated TAT-fused sNT-LPL peptides (P1-P5) by osteoclasts. Confocal microscopy analysis of osteoclasts immunostained with a TAT-antibody is shown. TAT-stained osteoclasts at different times (1, 6, 12, and 24 hours) after transduction with indicated TAT-fused peptides are shown. Scale bar-150 μm.
Figure 17:
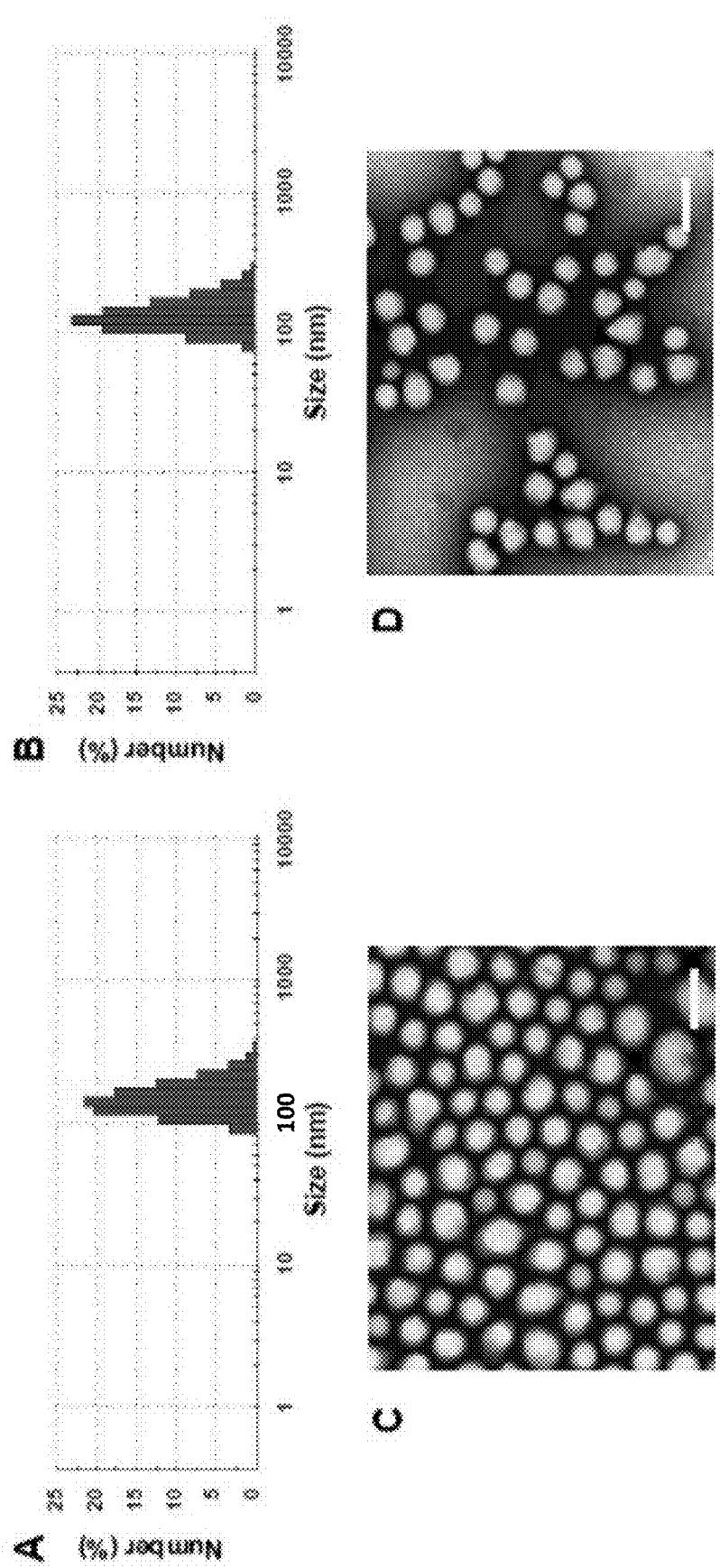
FIG. 17, comprising

First, the time-dependent uptake of peptides indicated in FIG. 5A was determined. Immunostaining analysis was done with a TAT antibody and fluorescent micrographs of transduced cells are shown at time points of 1, 6, 12, and 24 hours in FIG. 16. Diffuse staining is observed at all-time points tested. Transduction of the peptide is seen as early as 15-30 minutes the level is maintained until 10-14 hours and reduced after 20 hours.

Subsequently, immunoblotting of LPL immunoprecipitates was done with a p-Serine antibody (FIG. 8B). Osteoclasts treated with bone particles and TNF-α were transduced with indicated peptides (FIG. 8A) for 3-4 hours. Statistical analysis of the inhibition (%) of phosphorylation is shown in FIG. 8C. No significant inhibitory effect was observed on the phosphorylation of cellular LPL in osteoclasts transduced with P2 (FIG. 8B; lane 3), P5 (lane 6) and P6 (lane 7). However, varied inhibitory effects are shown with peptides P1, P3, and P4 (lanes 2, 4, and 5). The inhibition is significant with P1 peptide (FIG. 8B (lane 2) and FIG. 5C). Osteoclasts untransduced but treated with TNF-α and bone particles demonstrated basal level phosphorylation (lane 8) equal to the P2, P5, or P6 peptide transduced cells. Lysate made from osteoclasts transduced with P2 was used for immunoprecipitation with non-immune serum (lane 1). The levels of LPL protein in each immunoprecipitate are shown after stripping and reblotting with an antibody to LPL (FIG. 8B; LPL). These results show the ability of peptides to enter into osteoclasts. Also, it is shown that P1, P3, and P4 peptides have the potential to competitively suppress the serine phosphorylation of endogenous LPL in the following order P1>P3=P4. Immunoblotting of total lysates with an antibody to GAPDH validates that an equal amount of protein was used for immunoprecipitation (FIG. 8B; GAPDH).

Changes in F-actin levels is considered as a marker for cellular structural transformation (Rao et al., 1990, Cancer Res 50: 2215-2220). The transformation of actin cytoskeleton from podosome organization to sealing rings comprises both structural and quantitative modifications in resorbing osteoclasts. Rhodamine-phalloidin is a highly specific probe for filamentous actin. Therefore, to determine the quantitative changes in the F-actin levels in osteoclast treated with indicated peptides, a rhodamine-phalloidin binding assay was used, as previously described (Chellaiah et al., 1996, Mol. Biol. Cell, 7: 743-753). F-actin level decreased in osteoclasts treated with P1, P3 and P4 (FIG. 8D) as compared with P2, P5, and P6. The decrease was significant with P1 peptide (FIG. 8D) similar to the results observed in the serine phosphorylation of cellular LPL (FIG. 8B and FIG. 5C). The % inhibition on the F-actin level was observed in the following order: P1>P3=P4>P2=P5=P6.

Figure 8:
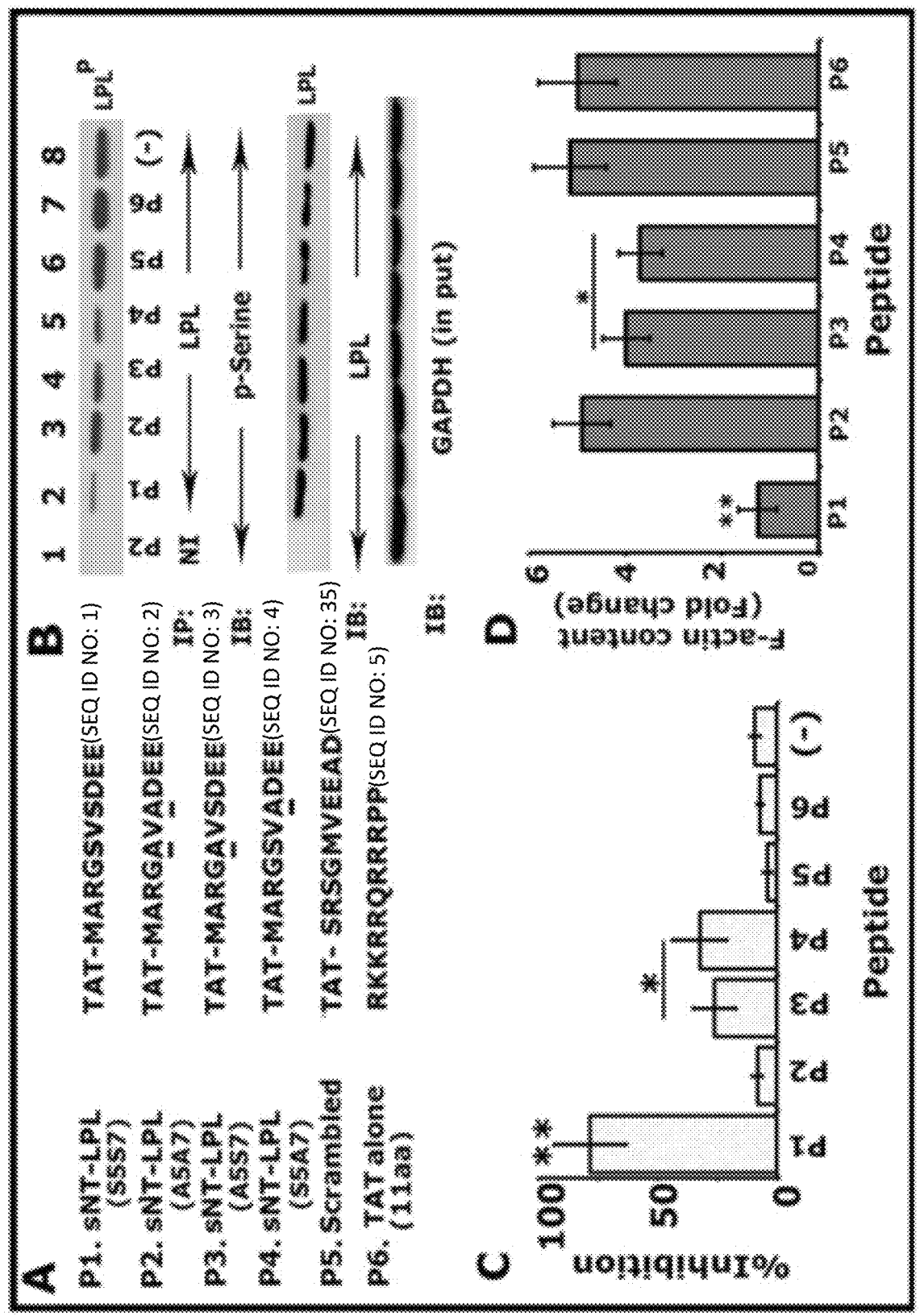
FIG. 8A through FIG. 8D, depicts the results of example experiments demonstrating that TAT-fused small molecular weight amino-terminal LPL (sNT-LPL) has the potential to reduce the phosphorylation of cellular LPL and total F-actin content
Figure 9:
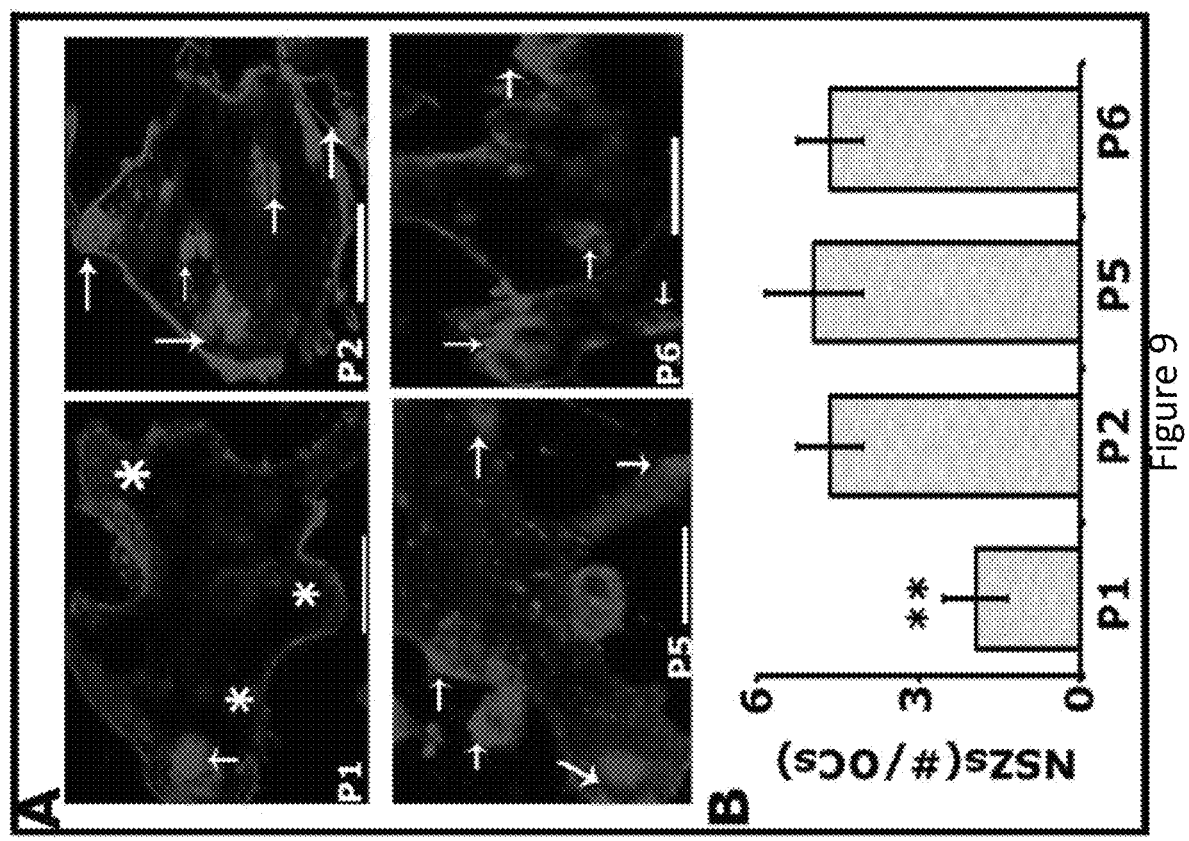
FIG. 9, comprising
Figure 10:
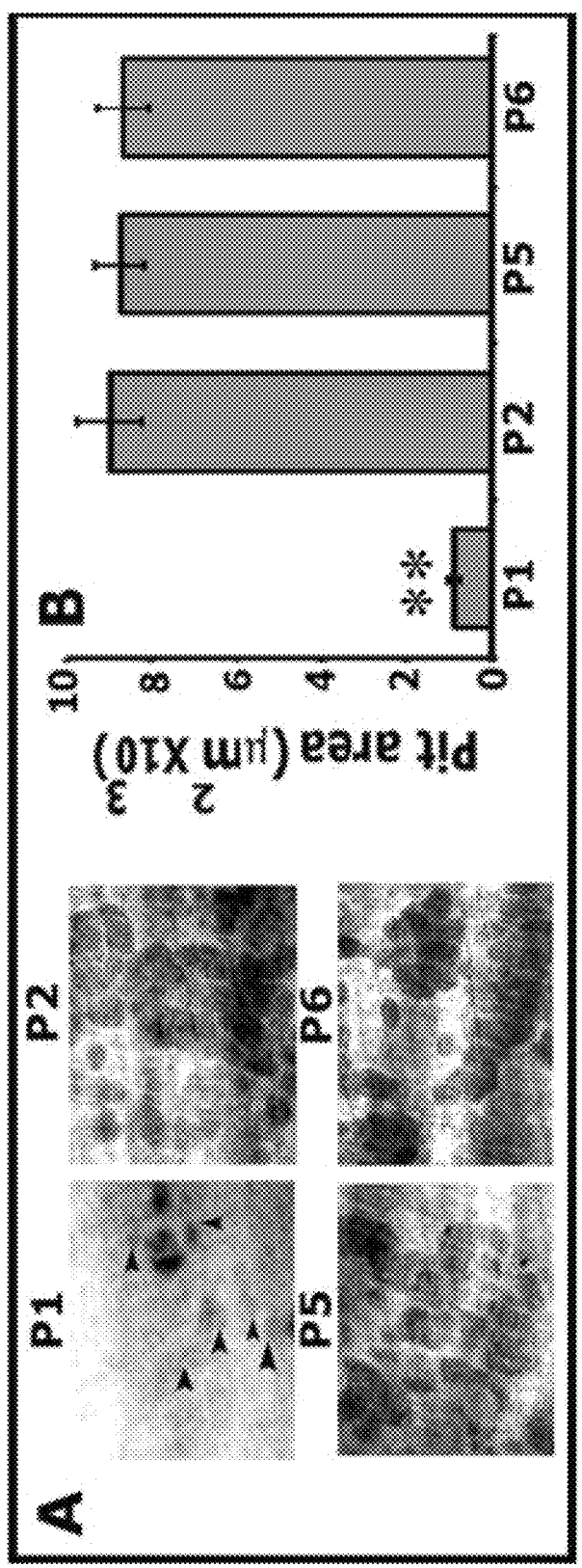
FIG. 10, comprising

Analyses of the Effect of LPL Peptides on Osteoclast Actin Modulation and Resorption of Dentine Matrix NSZs Formation and Resorption of Dentine Peptide P1 decreased the phosphorylation of cellular LPL and F-actin considerably (FIG. 8). Hence, to further define and highlight the impact of serine phosphorylation on the actin bundling process and osteoclast activity, the effects of P1 was compared with other peptides such as P2, P5, and P6 in the formation of NSZs (FIG. 9) and dentine resorption (FIG. 10). Peptides P2 and P5 act like the control TATpeptide (P6) with no inhibitory effect on the formation of NSZs (FIG. 9) and resorption of dentine matrix (FIG. 10). A considerable decrease in the formation of NSZs and the number was observed with the P1 peptide (FIG. 9). The decrease in the number of NSZs reflected on the resorption activity of these osteoclasts (FIG. 10). This also indicates that this is due to the impact of failure of formation of mature sealing rings.

Analyses of Localization of Integrin αv in NSZs and Sealing Ring Formation

Integrin αvβ3 plays a key role in the adhesion of osteoclasts on bone matrix and regulation of cytoskeletal organization essential for the formation of sealing rings (Miyauchi et at, 1991, Journal of Biological Chemistry, 266: 20369-20374; Nakamura et al., 1999, J. Cell Sci., 112 (Pt 22): 3985-3993; Duong et al., 1998, Front Biosci, 3: d757-d768). It was previously reported that localization of integrin in the NSZs is LPL-dependent and the maturation of the sealing rings from NSZs are under the regulation of integrin αvβ3 signaling (Ma et al., 2010, J. Biol. Chem., 285: 29911-29924). Therefore, experiments were conducted to clarify further whether attenuation of NSZs formation by P1 also affects the localization and function of αvβ3 as well as the formation of sealing rings in a time-dependent manner. Peptide 5 (scrambled) was used as a control.

Figure 11:
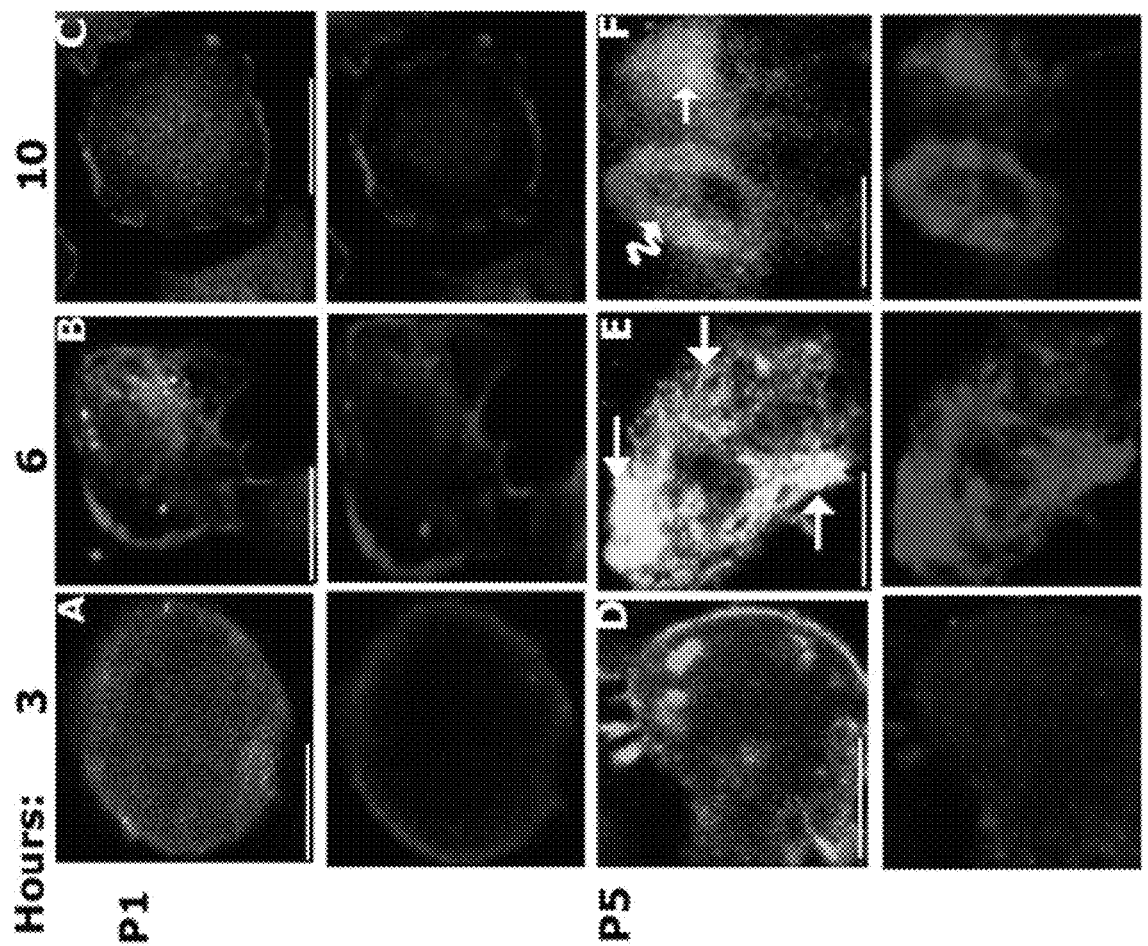
FIG. 11, comprising

Osteoclasts transduced with P1 and P5 (scrambled) peptides for 3.6, and 10 hours were immunostained with an LPL (green) and Integrin αv (red) antibody (FIG. 11). P1 peptide attenuates the formation of NSZs at 3 and 6 hours; therefore the localization of integrin αv in NSZs and the formation of the mature sealing rings are abrogated (FIG. 11A-FIG. 11C). Diffused distribution of LPL (green) and integrin αv (red) was observed in these osteoclasts. Also these proteins are not colocalized. However, osteoclast transduced with a P5 peptide demonstrated a time-dependent organization of NSZs (FIG. 1D and FIG. 11E) and sealing rings (FIG. 11F). Colocalization (yellow) of cellular LPL (green) with integrin (red) was observed at 6 hours and 10 hours in NSZs. Arrows point to areas where integrin is colocalized with LPL (FIG. 11E and FIG. 11F). Colocalization was not observed at 3 hours in NSZs (FIG. 11D) and 10 hours in sealing rings (FIG. 1 IF). These observations were in line with a previous study showing that NSZs function as a hub for orchestrating integrin signaling (Ma et al., 2010, J. Biol. Chem., 285: 29911-29924). LPL phosphorylation is critical in the actin bundling process required for formation of NSZs. The fact that suppression of LPL phosphorylation and NSZs by the P1 peptide is fully consistent with the role LPL at the early stage of sealing ring formation. Reduced resorption of dentine in osteoclasts transduced with P1 peptide (FIG. 10) is ostensibly due to the attenuation of sealing ring formation.

Analyses of the Effects of Peptides on the Migration and Podosome Assembly

Figure 12:
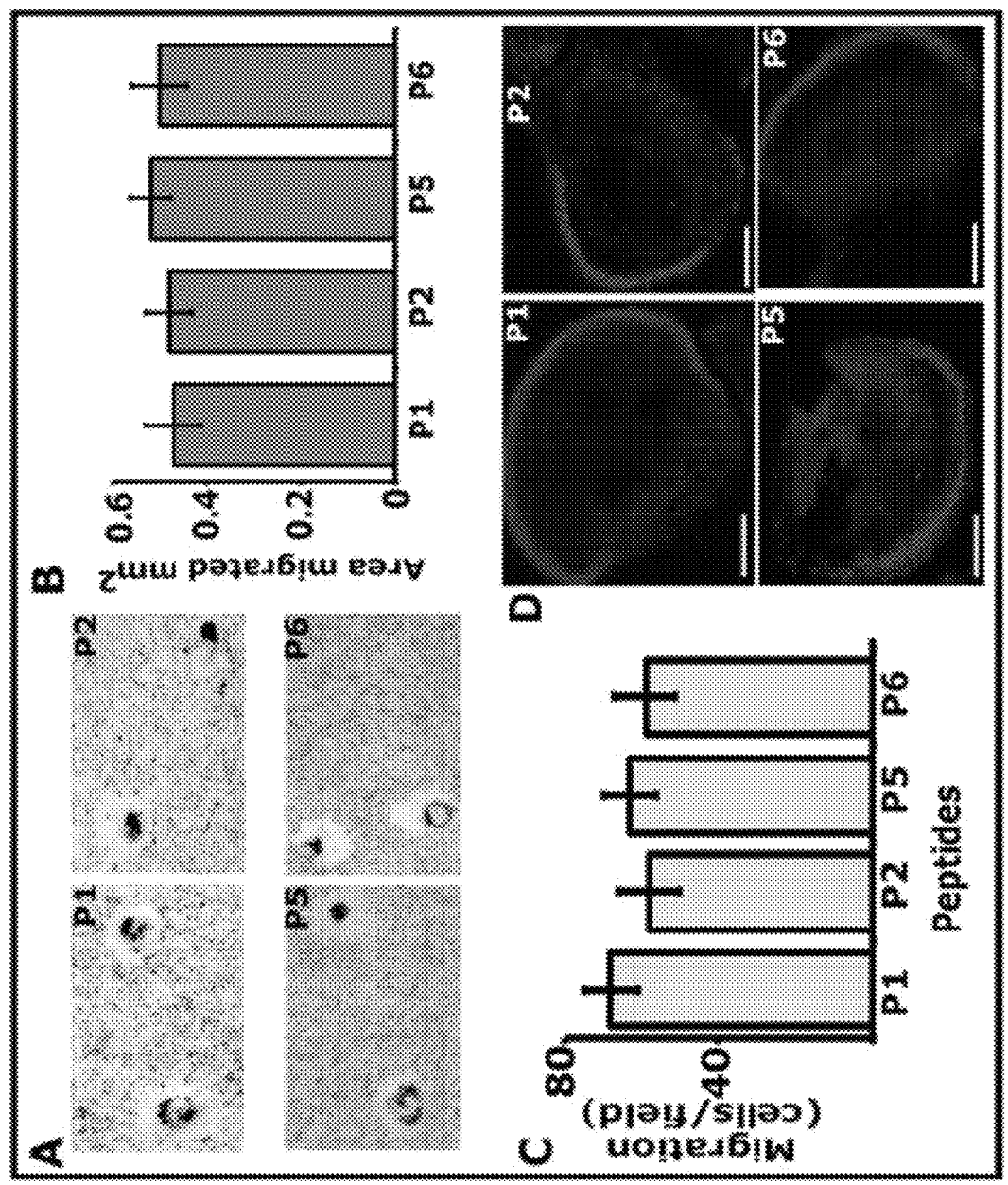
FIG. 12, comprising

LPL was shown to present in the podosomes of osteoclasts (Babb et al., 1997, Cell Motil. Cytosk., 37; 308-325). Podosomes are implicated in the migration of osteoclasts (Chellaiah et al., 2000, J. Biol. Chem., 275: 11993-12002; Chellaiah et al., 2000, J. Cell Biol., 148: 665-678; Chellaiah, 2006, Eur J Cell Biol 85: 311-317). Having observed that P1 peptide has significant inhibitory effects on the formation of NSZs, it was examined whether it would have a similar effect on podosome assembly and the migration of osteoclasts (FIG. 12). Migration was assessed using phagokinesis and Corning transwell migration assays (FIG. 12A-FIG. 12C). Neither the migration (FIG. 12A-FIG. 12C) nor the formation the podosomes (FIG. 12D) was affected by LPL peptides (P1, P2, P5, and P6). The results point to the importance of LPL phosphorylation in the actin bundling process required for the formation NSZs. This process is reduced in osteoclasts transduced with the P1 peptide.

Analyses in Osteoclasts Derived from RAW Cells

Figure 13:
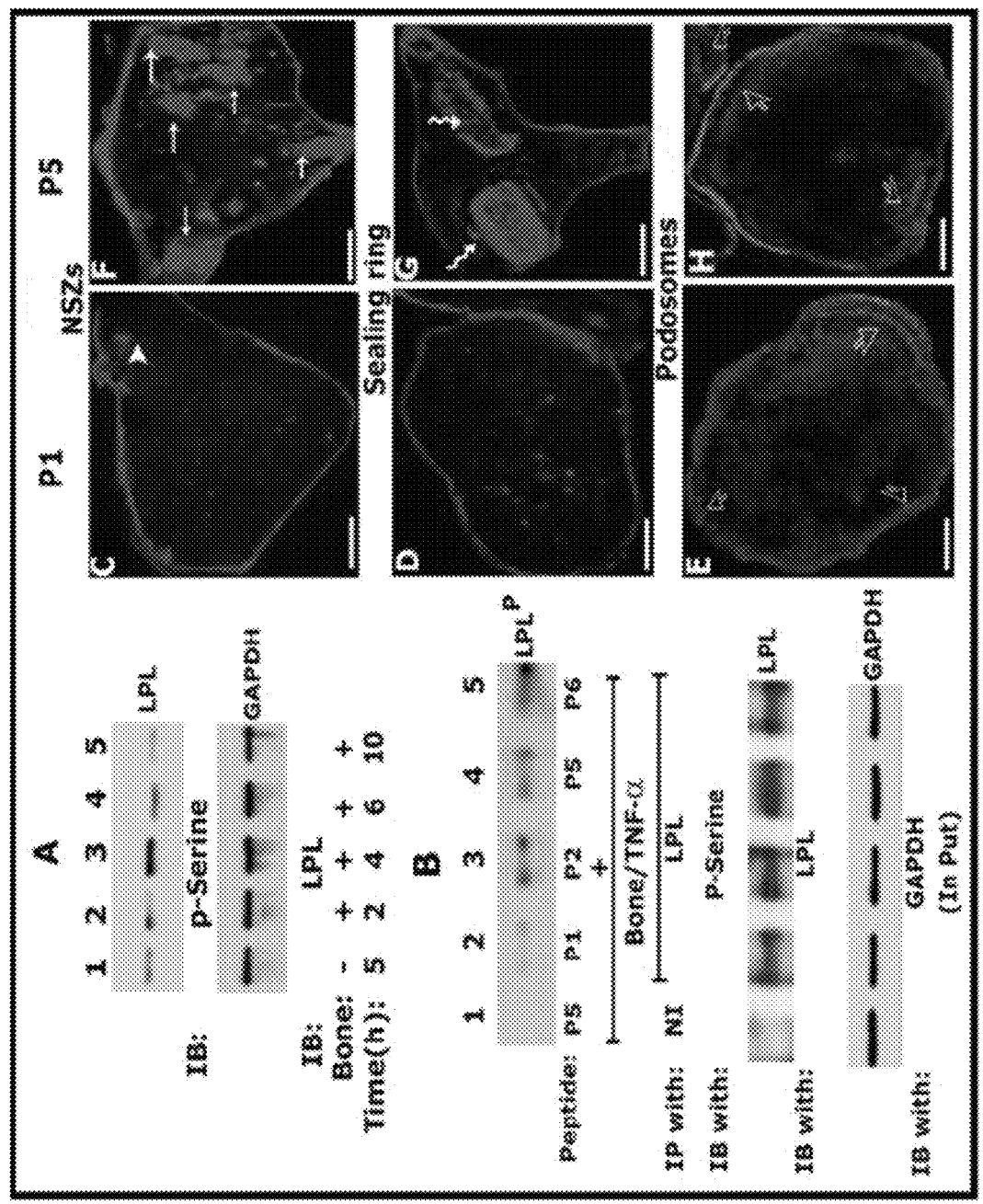
FIG. 13, comprising

The effects of LPL peptides on LPL phosphorylation and actin modulation was validated in osteoclasts derived from the RAW macrophage cell line. Consistent with the observations shown in mouse BM-derived osteoclasts (Ma et al., 2010, J. Biol. Chem., 285: 29911-29924), LPL level is maximum at 4 hours (FIG. 13A; top panel, lane 3) and decreased from 6 hours onwards (Lanes 4 and 5) in RAW cells derived osteoclasts treated with bone particles and TNF-α. Immunoblotting of the same blot with the GAPDH was used as a loading control (FIG. 13A; bottom panel). The effect of P1, P2, P5, and P6 peptides on the phosphorylation of endogenous LPL was evaluated by immunoprecipitation and immunoblotting analyses (FIG. 13B). P1 and P5 (scrambled) peptides was used to evaluate the organization of actin filaments in resorbing (FIG. 13C, FIG. 13D, FIG. 13F, and FIG. 13G) and nonresorbing (FIG. 13E and FIG. 13H) osteoclasts. Osteoclasts were stained with phalloidin to visualize filamentous actin in confocal microscopy. The finding of a significant decrease in the phosphorylation of cellular LPL (FIG. 13B, lane 2) and the formation of NSZs (FIG. 13C; P1) and sealing rings (FIG. 13D; P1) by P1 in osteoclasts derived from RAW cells well corroborates with the P1 peptide effects in mouse BM-derived osteoclasts (FIG. 8 and FIG. 9). The P1 peptide which has a significant effect on the formation of NSZs has no effect either on the pattern of podosome organization (FIG. 13E) or the migration of osteoclasts as compared with P5 peptide (FIG. 13H).

Figure 14:
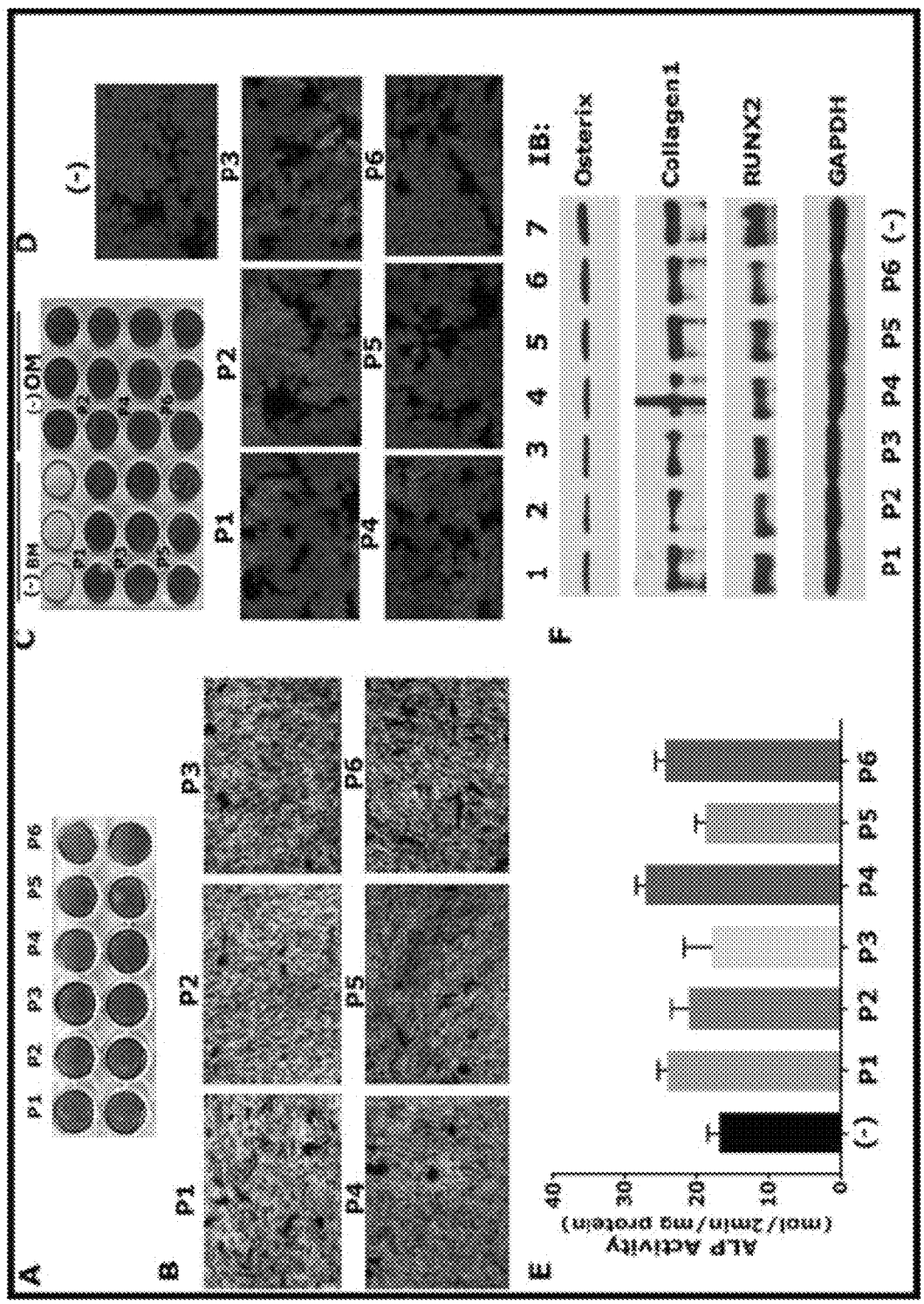
FIG. 14, comprising

Analyses of the Effect of Transduction of TAT-Fused LPL Peptides on Osteoblast Function Osteoblasts are the cells that make bone and these cells do not express LPL (Li et al., 2016, Asian J Androl 18: 716-722). The study has been extended to assess the effects of these peptides (P1-P6) on the mineralization process arbitrated by osteoblasts derived from MC3T3 (FIG. 14A and FIG. 14B) and UMR-106 cells (FIG. 14C-FIG. 14F) using ARS staining and ALP activity assay to determine the formation of mineralized matrix (FIG. 14A-FIG. 14E) and immunoblotting analyses to determine the expression of osteogenic biomarkers (Collagen 1, Osterix, and RUNX2; FIG. 14F). P1-P6 peptides did not affect the formation of the mineralized matrix (FIG. 14A-FIG. 14E) and the expression of osteogenic biomarkers for bone formation (FIG. 14F).

Figure 15:
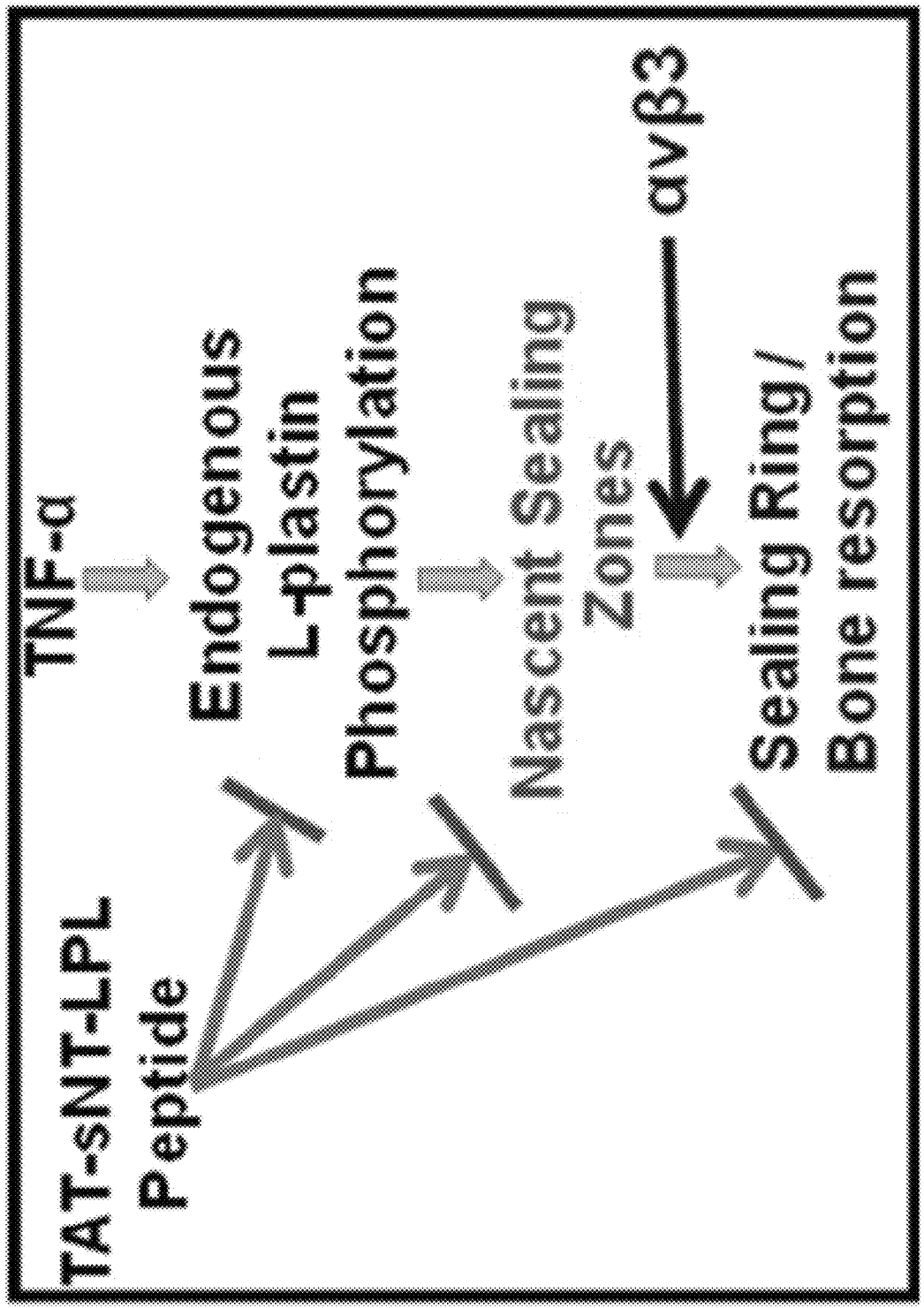
FIG. 15 depicts a proposed model of the role of L-Plastin (LPL) in nascent sealing zones (NSZs) formation. TNF-α signaling regulates the phosphorylation of LPL and NSZs formation independent of integrin αvβ3 signaling. It is shown here that sNT-LPL peptides can competitively block cellular or endogenous LPL phosphorylation and hence actin bundling process involved in NSZs formation. Hence bone resorption activity is significantly reduced. Therefore, it is suggested that these NSZs are the presumable precursor zones for fully functional sealing

Overall, the present data demonstrates the critical role of LPL in actin bundling process involved in the organization of NSZs. NSZs are the presumed precursor zones for sealing rings. As shown previously, the formation of NSZs is dependent on TNF-α signaling (Ma et al, 2010, J. Biol. Chem., 285: 29911-29924). Phosphorylation of LPL and the formation of NSZs by TNF-α signaling may be key elements at the early stage of sealing ring formation (FIG. 15).

Inhibition of LPL as a Pharmacological Tool to Reduce Bone Resorption

The mechanism by which osteoclasts coordinate sealing ring formation is not clear. It has been previously shown that cyclical changes in protein and phosphorylation levels of LPL and cortactin correspond with time-dependent changes in actin organization in osteoclasts subjected to bone resorption. LPL was shown to localize in the podosomes of monocytes derived osteoclasts (Babb et al., 1997, Cell Motil. Cytosk., 37: 308-325); however, little is known about its function. Further, the assembly of actin aggregates has been shown at the early stage of sealing ring formation by TNF-α or RANKL signaling independent of integrin αvβ3 signaling. These actin aggregates are denoted as nascent sealing zones (NSZs) (Ma et al., 2010, J. Biol. Chem., 285: 29911-29924). Osteoclasts derived from RAW cells corroborate previous observations that polymerization of actin generates a force to push the plasma membrane forward to produce membrane extensions. NSZs formed at the extensions serve as adhesive structures which facilitate the spreading of osteoclasts on bone. Expression and phosphorylation of LPL assists in the process of NSZ formation. Studies in T-lymphocytes have shown that LPL expression and phosphorylation at Ser-5 influences the localization of F-actin cytoskeletal protein and cellular polarization in response to chemokine stimulation (Freeley et al, 2012, J. Immunol., 188: 6357-6370). T cells deficient in LPL are defective in cellular polarization (Morley et al., 2010, J Immunol 184: 3628-3638). This suggests that LPL is a key regulator of T-cell receptor-mediated actin rearrangement required for the cellular polarization.

Osteoclasts polarize during bone resorption. It is not completely known whether LPL has any role in the polarization of osteoclasts on dentine or bone during resorption. It seems LPL plays a different role in osteoclasts. LPL is a key regulator of the actin bundling process which is required for sealing ring formation. Osteoclasts plated on dentine slices and treated with TNF-α displayed an actin cytoskeleton composed of NSZs which are the organization zone for sealing ring and subsequent formation of one or a few mature sealing rings. During the early stages of the maturation of sealing ring, actin patches are converted to ring-like configurations. Localization of LPL in NSZs and Cortactin in mature scaling rings has previously been shown (Ma et at, 2010, J. Biol. Chem., 285: 29911-29924).

L-plastin is phosphorylated on residues Ser-5 and Ser-7 in hematopoetic cells in vivo, but most likely on Ser-5 on non-hematopoietic cells. Phosphorylation of Ser-5 residue upstream of cytoskeletal rearrangements that underlie processes such as chemotaxis and adhesion (Chen et al., 2003, Immunity, 19: 95-104; Jones et al., 1996, J. Biol. Chem., 271: 14623-14630; Foran et al., 2006, Int. J. Cancer, 118: 2098-2104). Serine phosphorylation may have a direct role in the actin bundling function of LPL when expressed ectopically in Veto cells (Al et al., 2010, PLoS ONE, 5, e9210). LPL stabilizes actin filaments and protects them against depolymerization (Lebart et al., 2004, Biochemistry, 43: 2428-2437). The physiological function of Ser-7 phosphorylation is not known (Lin et at, 1998, DNA Cell Biol, 17: 1041-1046; Otsuka et at, 2001, Biochem Biophys Res Commun, 289: 876-881). To elucidate the role of LPL phosphorylation in NSZ formation, sNT-LPL peptides (10aa) were used. Peptide P1 exerts inhibitory effects on the function of cellular LPL as assayed by the levels of phosphorylation of cellular LPL, changes in actin dynamics and the capacity to resorb bone. Peptide P1 competitively reduced the function of cellular LPL more than the P3 and P4 with amino acid substitution at either Ser-5 or Ser-7. These results indicate that the phosphorylation of both Ser-5 and Ser-7 residues is important in LPL-mediated effects in osteoclasts. Inhibition of phosphorylation of cellular LPL reduced the actin bundling process mediated by the ABDs of cellular LPL. These results indicate that cooperativity between serine phosphorylation and actin binding to ABDs is required for the actin bundling process mediated by LPL.

As shown in neutrophils, regulation of actin bundling process by LPL is related to its phosphorylation on the serine residues (Wang et al., 1999, 3 Biol Chem 274: 24349-24356). In the time-course experiment, LPL plays a role in the formation of NSZs from 3 hours onwards which assist in the adhesion and spreading of OCs cultured on dentine slices. At 6 hours onwards localization of integrin αv was observed in NSZs. Integrin signaling supports the formation of bone resorption unit(s) (i.e. sealing rings) by remodeling of NSZs at 6 h onwards, at which time localization of LPL is reduced. The failure of the P1 peptide to bring about NSZs and sealing ring organization suggest that LPL phosphorylation is not only essential for NSZ formation but also for the recruitment of integrin in these structures for the maturation process, LPL peptide was shown to synergize with RGD ligand for the generation of conformational changes associated with the high-affinity state of integrin αvβ in PMNs (Wang et. al., 2001, J Biol Chem 276: 14474-14481. However, it is shown here that the Pt peptide functions as a competitive inhibitor of cellular or intracellular LPL-mediated actin dynamics. LPL phosphorylation increases the localization of integrin in NSZs. As shown previously (Ma et al., 2010, J. Biol. Chem., 285: 29911-29924), although LPL and integrin are diffusely localized in the cytoplasm of osteoclasts, their colocalization was observed predominantly at 6 hours at which time maturation of NSZs into fully functional sealing ring is initiated. The formation of actin aggregates by LPL assist in the localization of integrin and associated signaling molecules linked to the formation of sealing rings.

The role of LPL appears to be cell-type specific in the localization of integrin αvβ3 in PMNs (Wang et al., 2001, J Biol Chem 276: 14474-14481) and podosome formation in macrophages. This suggestion is based upon the observation that phosphorylated L-plastin is enriched in podosomes where it colocalizes with F-actin, consistent with the idea that its phosphorylation enhances F-actin binding and bundling (Janji et al., 2006, J Cell Sci, 119: 1947-1960). LPL was shown to be a vital protein for podosome formation and function in macrophages. Enrichment of phosphorylated LPL in podosomes emphasizing the actin bundling property of LPL in podosome stability. Expression of nanobodies generated against distinct domains of LPL perturbed matrix degradation, migration, podosome formation, and stability in THP-1 macrophages (De et al., 2013, PLoS ONE, 8: e78108). Although it is well established that osteoclasts contain LPL in podosomes (Babb et al., 1997, Cell Motil. Cytosk., 37: 308-325), little is known about the functional consequences of its expression. The Pt peptide which reduces the formation NSZs and sealing rings does not affect podosome formation or migration of osteoclasts. Superficial pits observed in P1 treated osteoclasts may be due to the degradation of matrix proteins by MMPs present in the podosomes during migration (Chellaiah et al., 2002, Calcif Tissue Int, 72: 197-205; Samanna et at, 2007, J Cell Physiol, 213: 710-720). This is the characteristic feature of highly invasive and migratory cells in which podosomes appear to be structures with adhesive/migratory functions accompanied by proteolytic degradation of the extracellular matrix (Blavier et al., 1995, J Cell Sci, 108 (Pt 12): 3649-3659; Sato et al., 1997, J Cell Sci, 110 (Pt 5): 589-596; Desai et al., 2008, J Biol Chem., 283: 13856-13866).

LPL plays a key role in the formation of NSZs and localization of αvβ3 in these zones. Due to the architectural nature of sealing rings, the major reorganization of actin filaments is required during their formation. Seating rings consisting of stable actin filaments generate tight sealing zones on the bone surface. NSZs formed by LPL function as a central point or a hub in assembling molecular components (integrin αvβ3, Src, cortactin, ERK, WASP, and Arp2/3) involved in the maturation of NSZs to fully functional mature sealing rings (Ma et al., 2010, J. Biol. Chem., 285: 29911-29924; Chellaiah et al., 2009, J Cell Physiol, 220:

382-393; Ma et al., 2008, J. Mol. Signal., 3: 4). Time-dependent changes in the localization of LPL in NSZs and cortactin in sealing rings suggest that these proteins may be involved in the initial and maturation phases of sealing rings, respectively (Ma et al., 2008, J. Mol. Signal., 3: 4).

Plastin 3 is expressed in osteoblasts. Mutations in plastin 3 resulted in osteoporosis in mice which signifies the role of plastin 3 in osteoblasts and not osteoclasts (Fahiminiya et al., 2014, J Bone Miner Res, 29: 1805-1814). Inhibition of bone resorption and not formation by PL peptide highlight the essentiality of LPL (aka plastin 2) in osteoclast sealing ring formation. The findings herein demonstrate the significance of LPL phosphorylation and function in NSZ formation at the early stage of sealing ring formation. Attenuation of NSZ formation in osteoclasts transduced with Pt peptide corroborates the importance of phosphorylation of LPL in osteoclast cytoskeletal remodeling involved in bone resorption.

Based on the results with LPL peptide, LPL not only has the potential to organize the actin bundling process involved in the formation of NSZs but also the stability of bundled F-actin for the maturation processes mediated integrin $\alpha v\beta 3$ signaling which involves several signaling, actin-binding, and regulatory proteins (Ma et al, 2010, J. Biol. Chem. 285: 29911-29924; Chellaiah et al., 2003, J Biol Chem 278: 29086-29097; Duong et al., 1999, J Bone Miner Metab, 17: 1-6; Miyazaki et al., 2004, J. Biol. Chem., 279: 17660-17666; Teitelbaum, 2011, Ann. N.Y. Acad, Sci., 1240: 14-17; Saltel et al., 2008, Eur J Cell, Biol, 87: 459-468). Within this study LPL is identified as a novel therapeutic target in osteoclast-mediated events. Also, sNT-LPL based manipulations of osteoclast bone resorption have the potential for pharmacological manipulations. It is concluded that LPL is indispensable to drive the actin bundling processes involved in sealing ring formation.

Example 3: Biodegradable Polymeric Nanoparticles Encapsulated with Small Molecular Weight L-Plastin Peptides Reduces Resorption Activity of Osteoclasts Tumor necrosis factor alpha (TNF-$\alpha$) was shown to stimulate the resorptive activity of osteoclasts (OCs) independent of integrin $\alpha v\beta 3$. The actual target of TNF-$\alpha$ signaling is unclear. The vital role of an actin-bundling protein L-plastin (LPL) in the assembly of nascent sealing zones (NSZs) at the early phase of sealing ring formation is described above. TNF-$\alpha$ signaling regulates the phosphorylation of LPL at Ser-5 and -7 residues and the assembly of NSZs. These studies prompted further experiments to gain more insight into the role of LPL phosphorylation on OC bone resorption. To examine whether reducing the phosphorylation of LPL attenuates the formation of NSZs and resorption, experiments were conducted with TAT-fused small molecular weight LPL peptide (P1) containing unmutated (P1: MARGSVSDEF (SEQ ID NO: 1)) and scrambled peptide (P5: SRSGMVEEAD) (SEQ ID NO: 5)). Polylactic-co-glycolic acid (PLGA) is an FDA approved polymer and a commonly used delivery system in bone tissue engineering. To deliver the peptides in a controlled and sustained fashion in vivo in mice, P1 or P5-loaded PLGA nanoparticles were formulated. Prior to injecting into mice, the P1 or P5-loaded PLGA nanoparticles (~150 nm) were characterized, and their effects on OCs in vitro was examined.

Figure 22:
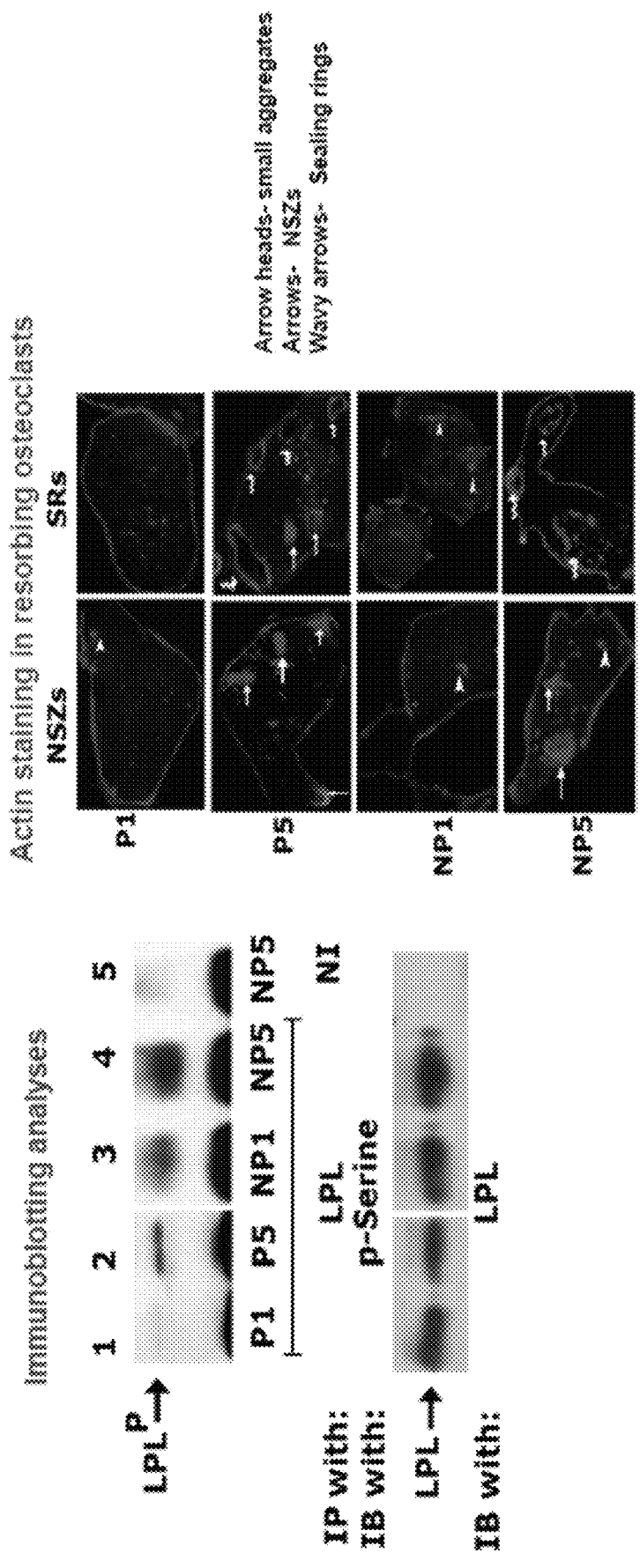
FIG. 22 depicts the results of example experiments demonstrating that that peptide 1 (P1) and nanoparticle-peptide 1 (NP1) (lanes 1 and 3) reduced the phosphorylation of endogenous LPL. As shown in mouse osteoclasts (FIG. 11), osteoclasts derived from RAW cells also demonstrated a decrease in the formation of NSZs and hence mature sealing rings (SRs) formation in response to P1 and NP1 treatment.

It was observed that transduction of TAT-fused P1 into OCs reduces the formation of both NSZs and bone resorption which is due to the selective inhibition of cellular LPL phosphorylation. Characterization of the peptide (P1 and P5) loaded nanoparticles demonstrated the following: a) Transmission electron microscopy (TEM) images showed well-dispersed spherical shaped nanoparticles (FIG. 17A-FIG. 17D). b) The release of peptides over three weeks period due to slow hydrolysis of biodegradable polymer over time (FIG. 18). c) both P1 and P5 nanoparticles had nearly neutral surface charge of −3.6 mV and −3.1 mV, respectively (FIG. 19). d) Incubation of OCs with peptide-loaded PLGA nanoparticles for 4 hours substantiates the significance of the inhibitory effect of the P1 peptide on LPL phosphorylation and NSZs formation (FIG. 22).

Experiments were conducted to analyze nanoparticle size, distribution and morphology. A narrow size distribution of PLGA-PEG_P1 (FIG. 17A) PLGA-PEG_P5 (FIG. 17B) nanoparticles is observed, measured by dynamic light scattering, TEM images show well dispersed round shaped PLGA-PEG_P1 (FIG. 17C) and PLGA-PEG_P5 (FIG. 17D) nanoparticles.

Figure 18:
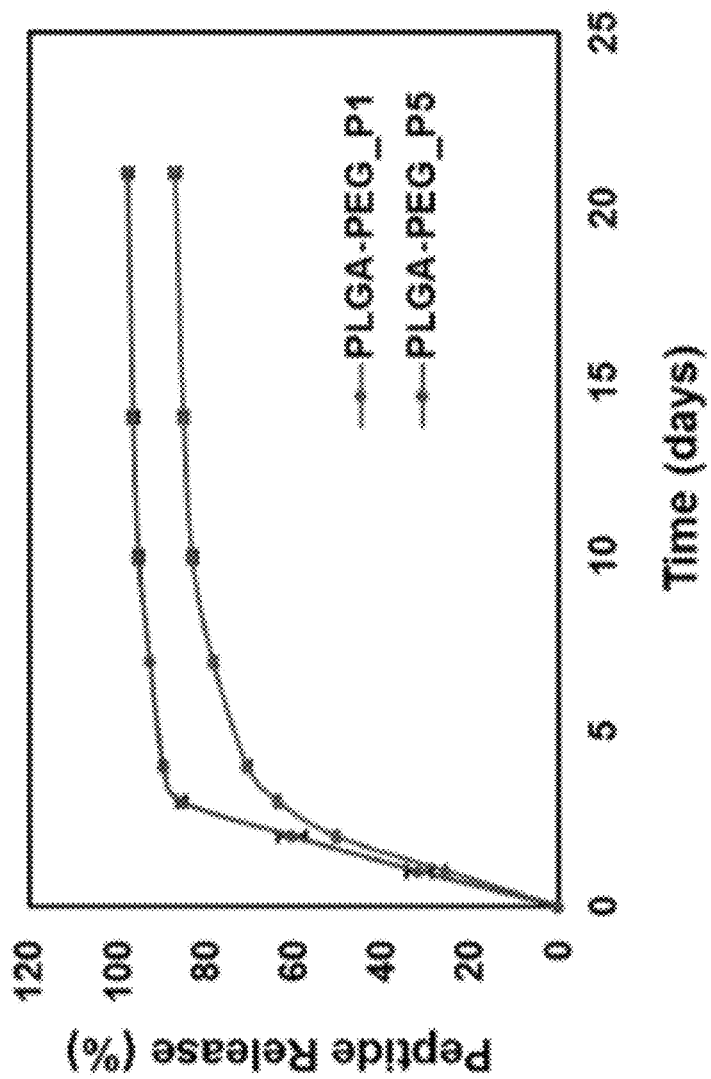
FIG. 18 depicts the results of example experiments. Peptide release profiles at 37 TC in PBS showing a biphasic release behavior—an initial fast release during first 3 days and a slow sustained release up to 3 weeks.

Peptide release experiments were also performed. Peptide release profiles at 37° C. in PBS show a biphasic release behavior—an initial fast release during first 3 days and a slow sustained release up to 3 weeks (FIG. 18).

The physiochemical characterization of the nanoparticles was performed, summarized in FIG. 19, showing that both P1 and P5 nanoparticles had nearly neutral surface charge of −3.6 mV and −3.1 mV, respectively.

Experiments were performed to evaluate LPL level in the presence of TNF-$\alpha$ and bone particles in osteoclasts derived from RAW cells (FIG. 20). As shown previously (Ma et al., 2010, J Biol Chem., 285: 2991-29924) in mouse osteoclasts, a time-dependent change in LPL level was observed in the presence of TNF-$\alpha$ and bone particles. An increase was observed at 4 hours and decreased gradually from 6 to 10 hours. Lane 1 is the LPL level in the absence of bone.

Figure 21:
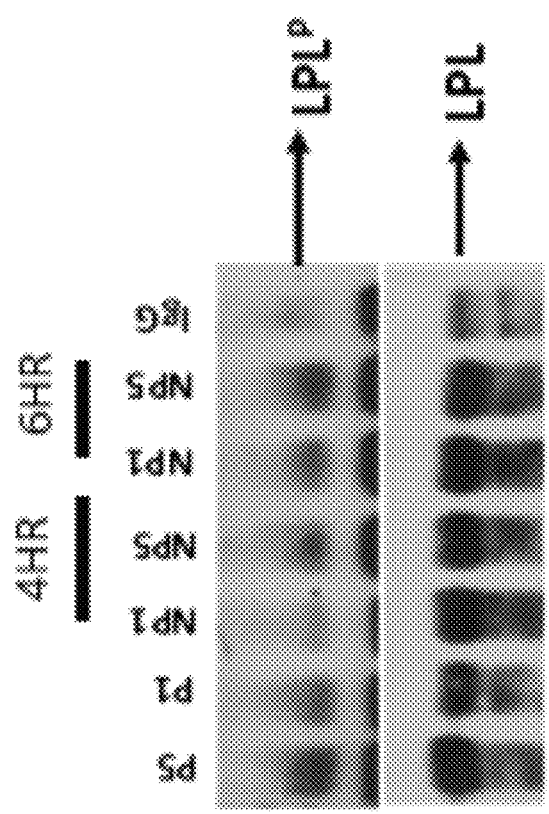
FIG. 21 depicts the results of example experiments demonstrating the effect of nanoparticles of P1 and P5 peptides on the phosphorylation of endogenous LPL.

FIG. 21 depicts the results of example experiments demonstrating the effect of nanoparticles of P1 and P5 peptides on the phosphorylation of endogenous LPL. FIG. 8B and FIG. 13B demonstrate that transduction of TAT-fused sNT-LPL-P1 peptide has the potential to reduce the phosphorylation of endogenous LPL; however, did not change the cellular levels of LPL. Similarly, uptake of PLGA-PEG_P1 (NP1) peptide significantly decreased the phosphorylation of endogenous LPL as compared with PLGA-PEG_P5 (NP5) peptide. The decrease was maximum at 4 hours. The effect of the P1 peptide on the inhibition of endogenous LPL is shown in lane 2. Although PLGA-PEG_P1 (NP1) displays a decrease in endogenous LPL at 6 hours, the decrease was more at 4 hours at which time an increase in the level of LPL was observed in the time-course study (FIG. 20).

FIG. 22 depicts the results of example experiments demonstrating that that peptide 1 (P1) and nanoparticle-peptide 1 (NP1) (lanes 1 and 3) reduced the phosphorylation of endogenous LPL. As shown in mouse osteoclasts (FIG. 11), osteoclasts derived from RAW cells also demonstrated a decrease in the formation of NSZs and hence mature sealing rings (SRs) formation in response to P1 and NP1 treatment.

Figure 23:
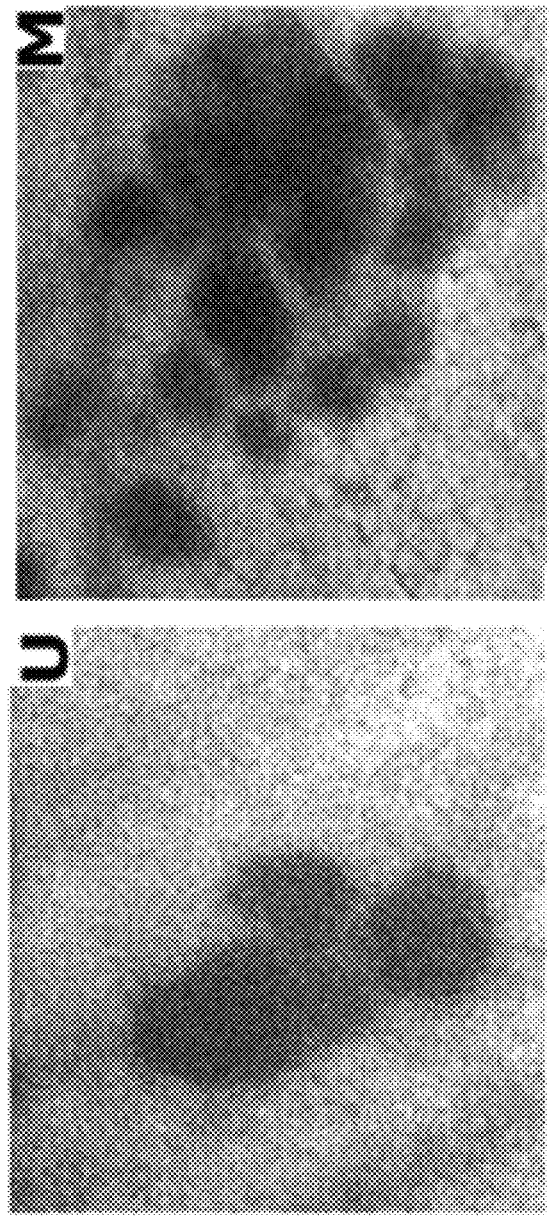
FIG. 23 depicts the results of example experiments demonstrating that nanoparticle-peptide 1 (NP1) significantly reduced bone resorption in osteoclasts derived from RAW cells.

FIG. 23 depicts the results of example experiments demonstrating that nanoparticle-peptide 1 (NP1) significantly reduced bone resorption in osteoclasts derived from RAW cells.

Attenuation of NSZs formation and bone resorption in OCs transduced with TAT-fused P1 demonstrates the importance of phosphorylation of LPL in OC function. Small molecular weight peptide-based manipulations of OC bone resorption have the potential for pharmacological manipulations. Inhibition of endogenous LPL phosphorylation and NSZs formation by P1-loaded PLGA nanoparticles suggests the entry of these particles into OCs in vitro.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for inhibiting bone resorption comprising an inhibitor of L-plastin (LPL), wherein the inhibitor comprises a fusion peptide comprising an N-terminal transduction domain derived from HIV-1 TAT and a C-terminal inhibitor domain, comprising an amino acid sequence selected from the group consisting of SEQ ID NO: 1, SEQ ID NO: 2, SEQ ID NO: 3, SEQ ID NO: 4, and SEQ ID NO: 34.

2. The composition of claim 1, wherein the transduction domain comprises the amino acid sequence of SEQ ID NO: 5.

3. The composition of claim 1, wherein the composition comprises a nanoparticle encapsulating the inhibitor.

4. The composition of claim 1, wherein the inhibitor domain is 15 amino acids or less in length.

* * * * *